(12) United States Patent
Kragh et al.

(10) Patent No.: US 8,753,859 B2
(45) Date of Patent: Jun. 17, 2014

(54) AMYLASE POLYPEPTIDES

(75) Inventors: Karsten Matthias Kragh, Viby J (DK); Anja Hemmingsen Kellet-Smith, Århus C (DK); René Mikkelsen, Skanderborg (DK); Rie Mejldal, Østbirk (DK); Rikke L. Bundgaard Jenner, Sabro (DK)

(73) Assignee: Dupont Nutrition Biosciences APS, Copenhagen (DK)

( * ) Notice: Subject to any disclaimer, the term of this patent is extended or adjusted under 35 U.S.C. 154(b) by 0 days.

(21) Appl. No.: 13/287,492

(22) Filed: Nov. 2, 2011

(65) Prior Publication Data

US 2012/0190075 A1    Jul. 26, 2012

Related U.S. Application Data

(63) Continuation-in-part of application No. PCT/EP2010/056913, filed on May 19, 2010.

(60) Provisional application No. 61/179,525, filed on May 19, 2009.

(30) Foreign Application Priority Data

May 19, 2009   (EP) .................................. 09160655

(51) Int. Cl.
| | |
|---|---|
| *C12N 9/28* | (2006.01) |
| *C12N 9/26* | (2006.01) |
| *C12Q 1/40* | (2006.01) |
| *C12P 19/14* | (2006.01) |
| *A23C 17/00* | (2006.01) |
| *A23L 1/31* | (2006.01) |
| *C07H 21/04* | (2006.01) |

(52) U.S. Cl.
USPC .............. 435/202; 435/201; 435/22; 435/99; 426/42; 426/56; 536/23.2

(58) Field of Classification Search
None
See application file for complete search history.

(56) References Cited

U.S. PATENT DOCUMENTS

| | | |
|---|---|---|
| 7,166,453 B2 | 1/2007 | Kragh et al. |
| 7,371,552 B2 | 5/2008 | Kragh et al. |
| 7,776,576 B2 | 8/2010 | Kragh et al. |
| 7,833,770 B2 | 11/2010 | Kragh et al. |
| 7,858,352 B2 | 12/2010 | Kragh et al. |
| 8,030,050 B2 | 10/2011 | Berg et al. |
| 2005/0136524 A1 | 6/2005 | Kragh et al. |
| 2007/0020727 A1* | 1/2007 | Berg et al. ..................... 435/69.1 |
| 2008/0107773 A1 | 5/2008 | Kragh et al. |
| 2008/0274531 A1 | 11/2008 | Berg et al. |
| 2009/0202675 A1 | 8/2009 | Derkx et al. |
| 2009/0214706 A1 | 8/2009 | Berg et al. |
| 2011/0212241 A1 | 9/2011 | Kragh et al. |

FOREIGN PATENT DOCUMENTS

| | | |
|---|---|---|
| WO | WO 92/00381 | 1/1992 |
| WO | WO 98/22613 | 5/1998 |
| WO | WO 02/068589 | 9/2002 |
| WO | WO 2004/091544 | 10/2004 |
| WO | WO 2004/111217 | 12/2004 |
| WO | WO 2005/007867 | 1/2005 |
| WO | WO 2006/003461 | 1/2006 |
| WO | WO 2007/007053 | 1/2007 |
| WO | WO 2007/148224 | 12/2007 |

OTHER PUBLICATIONS

UniProt Accession No. A4XX23 (herein after A4XX23, and created on May 29, 2007).*

* cited by examiner

*Primary Examiner* — Iqbal H Chowdhury
(74) *Attorney, Agent, or Firm* — Vedder Price P.C.; Thomas J. Kowalski

(57) ABSTRACT

This invention relates to polypeptides, more specifically amylase polypeptides and nucleic acids encoding these, and their uses e.g. as non-maltogenic exoamylases in producing food or feed products.

19 Claims, 2 Drawing Sheets

SEQUENCE LISTING

<160> NUMBER OF SEQ ID NOS: 72

<210> SEQ ID NO 1
<211> LENGTH: 429
<212> TYPE: PRT
<213> ORGANISM: Artificial Sequence
<220> FEATURE:
<223> OTHER INFORMATION: Mature protein sequence of pMS382

<400> SEQUENCE: 1

Asp Gln Ala Gly Lys Ser Pro Ala Gly Val Arg Tyr His Gly Asp
1               5                   10                  15

Glu Ile Ile Leu Gln Gly Phe His Trp Asn Val Val Arg Glu Ala Pro
                20                  25                  30

Tyr Asn Trp Tyr Asn Ile Leu Arg Gln Gln Ala Ser Thr Ile Ala Ala
                35                  40                  45

Asp Gly Phe Ser Ala Ile Trp Met Pro Val Pro Trp Arg Asp Phe Ser
            50                  55                  60

Ser Trp Thr Asp Gly Asp Lys Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
            115                 120                 125

Leu Pro Ala Gly Gln Arg Phe Trp Arg Asn Asp Cys Pro Asp Pro Gly
130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
            195                 200                 205

Asp Ser Ala Asp Ser Ser Phe Cys Val Gly Glu Leu Trp Lys Glu Pro
        210                 215                 220

Ser Glu Tyr Pro Pro Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Lys Trp Pro Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

```
Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
        370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
                420                 425

<210> SEQ ID NO 2
<211> LENGTH: 531
<212> TYPE: PRT
<213> ORGANISM: Artificial Sequence
<220> FEATURE:
<223> OTHER INFORMATION: Mature protein of G4 amylase of Pseudomonas
      sp. AM1 (2006) with M added at the N-terminus (Q1EJP2 protein)

<400> SEQUENCE: 2

Met Asp Leu Ala Gly Lys Ser Pro Gly Gly Val Arg Tyr His Gly Gly
1               5                   10                  15

Asp Glu Ile Ile Leu Gln Gly Phe His Trp Asn Val Ile Arg Glu Ser
                20                  25                  30

Pro Asn Asn Trp Tyr Asn Thr Leu Arg Asp Met Ala Pro Thr Ile Ala
            35                  40                  45

Ala Asp Gly Phe Ser Ala Ile Trp Met Pro Val Pro Trp Arg Asp Phe
        50                  55                  60

Ser Ser Trp Ser Asp Gly Ala Asn Ser Gly Gly Glu Gly Tyr Phe
65                  70                  75                  80

Trp His Asp Phe Asn Lys Asn Gly Arg Tyr Gly Ser Asp Thr Gln Leu
                85                  90                  95

Lys Gln Ala Ala Gly Ala Leu Asn Asn Ala Gln Val Lys Val Leu Tyr
            100                 105                 110

Asp Val Val Pro Asn His Met Asn Arg Gly Tyr Pro Asp Lys Gln Ile
        115                 120                 125

Asn Leu Pro Ala Gly Gln Gly Phe Trp Arg Asn Asp Cys Ala Asp Pro
130                 135                 140

Gly Asn Tyr Pro Asn Asp Cys Asp Asp Gly Asp Arg Phe Met Gly Gly
145                 150                 155                 160

Asp Ala Asp Leu Asn Thr Ala Asn Pro Gln Val Tyr Gly Met Phe Arg
                165                 170                 175

Asp Glu Phe Ala Asn Leu Arg Ser Asn Tyr Gly Ala Gly Gly Phe Arg
            180                 185                 190

Phe Asp Phe Val Arg Gly Tyr Ala Gly Glu Arg Val Asp Ser Trp Met
        195                 200                 205

Gly Ala Ala His Asp Asn Ala Phe Cys Val Gly Glu Leu Trp Lys Ala
    210                 215                 220

Pro Ala Glu Tyr Pro Ser Trp Asp Trp Arg Asn Thr Ala Ser Trp Gln
225                 230                 235                 240

Gln Val Ile Lys Asp Trp Ser Asp Arg Ala Lys Cys Pro Val Phe Asp
                245                 250                 255

Phe Ala Leu Lys Glu Arg Met Gln Asn Gly Ser Ile Ala Asp Trp Lys
            260                 265                 270

Asn Gly Leu Asn Gly Asn Pro Asp Pro Arg Trp Arg Glu Val Ala Val
        275                 280                 285
```

```
Thr Phe Val Asp Asn His Asp Ala Gly Tyr Ser Pro Gly Gln Asn Gly
    290                 295                 300
Gly Gln His His Trp Ala Leu Gln Asp Gly Leu Ile Arg Gln Ala Tyr
305                 310                 315                 320
Ala Tyr Ile Leu Thr Ser Pro Gly Thr Pro Val Val Tyr Trp Ser His
                325                 330                 335
Met Tyr Asp Trp Gly Tyr Gly Asp Phe Ile Arg Gln Leu Ile Gln Val
                340                 345                 350
Arg Arg Thr Ala Gly Val Arg Ala Asp Ser Ala Ile Ser Phe His Ser
            355                 360                 365
Gly Tyr Ser Gly Leu Val Ala Thr Val Ser Gly Ser Gln Gln Thr Leu
    370                 375                 380
Val Val Ala Leu Asn Ser Asp Leu Ala Asn Pro Gly Gln Val Ala Ser
385                 390                 395                 400
Gly Ser Phe Ser Glu Ala Val Asn Ala Ser Asn Gly Gln Val Arg Val
                405                 410                 415
Trp Arg Ser Gly Ser Gly Asp Gly Gly Asn Asp Gly Gly Glu Gly
                420                 425                 430
Gly Leu Val Asn Val Asn Phe Arg Cys Asp Asn Gly Val Thr Gln Met
            435                 440                 445
Gly Asp Ser Val Tyr Ala Val Gly Asn Val Ser Gln Leu Gly Asn Trp
    450                 455                 460
Ser Pro Ala Ser Ala Val Arg Leu Thr Asp Thr Ser Ser Tyr Pro Thr
465                 470                 475                 480
Trp Lys Gly Ser Ile Ala Leu Pro Asp Gly Gln Asn Val Glu Trp Lys
                485                 490                 495
Cys Leu Ile Arg Asn Glu Ala Asp Ala Thr Leu Val Arg Gln Trp Gln
            500                 505                 510
Ser Gly Gly Asn Asn Gln Val Gln Ala Ala Gly Ala Ser Thr Ser
    515                 520                 525
Gly Ser Phe
    530
```

<210> SEQ ID NO 3
<211> LENGTH: 1596
<212> TYPE: DNA
<213> ORGANISM: Artificial Sequence
<220> FEATURE:
<223> OTHER INFORMATION: DNA sequence of nucleotide encoding G4 amylase of Pseudomonas sp. AM1 (2006) (Q1EJP2) with M added at the N-terminus (Q1EJP2 DNA):

<400> SEQUENCE: 3

```
atggatctgg caggcaaatc accgggcggc gttagatatc atggcggcga tgaaattatt      60
ctgcaaggct tcattggaa tgttattaga gaatcaccga taattggta taatacactg      120
agagatatgg caccgacaat tgcagcagat ggcttttcag caatttggat gccggttccg      180
tggagagatt tttcatcatg gtcagatggc gcaaattcag gcggcggcga aggctatttt      240
tggcatgatt ttaataaaaa tggcagatat ggctcagata cacaactgaa acaagcagca      300
ggcgcactga ataatgcaca agttaaagtt ctgtatgatg ttgttccgaa tcatatgaat      360
agaggctatc cggataaaca aattaatctg ccggcaggcc aaggcttttg gagaaatgat      420
tgcgcagatc cggcaatta tccgaatgat tgcgatgatg cgatagatt tatgggcggc      480
gatgctgatc tgaatacagc aaatccgcaa gttatggca tgtttagaga tgaatttgca      540
aatctgagat caaattatgg cgcaggcggc tttagatttg attttgttag aggctatgca      600
```

```
ggcgaaagag ttgattcatg gatgggcgca gcacatgata atgcattttg cgttggcgaa    660
ctgtggaaag caccggcaga atatccgtca tgggattgga gaaatacagc atcatggcaa    720
caagttatta aagattggtc agatagagca aaatgcccgg tttttgattt tgcactgaaa    780
gaaagaatgc aaaatggctc aattgcagat tggaaaaatg gcctgaatgg caatccggat    840
ccgagatgga gagaagttgc agttacattt gttgataatc atgatgcagg ctattcaccg    900
ggccaaaatg gcggccaaca tcattgggca ctgcaagatg gcctgattag acaagcatat    960
gcatatattc tgacatcacc gggcacaccg gttgtttatt ggtcacatat gtatgattgg   1020
ggctatggcg attttattag acaactgatt caagttagaa aacagcagg cgttagagca    1080 gattcagcaa tttcatttca ttcaggctat tcaggcctgg ttgcaacagt ttcaggctca   1140
caacaaacac tggttgttgc actgaatagc gatctggcaa atccgggcca agttgcatca   1200
ggctcatttt cagaagcagt taatgcatca aatggccaag ttagagtttg gagatcaggc   1260
tcaggcgatg gcggcggcaa tgatggcggc gaaggcggcc tggttaatgt taattttaga   1320
tgcgataatg gcgttacaca aatgggcgat tcagtttatg cagttggcaa tgtttcacaa   1380
ctgggcaatt ggtcaccggc atcagcagtt agactgacag atacatcatc atatccgaca   1440
tggaaaggct caattgcact gccggatggc caaaatgttg aatggaaatg cctgattaga   1500
aatgaagcag atgcaacact ggttagacaa tggcaatcag cggcaataa tcaagttcaa    1560 gcagcagcag gcgcatcaac atcaggctca ttttaa                              1596

<210> SEQ ID NO 4
<211> LENGTH: 534
<212> TYPE: PRT
<213> ORGANISM: Artificial Sequence
<220> FEATURE:
<223> OTHER INFORMATION: Mature protein of G4 amylase of Pseudomonas
      sp. 7193 with M added at the N-terminus (A5CVD5 protein)

<400> SEQUENCE: 4

Met Asp Leu Ala Gly Lys Ser Pro Gly Gly Val Arg Tyr His Gly Gly
1               5                   10                  15

Asp Glu Ile Ile Leu Gln Gly Phe His Trp Asn Val Ile Arg Glu Ser
            20                  25                  30

Pro Asn Asn Trp Tyr Asn Thr Leu Arg Asp Met Ala Pro Thr Ile Ala
        35                  40                  45

Ala Asp Gly Phe Ser Ala Ile Trp Met Pro Val Pro Trp Arg Asp Phe
    50                  55                  60

Ser Ser Trp Ser Asp Gly Ala Asn Ser Gly Gly Glu Gly Tyr Phe
65                  70                  75                  80

Trp His Asp Phe Asn Lys Asn Gly Arg Tyr Gly Ser Asp Thr Gln Leu
                85                  90                  95

Lys Gln Ala Ala Gly Ala Leu Asn Asn Ala Gln Val Lys Val Leu Tyr
            100                 105                 110

Asp Ala Val Pro Asn His Met Asn Arg Gly Tyr Pro Asp Lys Gln Ile
        115                 120                 125

Asn Leu Pro Ala Gly Gln Gly Phe Trp Arg Asn Asp Cys Ala Asp Pro
    130                 135                 140

Gly Asn Tyr Pro Asn Asp Cys Asp Asp Gly Asp Arg Phe Met Gly Gly
145                 150                 155                 160

Asp Ala Asp Leu Asn Thr Ala Asn Pro Gln Val Tyr Gly Met Phe Arg
                165                 170                 175

Asp Glu Phe Ala Asn Leu Arg Ser Asn Tyr Gly Ala Gly Gly Phe Arg
            180                 185                 190
```

Phe Asp Phe Val Arg Gly Tyr Ala Gly Glu Arg Val Asp Ser Trp Met
         195                 200                 205

Gly Asp Gly Ala Cys Gln Arg Leu Leu Arg Gly Arg Ala Leu Glu Gly
    210                 215                 220

Thr Gly Arg Ile Pro Glu Leu Gly Leu Ala Gln Tyr Gly Gln Leu Ala
225                 230                 235                 240

Ala Val Ile Lys Asp Trp Ser Asp Arg Ala Lys Val Pro Gly Cys Ser
                245                 250                 255

Asn Phe Ala Leu Lys Gly Ala His Ala Glu Arg Leu Pro Ser Pro Thr
            260                 265                 270

Gly Arg Thr Ala Ser Thr Ala Thr Pro Met Pro Arg Trp Arg Glu Val
        275                 280                 285

Ala Val Thr Phe Val Asp Asn His Asp Thr Gly Tyr Ser Pro Gly Gln
    290                 295                 300

Asn Gly Gly Gln His His Trp Ala Leu Arg Asp Asp Leu Val Arg Gln
305                 310                 315                 320

Ala Tyr Ala Tyr Ile Leu Ala Ser Pro Gly Thr Pro Val Val Tyr Trp
                325                 330                 335

Ser His Met Tyr Asp Trp Gly His Gly Pro Leu Ile Arg Gln Leu Ile
            340                 345                 350

Gln Ile Arg Arg Ala Ala Gly Val Arg Ala Asp Ser Ala Ile Glu Phe
        355                 360                 365

His Ser Gly Tyr Ser Gly Leu Val Ala Thr Val Arg Gly Thr Ala Gln
    370                 375                 380

Thr Leu Val Met Ala Leu Gly Ser Asn Leu Ser Ser Pro Ala Glu Val
385                 390                 395                 400

Ser Ser Gly Ser Phe Ser Gln Ala Leu Asn Gln Asp Ser Gly Gln Leu
                405                 410                 415

Arg Ile Trp Thr Thr Gly Ser Thr Gly Gly Asp Glu Gly Asp Gly Gly
            420                 425                 430

Gly Asp Gly Thr Met Val Ser Val Asn Phe Arg Cys Asp Asn Gly Ile
        435                 440                 445

Thr Gln Pro Gly Asp Ser Val Tyr Ala Val Gly Ser Leu Ala Gln Leu
    450                 455                 460

Gly Ser Trp Ser Pro Ala Asn Ala Val Arg Leu Thr Asp Val Ser Asn
465                 470                 475                 480

Tyr Pro Thr Trp Lys Gly Ala Ile Ser Leu Pro Ala Gly Gln Ala Val
                485                 490                 495

Glu Trp Lys Cys Ile Val Arg Ser Glu Ala Asp Pro Thr Gln Val Arg
            500                 505                 510

Gln Trp Gln Ala Gly Asp Asn Asn Arg Val Thr Ala Gly Ala Gly Ala
        515                 520                 525

Thr Thr Ile Gly Arg Leu
    530

<210> SEQ ID NO 5
<211> LENGTH: 1605
<212> TYPE: DNA
<213> ORGANISM: Artificial Sequence
<220> FEATURE:
<223> OTHER INFORMATION: DNA sequence of nucleotide encoding G4 amylase
      of Pseudomonas sp. 7193 (A5CVD5) with M added at the N-terminus
      (A5CVD5 DNA)

<400> SEQUENCE: 5
atggatctgg caggcaaatc accgggcggc gttagatatc atggcggcga tgaaattatt    60

-continued

```
ctgcaaggct tcattggaa tgttattaga gaatcaccga ataattggta taatacactg      120
agagatatgg caccgacaat tgcagcagat ggcttttcag caatttggat gccggttccg      180
tggagagatt tttcatcatg gtcagatggc gcaaattcag gcggcggcga aggctatttt      240
tggcatgatt ttaataaaaa tggcagatat ggctcagata cacaactgaa acaagcagca      300
ggcgcactga ataatgcaca agttaaagtt ctgtatgatg cagttccgaa tcatatgaat      360
agaggctatc cggataaaca aattaatctg ccggcaggcc aaggcttttg agaaaatgat      420
tgcgcagatc cgggcaatta tccgaatgat tgcgatgatg gcgatagatt tatgggcggc      480
gatgctgatc tgaatacagc aaatccgcaa gtttatggca tgtttagaga tgaatttgca      540
aatctgagat caaattatgg cgcaggcggc tttagatttg atttttgttag aggctatgca      600 ggcgaaagag ttgattcatg gatgggcgat ggcgcatgcc aaagactgct gagaggcaga      660
gcactggaag gcacaggcag aattccggaa ctgggcctgg cacaatatgg ccaactggca      720
gcagttatta aagattggtc agatagagca aaagttccgg gctgctcaaa ttttgcactg      780
aaaggcgcac atgcagaaag actgccgtca ccgacaggca gaacagcatc aacagcaaca      840
ccgatgccga gatggagaga gttgcagtt acatttgttg ataatcatga tacaggctat      900
tcaccgggcc aaaatggcgg ccaacatcat tgggcactga gagatgatct ggttagacaa      960
gcatatgcat atattctggc atcaccgggc acaccggttg tttattggtc acatatgtat     1020
gattggggtc atggaccgct gattagacaa ctgattcaaa ttagaagagc agcaggcgtt     1080
agagcagatt cagcaattga atttcattca ggctattcag gcctggttgc aacagttaga     1140
ggcacagcac aaacactggt tatggcactg ggctcaaatc tgtcatcacc ggcagaagtt     1200
tcatcaggct cattttcaca agcactgaat caagattcag gccaactgag aatttggaca     1260
acaggctcaa caggcggcga tgaaggcgat ggcggcggcg atggcacaat ggtttcagtt     1320
aattttagat gcgataatgg cattacacaa ccgggcgatt cagtttatgc agttggctca     1380
ctggcacaac tgggctcatg gtcaccggca aatgcagtta gactgacaga tgtttcaaat     1440
tatccgacat ggaaaggcgc aatttcactg ccggcaggcc aagcagttga atggaaatgc     1500
attgttagat cagaagcaga tccgacacaa gttagacaat ggcaagcagg cgataataat     1560
agagttacag caggcgcagg cgcaacaaca attggcagac tgtaa                     1605
```

<210> SEQ ID NO 6
<211> LENGTH: 528
<212> TYPE: PRT
<213> ORGANISM: Artificial Sequence
<220> FEATURE:
<223> OTHER INFORMATION: Mature protein of G4 amylase of Pseudomonas
      mendocina (strain ymp) with M added at the N-terminus (A4XX23
      protein)

<400> SEQUENCE: 6

```
Met Asp Ala Pro Gly Lys Thr Ala Ser Gly Val Arg Tyr His Gly Gly
1               5                   10                  15

Asp Glu Ile Ile Leu Gln Gly Phe His Trp Asn Thr Val Arg Thr Ser
            20                  25                  30

Ser Asn Trp Tyr Ala Thr Leu Ala Ser Met Ala Pro Thr Leu Ala Ala
        35                  40                  45

Asp Gly Phe Ser Ala Ile Trp Met Pro Val Pro Trp Arg Asp Phe Ser
    50                  55                  60

Ser Trp Ser Asp Pro Gly Asn Gly Thr Ser Gly Gly Glu Gly Tyr
65                  70                  75                  80
```

Phe Trp His Asp Phe Asn Lys Asn Gly Arg Tyr Gly Ser Asp Ser Leu
                85                  90                  95
Leu Arg Gln Ala Ala Ser Ala Leu Asn Ala Ala Gly Val Lys Pro Ile
            100                 105                 110
Tyr Asp Val Val Pro Asn His Met Asn Arg Gly Tyr Pro Asp Lys Glu
        115                 120                 125
Ile Asn Leu Pro Ala Gly Gln Gly Leu Trp Arg His Asp Cys Asn Asp
    130                 135                 140
Pro Gly Asn Tyr Ala Asn Asp Cys Asp Asp Gly Asp Arg Phe Met Gly
145                 150                 155                 160
Gly Asp Ala Asp Leu Asn Thr Gly His Pro Gln Asn Tyr Ala Met Phe
                165                 170                 175
Arg Asp Glu Phe Ala Arg Leu Arg Ser Gln Tyr Gly Ala Gly Gly Phe
            180                 185                 190
Arg Phe Asp Phe Val Arg Gly Tyr Ala Gly Glu Arg Val Ala Ser Trp
        195                 200                 205
Met Ser Asp Ala His Asp Asn Gly Phe Cys Leu Gly Glu Leu Trp Lys
    210                 215                 220
Ala Pro Gly Glu Tyr Pro Ser Trp Asp Trp Arg Asn Gly Ala Ser Trp
225                 230                 235                 240
Gln Gln Ile Leu Lys Asp Trp Ser Asp Arg Ala Lys Cys Thr Val Phe
                245                 250                 255
Asp Phe Ala Leu Lys Glu Arg Met Gln Asn Gly Gly Ile Ala Asp Trp
            260                 265                 270
Arg His Gly Leu Asn Gly Asn Pro Asp Ala Arg Trp Arg Glu Val Ala
        275                 280                 285
Val Thr Phe Val Asp Asn His Asp Thr Gly Tyr Ser Pro Gly Pro His
    290                 295                 300
Gly Gly Gln His His Trp Pro Leu Pro Asp Ala Arg Leu Lys Gln Ala
305                 310                 315                 320
Tyr Ala Tyr Ile Leu Ser Ser Pro Gly Thr Pro Val Val Tyr Trp Pro
                325                 330                 335
His Met Tyr Asp Trp Gly His Gly Asp Phe Ile Arg Gln Leu Ile Gln
            340                 345                 350
Ile Arg Arg Ala Ala Gly Val Lys Ala Ala Ser Ala Ile Gln Phe His
        355                 360                 365
Thr Gly Phe Ser Gly Leu Val Ala Thr Ile Ser Gly Ser Gln Gln Gln
    370                 375                 380
Leu Leu Ile Ala Leu Asp Ser Asn Leu Ser Ser Pro Gly Gln Val Ala
385                 390                 395                 400
Ser Gly Asp Phe Thr Gln Ala Leu Asn Thr Asp Asn Gly Ala Ile Arg
                405                 410                 415
Ile Trp Arg Ser Gly Gln Gly Gly Asp Gly Gln Gly Asn Leu Val
            420                 425                 430
Ser Val Asn Phe Arg Cys Asp Asn Gly Val Thr Gln Trp Gly Asp Ser
        435                 440                 445
Val Tyr Ala Leu Gly Asn Val Thr Gln Leu Gly Asn Trp Ser Pro Ala
    450                 455                 460
Gly Ala Val Arg Leu Thr Asp Thr Ser Ala Tyr Pro Thr Trp Lys Gly
465                 470                 475                 480
Ser Ile Ala Leu Pro Ala Gly Gln Gln Val Gln Trp Lys Cys Ile Val
                485                 490                 495
Arg Ser Glu Ser Asn Pro Thr Gln Val Lys Thr Trp Gln Pro Gly Gly
            500                 505                 510

Asn Asn Ser Val Thr Val Ala Ser Gly Ala Ser Thr Ala Gly Ser Phe
        515                 520                 525

<210> SEQ ID NO 7
<211> LENGTH: 1587
<212> TYPE: DNA
<213> ORGANISM: Artificial Sequence
<220> FEATURE:
<223> OTHER INFORMATION: DNA sequence of nucleotide encoding G4 amylase
      of Pseudomonas mendocina (strain ymp) (A4XX23) with M added at
      the N-terminus: (A4XX23 DNA)

<400> SEQUENCE: 7
atggatgcac cgggcaaaac agcatcaggc gttagatatc atggcggcga tgaaattatt        60
ctgcaaggct tcattggaa tacagttaga acatcatcaa attggtatgc aacactggca       120
tcaatggcac cgacactggc agcagatggc ttttcagcaa tttggatgcc ggttccgtgg       180
agagattttt catcatggtc agatccgggc aatggcacat caggcggcgg cgaaggctat       240
ttttggcatg attttaataa aaatggcaga tatggctcag attcactgct gagacaagca       300
gcatcagcac tgaatgcagc aggcgttaaa ccgatttatg atgttgttcc gaatcatatg       360
aatagaggct atccggataa agaaattaat ctgccggcag gccaaggcct gtggagacat       420
gattgcaatg atccgggcaa ttatgcaaat gattgcgatg atggcgatag atttatgggc       480
ggcgatgctg atctgaatac aggccatccg caaaattatg caatgtttag atgaatt          540 gcaagactga gatcacaata tggcgcaggc ggctttagat ttgattttgt tagaggctat       600
gcaggcgaaa gagttgcatc atggatgtca gatgcacatg ataatggctt ttgcctgggc       660
gaactgtgga agcaccgggc gaatatccg tcatgggatt ggagaaatgg cgcatcatgg       720
caacaaattc tgaaagattg gtcagataga gcaaaatgca cagttttga ttttgcactg       780 aaagaaagaa tgcaaaatgg cggcattgca gattggagac atggcctgaa tgcaatccg       840 gatgcaagat ggagagaagt tgcagttaca tttgttgata tcatgatac aggctattca       900 ccgggcccgc atggcggcca acatcattgg ccgctgccgg atgcaagact gaaacaagca       960
tatgcatata ttctgtcatc accgggcaca ccggttgttt attggccgca tatgtatgat      1020
tggggtcatg gagatttat tagacaactg attcaaatta aagagcagc aggcgttaaa      1080 gcagcatcag caattcaatt tcatacaggc ttttcaggcc tggttgcaac aatttcaggc      1140
tcacaacaac aactgctgat tgcactggat tcaaatctgt catcaccggg ccaagttgca      1200
tcaggcgatt ttacacaagc actgaataca gataatggcg caattagaat ttggagatca      1260
ggccaaggcg gcggcgatgg ccaaggcaat ctggtttcag ttaattttag atgcgataat      1320
ggcgttacac aatggggcga ttcagtttat gcactgggca tgttacaca actgggcaat      1380 tggtcaccgg caggcgcagt tagactgaca gatacatcag catatccgac atggaaaggc      1440
tcaattgcac tgccggcagg ccaacaagtt caatggaaat gcattgttag atcagaatca      1500
aatccgacac aagttaaaac atggcaaccg ggcggcaata attcagttac agttgcatca      1560
ggcgcatcaa cagcaggctc attttaa                                          1587

<210> SEQ ID NO 8
<211> LENGTH: 413
<212> TYPE: PRT
<213> ORGANISM: Artificial Sequence
<220> FEATURE:
<223> OTHER INFORMATION: Mature protein of G4 amylase of Hahella
      chejuensis (strain KCTC 2396) with M added at the N-terminus
      (Q2SEA8 protein)

<400> SEQUENCE: 8

```
Met Glu Ser Ser Gly Lys Ser Gly Ala Gly Val Arg Phe His Gly Gly
1               5                   10                  15

Asp Glu Ile Ile Leu Gln Gly Phe His Trp Asn Val Val Arg Thr Ala
            20                  25                  30

Glu Arg Asn Trp Tyr Asn Ile Leu Gln Ser Lys Ala Gln Gln Ile Ser
        35                  40                  45

Glu Asp Gly Phe Thr Ala Ile Trp Met Pro Val Pro Trp Arg Asp Asn
    50                  55                  60

Ser Ser Trp Gln Ala Ser Ser Asp Thr Arg Phe Gly Gly Glu Gly Tyr
65                  70                  75                  80

Phe Trp Ala Asp Met Asp Lys Asn Ser Arg Tyr Gly Asp Asp Gly Gln
                85                  90                  95

Leu Lys Gln Ala Ala Ser Ala Leu Lys Asn Lys Gly Val Lys Val Ile
            100                 105                 110

Tyr Asp Ile Val Pro Asn His His Asp Arg Gly His Ser Asn Asp Ser
        115                 120                 125

Leu Asn Leu Pro Ser Gly Gln Gly Tyr Tyr Arg Ser Asp Cys Ser Ser
    130                 135                 140

Cys Asp Asp Gly Asp Pro Phe Met Asp Gly Gly Ser Asp Phe Ser Thr
145                 150                 155                 160

Ala His Pro Asp Val Tyr Asp Leu Phe Lys Asn Glu Leu Val Asn Leu
                165                 170                 175

Lys Thr Asn Tyr Ser Ala Gly Gly Phe Arg Phe Asp Phe Val Arg Gly
            180                 185                 190

Tyr Ala Pro Glu Arg Ile Ser Ala Trp Met Ser Ala Ser Leu Asp Ser
        195                 200                 205

Gly Tyr Cys Val Gly Glu Leu Trp Lys Gly Pro Ser Glu Tyr Pro Ser
    210                 215                 220

Trp Asp Trp Arg His Ser Ala Ser Trp Gln Glu Ile Leu Lys Asp Phe
225                 230                 235                 240

Thr Asp Ala Ser Asp Cys Ser Val Phe Asp Phe Ala Leu Lys Glu Arg
                245                 250                 255

Met Gln Asn Gly Ser Ile Ser Asp Trp Arg Tyr Gly Leu Asn Gly Asn
            260                 265                 270

Pro Ser Ala Gln Trp Arg Glu Val Ala Val Thr Phe Val Asp Asn His
        275                 280                 285

Asp Thr Gly Tyr Ser Pro Gly Pro Leu Gly Gly Gln His His Trp Ala
    290                 295                 300

Leu Pro Asp Trp Lys Arg Lys Met Ala Tyr Ala Tyr Ile Leu Ser Ser
305                 310                 315                 320

Pro Gly Thr Pro Val Val Tyr Trp Pro His Met Tyr Asp Trp Gly Met
                325                 330                 335

Arg Asp Phe Ile Arg Asn Leu Ile Gln Leu Arg Lys Ser Ala Gly Val
            340                 345                 350

Lys Ala Tyr Ser Gly Val Gln Phe His Asp Gly Phe Ser Gly Leu Val
        355                 360                 365

Gly Thr Thr Ser Gly Ser Asn Gly Lys Leu Leu Phe Ala Ile Asp Ser
    370                 375                 380

Asn Phe Ser Ser Pro Asn Gln Val Ala Gly Gly Ala Trp Asn Leu Ala
385                 390                 395                 400

Val Asn Glu Asp Asn Gly Arg Ile Arg Ile Trp Arg Gln
                405                 410
```

<210> SEQ ID NO 9
<211> LENGTH: 1242
<212> TYPE: DNA
<213> ORGANISM: Artificial Sequence
<220> FEATURE:
<223> OTHER INFORMATION: DNA sequence of nucleotide encoding of G4 amylase of Hahella chejuensis (strain KCTC 2396) with M added at the N-terminus (Q2SEA8 DNA)

<400> SEQUENCE: 9

```
atggaatcat caggcaaatc aggcgcaggc gttagatttc atggcggcga tgaaattatt      60
ctgcaaggct tcattggaa  cgttgttaga acagcagaaa gaaactgta  caacatcctg     120
caatcaaaag cacaacaaat tcagaagat  ggctttacag caatttggat gccggttccg     180
tggagagata attcatcatg gcaagcatca tcagatacaa gatttggcgg cgaaggctat     240
ttttgggcag atatggataa aaattcaaga tatggcgatg atggccaact gaaacaagca     300
gcatcagcac tgaaaaataa aggcgttaaa gttatttatg atattgttcc gaatcatcat     360
gatagaggcc attcaaatga ttcactgaat ctgccgtcag gccaaggcta ttatagatca     420
gattgctcat catgcgatga tggcgatccg tttatggatg cggctcaga  tttttcaaca     480
gcacatccgg atgtttacga tctgtttaaa acgaactgg  ttaacctgaa aacaaactac     540
tcagcaggcg gctttagatt tgattttgtt agaggctatg caccggaaag aatttcagca     600
tggatgtcag catcactgga ttcaggctat tgcgttggcg aactgtggaa aggcccgtca     660
gaatatccgt catgggattg gagacattca gcatcatggc aagaaattct gaaagatttt     720
acagatgcat cagattgctc agtttttgat tttgcactga agaaagaat  gcaaaatggc     780
tcaatttcag attggagata tggcctgaat ggcaatccgt cagcacaatg gagagaagtt     840
gcagttacat ttgttgataa tcatgataca ggctattcac cgggcccgct gggcggccaa     900
catcattggg cactgccgga ttggaaaaga aaaatggcat atgcatatat tctgtcatca     960
ccgggcacac cggttgttta ttggccgcat atgtatgatt ggggcatgag agatttat    1020
agaaatctga ttcaactgag aaaatcagca ggcgttaaag catattcagg cgttcaattt    1080
catgatggct tttcaggcct ggttggcaca acatcaggct caaatggcaa actgctgttt    1140
gcaattgatt caaattttc  atcaccgaat caagttgcag cggcgcatg  gaatctggca    1200
gttaatgaag ataatggcag aattagaatt tggagacaat aa                       1242
```

<210> SEQ ID NO 10
<211> LENGTH: 530
<212> TYPE: PRT
<213> ORGANISM: Pseudomonas saccharophila

<400> SEQUENCE: 10

```
Asp Gln Ala Gly Lys Ser Pro Ala Gly Val Arg Tyr His Gly Gly Asp
 1               5                  10                  15

Glu Ile Ile Leu Gln Gly Phe His Trp Asn Val Val Arg Glu Ala Pro
             20                  25                  30

Asn Asp Trp Tyr Asn Ile Leu Arg Gln Gln Ala Ser Thr Ile Ala Ala
         35                  40                  45

Asp Gly Phe Ser Ala Ile Trp Met Pro Val Pro Trp Arg Asp Phe Ser
     50                  55                  60

Ser Trp Thr Asp Gly Gly Lys Ser Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95
```

```
Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
130                 135                 140

Asn Tyr Pro Asn Asp Cys Asp Gly Asp Arg Phe Ile Gly Gly Glu
145                 150                 155                 160

Ser Asp Leu Asn Thr Gly His Pro Gln Ile Tyr Gly Met Phe Arg Asp
                165                 170                 175

Glu Leu Ala Asn Leu Arg Ser Gly Tyr Gly Ala Gly Phe Arg Phe
                180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Gly Pro
        210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
        290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
            355                 360                 365

Tyr Ser Gly Leu Val Ala Thr Val Ser Gly Ser Gln Gln Thr Leu Val
370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly Glu Gly Gly
            420                 425                 430

Leu Val Asn Val Asn Phe Arg Cys Asp Asn Gly Val Thr Gln Met Gly
            435                 440                 445

Asp Ser Val Tyr Ala Val Gly Asn Val Ser Gln Leu Gly Asn Trp Ser
        450                 455                 460

Pro Ala Ser Ala Val Arg Leu Thr Asp Thr Ser Ser Tyr Pro Thr Trp
465                 470                 475                 480

Lys Gly Ser Ile Ala Leu Pro Asp Gly Gln Asn Val Glu Trp Lys Cys
                485                 490                 495

Leu Ile Arg Asn Glu Ala Asp Ala Thr Leu Val Arg Gln Trp Gln Ser
            500                 505                 510

Gly Gly Asn Asn Gln Val Gln Ala Ala Gly Ala Ser Thr Ser Gly
            515                 520                 525
```

Ser Phe
    530

<210> SEQ ID NO 11
<211> LENGTH: 21
<212> TYPE: PRT
<213> ORGANISM: Pseudomonas saccharophila

<400> SEQUENCE: 11

Met Ser His Ile Leu Arg Ala Ala Val Leu Ala Ala Val Leu Leu Pro
1               5                   10                  15

Phe Pro Ala Leu Ala
            20

<210> SEQ ID NO 12
<211> LENGTH: 429
<212> TYPE: PRT
<213> ORGANISM: Artificial Sequence
<220> FEATURE:
<223> OTHER INFORMATION: Mature protein sequence of pMS1776

<400> SEQUENCE: 12

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Lys Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Asp Lys Ser Gly Gly Glu Gly Tyr Phe Trp
65                  70                  75                  80

His Asp Phe Asn Lys Asn Gly Leu Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ser Pro
    210                 215                 220

Ser Glu Tyr Pro Pro Trp Asp Trp Arg Asn Arg Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr

```
                275                 280                 285
Phe Val Asp Asn His Asp Thr Gly Tyr Ser Pro Gly Gln Asn Gly Gly
        290                 295                 300
Gln His Lys Trp Pro Leu Pro Asp Gly Leu Ile Arg Gln Ala Tyr Ala
305                 310                 315                 320
Tyr Ile Leu Thr Ser Pro Gly Thr Pro Val Val Tyr Trp Pro His Met
                325                 330                 335
Tyr Asp Trp Gly Tyr Gly Asp Phe Ile Arg Gln Leu Ile Gln Val Arg
                340                 345                 350
Arg Thr Ala Gly Val Arg Ala Asp Ser Ala Ile Ser Phe His Ser Gly
                355                 360                 365
Tyr Ser Gly Leu Val Ala Thr Val Ser Gly Ser Gln Gln Thr Leu Val
        370                 375                 380
Val Ala Leu Asn Ser Asp Leu Asp Asn Pro Gly Gln Val Ala Ser Gly
385                 390                 395                 400
Ser Phe Ser Glu Ala Val Asn Ala Ser Asn Gly Gln Val Arg Val Trp
                405                 410                 415
Arg Ser Gly Ser Gly Asp Gly Gly Asn Asp Gly Gly
                420                 425
```

<210> SEQ ID NO 13
<211> LENGTH: 429
<212> TYPE: PRT
<213> ORGANISM: Artificial Sequence
<220> FEATURE:
<223> OTHER INFORMATION: Mature protein sequence of pMS1934

<400> SEQUENCE: 13

```
Asp Gln Ala Gly Lys Ser Pro Ala Gly Val Arg Tyr His Gly Gly Asp
1               5                   10                  15
Glu Ile Ile Leu Gln Gly Phe His Trp Asn Val Val Arg Glu Ala Pro
                20                  25                  30
Tyr Asn Trp Tyr Asn Ile Leu Arg Gln Lys Ala Ser Thr Ile Ala Ala
            35                  40                  45
Asp Gly Phe Ser Ala Ile Trp Met Pro Val Pro Trp Arg Asp Phe Ser
        50                  55                  60
Ser Trp Thr Asp Gly Asp Lys Ser Gly Gly Glu Gly Tyr Phe Trp
65                  70                  75                  80
His Asp Phe Asn Lys Asn Gly Leu Tyr Gly Ser Asp Ala Gln Leu Arg
                85                  90                  95
Gln Ala Ala Gly Ala Leu Gly Gly Ala Gly Val Lys Val Leu Tyr Asp
                100                 105                 110
Val Val Pro Asn His Met Asn Arg Phe Tyr Pro Asp Lys Glu Ile Asn
                115                 120                 125
Leu Pro Ala Gly Gln Arg Phe Trp Arg Asn Asp Cys Pro Asp Pro Gly
        130                 135                 140
Asn Gly Pro Asn Asp Cys Asp Asp Gly Asp Arg Phe Leu Gly Gly Glu
145                 150                 155                 160
Ala Asp Leu Asn Thr Gly His Pro Gln Ile Tyr Gly Met Phe Arg Asp
                165                 170                 175
Glu Phe Thr Asn Leu Arg Ser Gly Tyr Gly Ala Gly Gly Phe Arg Phe
                180                 185                 190
Asp Phe Val Arg Gly Tyr Ala Pro Glu Arg Val Asp Ser Trp Met Ser
            195                 200                 205
Asp Ser Ala Asp Ser Ser Phe Cys Val Gly Glu Leu Trp Lys Lys Pro
        210                 215                 220
```

```
Ser Glu Tyr Pro Pro Trp Asp Trp Arg Asn Arg Ala Ser Trp Gln Gln
225                 230                 235                 240

Ile Ile Lys Asp Trp Ser Asp Arg Ala Lys Cys Pro Val Phe Asp Phe
            245                 250                 255

Ala Leu Lys Glu Arg Met Gln Asn Gly Ser Val Ala Asp Trp Lys Asp
        260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
        290                 295                 300

Gln His Lys Trp Pro Leu Pro Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
            370                 375                 380

Val Ala Leu Asn Ser Asp Leu Asp Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
            420                 425

<210> SEQ ID NO 14
<211> LENGTH: 429
<212> TYPE: PRT
<213> ORGANISM: Artificial Sequence
<220> FEATURE:
<223> OTHER INFORMATION: Mature protein sequence of pMS2020

<400> SEQUENCE: 14

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Lys Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Asp Lys Ser Gly Gly Glu Gly Tyr Phe Trp
65                  70                  75                  80

His Asp Phe Asn Lys Asn Gly Leu Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Gly Pro Asn Asp Cys Asp Asp Gly Asp Arg Phe Leu Gly Gly Glu
145                 150                 155                 160
```

Ala Asp Leu Asn Thr Gly His Pro Gln Ile Tyr Gly Met Phe Arg Asp
            165                 170                 175

Glu Phe Thr Asn Leu Arg Ser Gly Tyr Gly Ala Gly Phe Arg Phe
        180                 185                 190

Asp Phe Val Arg Gly Tyr Ala Pro Glu Arg Val Asp Ser Trp Met Ser
            195                 200                 205

Asp Ser Ala Asp Ser Ser Phe Cys Val Gly Glu Leu Trp Lys Ser Pro
            210                 215                 220

Ser Glu Tyr Pro Pro Trp Asp Trp Arg Asn Arg Ala Ser Trp Gln Gln
225                 230                 235                 240

Ile Ile Lys Asp Trp Ser Asp Arg Ala Lys Cys Pro Val Phe Asp Phe
            245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
            290                 295                 300

Gln His Lys Trp Pro Leu Pro Asp Gly Leu Ile Arg Gln Ala Tyr Ala
305                 310                 315                 320

Tyr Ile Leu Thr Ser Pro Gly Thr Pro Val Val Tyr Trp Pro His Met
            325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
            355                 360                 365

Tyr Ser Gly Leu Val Ala Thr Val Ser Gly Ser Gln Gln Thr Leu Val
            370                 375                 380

Val Ala Leu Asn Ser Asp Leu Asp Asn Pro Gly Gln Val Ala Ser Gly
385                 390                 395                 400

Ser Phe Ser Glu Ala Val Asn Ala Glu Asn Gly Gln Val Arg Val Trp
            405                 410                 415

Arg Ser Gly Ser Gly Asp Gly Gly Asn Asp Gly Gly
            420                 425

<210> SEQ ID NO 15
<211> LENGTH: 429
<212> TYPE: PRT
<213> ORGANISM: Artificial Sequence
<220> FEATURE:
<223> OTHER INFORMATION: Mature protein sequence of pMS2022

<400> SEQUENCE: 15

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Lys Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Asp Lys Ser Gly Gly Glu Tyr Phe Trp
65                  70                  75                  80

His Asp Phe Asn Lys Asn Gly Leu Tyr Gly Ser Asp Ala Gln Leu Arg
            85                  90                  95

Gln Ala Ala Gly Ala Leu Gly Gly Ala Gly Val Lys Val Leu Tyr Asp

```
            100                 105                 110
Val Val Pro Asn His Met Asn Arg Phe Tyr Pro Asp Lys Glu Ile Asn
            115                 120                 125

Leu Pro Ala Gly Gln Arg Phe Trp Arg Asn Asp Cys Pro Asp Pro Gly
            130                 135                 140

Asn Gly Pro Asn Asp Cys Asp Gly Asp Arg Phe Leu Gly Gly Glu
145                 150                 155                 160

Ala Asp Leu Asn Thr Gly His Pro Gln Ile Tyr Gly Met Phe Arg Asp
            165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Leu Trp Met Ser
            195                 200                 205

Asp Ser Ala Asp Ser Ser Phe Cys Val Gly Glu Leu Trp Lys Ser Pro
            210                 215                 220

Ser Glu Tyr Pro Pro Trp Asp Trp Arg Asn Arg Ala Ser Trp Gln Gln
225                 230                 235                 240

Ile Ile Lys Asp Trp Ser Asp Arg Ala Lys Cys Pro Val Phe Asp Phe
            245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
            290                 295                 300

Gln His Lys Trp Pro Leu Pro Asp Gly Leu Ile Arg Gln Ala Tyr Ala
305                 310                 315                 320

Tyr Ile Leu Thr Ser Pro Gly Thr Pro Val Val Tyr Trp Pro His Met
            325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
            355                 360                 365

Tyr Ser Gly Leu Val Ala Thr Val Ser Gly Ser Gln Gln Thr Leu Val
            370                 375                 380

Val Ala Leu Asn Ser Asp Leu Asp Asn Pro Gly Gln Val Ala Ser Gly
385                 390                 395                 400

Ser Phe Ser Glu Ala Val Asn Ala Glu Asn Gly Gln Val Arg Val Trp
            405                 410                 415

Arg Ser Gly Ser Gly Asp Gly Gly Asn Asp Gly Gly
            420                 425
```

<210> SEQ ID NO 16
<211> LENGTH: 429
<212> TYPE: PRT
<213> ORGANISM: Artificial Sequence
<220> FEATURE:
<223> OTHER INFORMATION: Mature protein sequence of pMS2062

<400> SEQUENCE: 16

```
Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Lys Ala Ser Thr Ile Ala Ala
            35                  40                  45
```

```
Asp Gly Phe Ser Ala Ile Trp Met Pro Val Pro Trp Arg Asp Phe Ser
    50                  55                  60

Ser Trp Thr Asp Gly Asp Lys Ser Gly Gly Glu Gly Tyr Phe Trp
65                  70                  75                  80

His Asp Phe Asn Lys Asn Gly Leu Tyr Gly Ser Asp Ala Gln Leu Arg
                85                  90                  95

Gln Ala Ala Gly Ala Leu Gly Gly Ala Gly Val Lys Val Leu Tyr Asp
                100                 105                 110

Val Val Pro Asn His Met Asn Arg Phe Tyr Pro Asp Lys Glu Ile Asn
            115                 120                 125

Leu Pro Ala Gly Gln Arg Phe Trp Arg Asn Asp Cys Pro Asp Pro Gly
    130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
                180                 185                 190

Asp Phe Val Arg Gly Tyr Ala Pro Glu Arg Val Asp Ser Trp Met Ser
            195                 200                 205

Asp Ser Ala Asp Ser Ser Phe Cys Val Gly Glu Leu Trp Lys Lys Pro
    210                 215                 220

Ser Glu Tyr Pro Pro Trp Asp Trp Arg Asn Arg Ala Ser Trp Gln Glu
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
                260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
    290                 295                 300

Gln His Lys Trp Pro Leu Pro Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
                340                 345                 350

Arg Thr Ala Gly Val Arg Ala Asp Ser Ala Ile Ser Phe His Ser Gly
            355                 360                 365

Tyr Ser Gly Leu Val Ala Thr Val Ser Gly Ser Gln Gln Thr Leu Val
    370                 375                 380

Val Ala Leu Asn Ser Asp Leu Asp Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
                420                 425
```

<210> SEQ ID NO 17
<211> LENGTH: 429
<212> TYPE: PRT
<213> ORGANISM: Artificial Sequence
<220> FEATURE:
<223> OTHER INFORMATION: Mature protein sequence of pMS2171

<400> SEQUENCE: 17

```
Asp Gln Ala Gly Lys Ser Pro Ala Gly Val Arg Tyr His Gly Gly Asp
1               5                   10                  15
Glu Ile Ile Leu Gln Gly Phe His Trp Asn Val Val Arg Glu Ala Pro
            20                  25                  30
Tyr Asn Trp Tyr Asn Ile Leu Arg Gln Lys Ala Ser Thr Ile Ala Ala
        35                  40                  45
Asp Gly Phe Ser Ala Ile Trp Met Pro Val Pro Trp Arg Asp Phe Ser
    50                  55                  60
Ser Trp Thr Asp Gly Asp Lys Ser Gly Gly Glu Gly Tyr Phe Trp
65                  70                  75                  80
His Asp Phe Asn Lys Asn Gly Leu Tyr Gly Ser Asp Ala Gln Leu Arg
                85                  90                  95
Gln Ala Ala Gly Ala Leu Gly Gly Ala Gly Val Lys Val Leu Tyr Asp
            100                 105                 110
Val Val Pro Asn His Met Asn Arg Phe Tyr Pro Asp Lys Glu Ile Asn
        115                 120                 125
Leu Pro Ala Gly Gln Arg Phe Trp Arg Asn Asp Cys Pro Asp Pro Gly
    130                 135                 140
Asn Gly Pro Asn Asp Cys Asp Asp Gly Asp Arg Phe Leu Gly Gly Glu
145                 150                 155                 160
Ala Asp Leu Asn Thr Gly His Pro Gln Ile Tyr Gly Met Phe Arg Asp
                165                 170                 175
Glu Phe Thr Asn Leu Arg Ser Gly Tyr Gly Ala Gly Phe Arg Phe
            180                 185                 190
Asp Phe Val Arg Gly Tyr Ala Pro Glu Arg Val Asp Leu Trp Met Ser
        195                 200                 205
Asp Ser Ala Asp Ser Ser Phe Cys Val Gly Glu Leu Trp Lys Ala Pro
    210                 215                 220
Ser Glu Tyr Pro Pro Trp Asp Trp Arg Asn Arg Ala Ser Trp Gln Gln
225                 230                 235                 240
Ile Ile Lys Asp Trp Ser Asp Arg Ala Lys Cys Pro Val Phe Asp Phe
                245                 250                 255
Ala Leu Lys Glu Arg Met Gln Asn Gly Ser Val Ala Asp Trp Lys His
            260                 265                 270
Gly Leu Asn Gly Asn Pro Asp Pro Arg Trp Arg Glu Val Ala Val Thr
        275                 280                 285
Phe Val Asp Asn His Asp Thr Gly Tyr Ser Pro Gly Gln Asn Gly Gly
    290                 295                 300
Gln His Lys Trp Pro Leu Pro Asp Gly Leu Ile Arg Gln Ala Tyr Ala
305                 310                 315                 320
Tyr Ile Leu Thr Ser Pro Gly Thr Pro Val Val Tyr Trp Pro His Met
                325                 330                 335
Tyr Asp Trp Gly Tyr Gly Asp Phe Ile Arg Gln Leu Ile Gln Val Arg
            340                 345                 350
Arg Thr Ala Gly Val Arg Ala Asp Ser Ala Ile Ser Phe His Ser Gly
        355                 360                 365
Tyr Ser Gly Leu Val Ala Thr Val Ser Gly Ser Gln Gln Thr Leu Val
    370                 375                 380
Val Ala Leu Asn Ser Asp Leu Asp Asn Pro Gly Gln Val Ala Ser Gly
385                 390                 395                 400
Ser Phe Ser Glu Ala Val Asn Ala Glu Asn Gly Gln Val Arg Val Trp
                405                 410                 415
```

```
Arg Ser Gly Ser Gly Asp Gly Gly Asn Asp Gly Gly
            420                 425

<210> SEQ ID NO 18
<211> LENGTH: 429
<212> TYPE: PRT
<213> ORGANISM: Artificial Sequence
<220> FEATURE:
<223> OTHER INFORMATION: Mature protein sequence of pMS465

<400> SEQUENCE: 18

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Asp Lys Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ser Pro
    210                 215                 220

Ser Glu Tyr Pro Pro Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Lys Trp Pro Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350
```

Arg Thr Ala Gly Val Arg Ala Asp Ser Ala Ile Ser Phe His Ser Gly
    355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
                420                 425

<210> SEQ ID NO 19
<211> LENGTH: 429
<212> TYPE: PRT
<213> ORGANISM: Artificial Sequence
<220> FEATURE:
<223> OTHER INFORMATION: Mature protein sequence of pMS1042

<400> SEQUENCE: 19

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Asp Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Glu Pro
    210                 215                 220

Ser Glu Tyr Pro Pro Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly

```
            290                 295                 300
Gln His Lys Trp Pro Leu Pro Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
                340                 345                 350

Arg Thr Ala Gly Val Arg Ala Asp Ser Ala Ile Ser Phe His Ser Gly
                355                 360                 365

Tyr Ser Gly Leu Val Ala Thr Val Ser Gly Ser Gln Gln Thr Leu Val
                370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Asp Gly Gly Gly Asn Asp Gly Gly
                420                 425

<210> SEQ ID NO 20
<211> LENGTH: 429
<212> TYPE: PRT
<213> ORGANISM: Artificial Sequence
<220> FEATURE:
<223> OTHER INFORMATION: Mature protein sequence of pMS1104

<400> SEQUENCE: 20

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
                20                  25                  30

Tyr Asn Trp Tyr Asn Ile Leu Arg Gln Lys Ala Ser Thr Ile Ala Ala
                35                  40                  45

Asp Gly Phe Ser Ala Ile Trp Met Pro Val Pro Trp Arg Asp Phe Ser
            50                  55                  60

Ser Trp Thr Asp Gly Asp Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
                100                 105                 110

Val Val Pro Asn His Met Asn Arg Phe Tyr Pro Asp Lys Glu Ile Asn
                115                 120                 125

Leu Pro Ala Gly Gln Arg Phe Trp Arg Asn Asp Cys Pro Asp Pro Gly
            130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Phe Arg Phe
                180                 185                 190

Asp Phe Val Arg Gly Tyr Ala Pro Glu Arg Val Asp Ser Trp Met Ser
                195                 200                 205

Asp Ser Ala Asp Ser Ser Phe Cys Val Gly Glu Leu Trp Lys Glu Pro
            210                 215                 220

Ser Glu Tyr Pro Pro Trp Asp Trp Arg Asn Thr Ala Ser Trp Gln Gln
225                 230                 235                 240
```

```
Ile Ile Lys Asp Trp Ser Asp Arg Ala Lys Cys Pro Val Phe Asp Phe
            245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
290                 295                 300

Gln His Lys Trp Pro Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
            325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
            355                 360                 365

Tyr Ser Gly Leu Val Ala Thr Val Ser Gly Ser Gln Gln Thr Leu Val
            370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
            405                 410                 415

Arg Ser Gly Ser Gly Asp Gly Gly Asn Asp Gly Gly
            420                 425

<210> SEQ ID NO 21
<211> LENGTH: 429
<212> TYPE: PRT
<213> ORGANISM: Artificial Sequence
<220> FEATURE:
<223> OTHER INFORMATION: Mature protein sequence of pMS1153

<400> SEQUENCE: 21

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Asp Lys Ser Gly Gly Gly Glu Gly Tyr Phe Trp
65                  70                  75                  80

His Asp Phe Asn Lys Asn Gly Leu Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175
```

```
Glu Phe Thr Asn Leu Arg Ser Gly Tyr Gly Ala Gly Gly Phe Arg Phe
                180                 185                 190

Asp Phe Val Arg Gly Tyr Ala Pro Glu Arg Val Asp Ser Trp Met Ser
            195                 200                 205

Asp Ser Ala Asp Ser Ser Phe Cys Val Gly Glu Leu Trp Lys Glu Pro
        210                 215                 220

Ser Glu Tyr Pro Pro Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Lys Trp Pro Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
            420                 425

<210> SEQ ID NO 22
<211> LENGTH: 429
<212> TYPE: PRT
<213> ORGANISM: Artificial Sequence
<220> FEATURE:
<223> OTHER INFORMATION: Mature protein sequence of pMS1286

<400> SEQUENCE: 22

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
                20                  25                  30

Tyr Asn Trp Tyr Asn Ile Leu Arg Gln Gln Ala Ser Thr Ile Ala Ala
            35                  40                  45

Asp Gly Phe Ser Ala Ile Trp Met Pro Val Pro Trp Arg Asp Phe Ser
        50                  55                  60

Ser Trp Thr Asp Gly Asp Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
```

Leu Pro Ala Gly Gln Arg Phe Trp Arg Asn Asp Cys Pro Asp Pro Gly
            130                 135                 140

Asn Gly Pro Asn Asp Cys Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Phe Arg Phe
            180                 185                 190

Asp Phe Val Arg Gly Tyr Ala Pro Glu Arg Val Asp Ser Trp Met Ser
            195                 200                 205

Asp Ser Ala Asp Ser Ser Phe Cys Val Gly Glu Leu Trp Lys Glu Pro
210                 215                 220

Ser Glu Tyr Pro Pro Trp Asp Trp Arg Asn Arg Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
            290                 295                 300

Gln His Lys Trp Pro Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
            355                 360                 365

Tyr Ser Gly Leu Val Ala Thr Val Ser Gly Ser Gln Gln Thr Leu Val
370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
            420                 425

<210> SEQ ID NO 23
<211> LENGTH: 429
<212> TYPE: PRT
<213> ORGANISM: Artificial Sequence
<220> FEATURE:
<223> OTHER INFORMATION: Mature protein sequence of pMS1284

<400> SEQUENCE: 23

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

```
Ser Trp Thr Asp Gly Asp Lys Ser Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Glu Pro
    210                 215                 220

Ser Glu Tyr Pro Pro Trp Asp Trp Arg Asn Arg Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Lys Trp Pro Leu Pro Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
            420                 425
```

<210> SEQ ID NO 24
<211> LENGTH: 429
<212> TYPE: PRT
<213> ORGANISM: Artificial Sequence
<220> FEATURE:
<223> OTHER INFORMATION: Mature protein sequence of pMS1290

<400> SEQUENCE: 24

-continued

```
Asp Gln Ala Gly Lys Ser Pro Ala Gly Val Arg Tyr His Gly Gly Asp
1               5                   10                  15
Glu Ile Ile Leu Gln Gly Phe His Trp Asn Val Val Arg Glu Ala Pro
            20                  25                  30
Tyr Asn Trp Tyr Asn Ile Leu Arg Gln Gln Ala Ser Thr Ile Ala Ala
        35                  40                  45
Asp Gly Phe Ser Ala Ile Trp Met Pro Val Pro Trp Arg Asp Phe Ser
    50                  55                  60
Ser Trp Thr Asp Gly Asp Lys Ser Gly Gly Glu Gly Tyr Phe Trp
65                  70                  75                  80
His Asp Phe Asn Lys Asn Gly Arg Tyr Gly Ser Asp Ala Gln Leu Arg
                85                  90                  95
Gln Ala Ala Gly Ala Leu Gly Ala Gly Val Lys Val Leu Tyr Asp
            100                 105                 110
Val Val Pro Asn His Met Asn Arg Phe Tyr Pro Asp Lys Glu Ile Asn
        115                 120                 125
Leu Pro Ala Gly Gln Arg Phe Trp Arg Asn Asp Cys Pro Asp Pro Gly
    130                 135                 140
Asn Gly Pro Asn Asp Cys Asp Asp Gly Asp Arg Phe Leu Gly Gly Glu
145                 150                 155                 160
Ala Asp Leu Asn Thr Gly His Pro Gln Ile Tyr Gly Met Phe Arg Asp
                165                 170                 175
Glu Phe Thr Asn Leu Arg Ser Gly Tyr Gly Ala Gly Gly Phe Arg Phe
            180                 185                 190
Asp Phe Val Arg Gly Tyr Ala Pro Glu Arg Val Asp Ser Trp Met Ser
        195                 200                 205
Asp Ser Ala Asp Ser Ser Phe Cys Val Gly Glu Leu Trp Lys Glu Pro
    210                 215                 220
Ser Glu Tyr Pro Pro Trp Asp Trp Arg Asn Lys Ala Ser Trp Gln Gln
225                 230                 235                 240
Ile Ile Lys Asp Trp Ser Asp Arg Ala Lys Cys Pro Val Phe Asp Phe
                245                 250                 255
Ala Leu Lys Glu Arg Met Gln Asn Gly Ser Val Ala Asp Trp Lys His
            260                 265                 270
Gly Leu Asn Gly Asn Pro Asp Pro Arg Trp Arg Glu Val Ala Val Thr
        275                 280                 285
Phe Val Asp Asn His Asp Thr Gly Tyr Ser Pro Gly Gln Asn Gly Gly
    290                 295                 300
Gln His Lys Trp Pro Leu Gln Asp Gly Leu Ile Arg Gln Ala Tyr Ala
305                 310                 315                 320
Tyr Ile Leu Thr Ser Pro Gly Thr Pro Val Val Tyr Trp Pro His Met
                325                 330                 335
Tyr Asp Trp Gly Tyr Gly Asp Phe Ile Arg Gln Leu Ile Gln Val Arg
            340                 345                 350
Arg Thr Ala Gly Val Arg Ala Asp Ser Ala Ile Ser Phe His Ser Gly
        355                 360                 365
Tyr Ser Gly Leu Val Ala Thr Val Ser Gly Ser Gln Gln Thr Leu Val
    370                 375                 380
Val Ala Leu Asn Ser Asp Leu Ala Asn Pro Gly Gln Val Ala Ser Gly
385                 390                 395                 400
Ser Phe Ser Glu Ala Val Asn Ala Ser Asn Gly Gln Val Arg Val Trp
                405                 410                 415
Arg Ser Gly Ser Gly Asp Gly Gly Asn Asp Gly Gly
            420                 425
```

<210> SEQ ID NO 25
<211> LENGTH: 429
<212> TYPE: PRT
<213> ORGANISM: Artificial Sequence
<220> FEATURE:
<223> OTHER INFORMATION: Mature protein sequence of pMS1484

<400> SEQUENCE: 25

```
Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Asp Lys Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Leu Trp Met Ser
        195                 200                 205

Asp Ser Ala Asp Ser Ser Phe Cys Val Gly Glu Leu Trp Lys Glu Pro
    210                 215                 220

Ser Glu Tyr Pro Pro Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Lys Trp Pro Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365
```

```
Tyr Ser Gly Leu Val Ala Thr Val Ser Gly Ser Gln Gln Thr Leu Val
        370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
                420                 425

<210> SEQ ID NO 26
<211> LENGTH: 429
<212> TYPE: PRT
<213> ORGANISM: Artificial Sequence
<220> FEATURE:
<223> OTHER INFORMATION: Mature protein sequence of pMS1579

<400> SEQUENCE: 26

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
                20                  25                  30

Tyr Asn Trp Tyr Asn Ile Leu Arg Gln Gln Ala Ser Thr Ile Ala Ala
            35                  40                  45

Asp Gly Phe Ser Ala Ile Trp Met Pro Val Pro Trp Arg Asp Phe Ser
        50                  55                  60

Ser Trp Thr Asp Gly Asp Lys Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
                100                 105                 110

Val Val Pro Asn His Met Asn Arg Phe Tyr Pro Asp Lys Glu Ile Asn
                115                 120                 125

Leu Pro Ala Gly Gln Arg Phe Trp Arg Asn Asp Cys Pro Asp Pro Gly
        130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
                180                 185                 190

Asp Phe Val Arg Gly Tyr Ala Pro Glu Arg Val Asp Ser Trp Met Ser
                195                 200                 205

Asp Ser Ala Asp Ser Ser Phe Cys Val Gly Glu Leu Trp Lys Glu Pro
        210                 215                 220

Ser Glu Tyr Pro Pro Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
                260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
        290                 295                 300

Gln His Lys Trp Pro Leu Gln Asp Gly Leu Ile Arg Gln Ala Tyr Ala
```

```
                305                 310                 315                 320
Tyr Ile Leu Thr Ser Pro Gly Thr Pro Val Tyr Trp Pro His Met
                    325                 330                 335

Tyr Asp Trp Gly Tyr Gly Asp Phe Ile Arg Gln Leu Ile Gln Val Arg
                340                 345                 350

Arg Thr Ala Gly Val Arg Ala Asp Ser Ala Ile Ser Phe His Ser Gly
                355                 360                 365

Tyr Ser Gly Leu Val Ala Thr Val Ser Gly Ser Gln Gln Thr Leu Val
            370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Glu Asn Gly Gln Val Arg Val Trp
                    405                 410                 415

Arg Ser Gly Ser Gly Asp Gly Gly Asn Asp Gly Gly
                420                 425

<210> SEQ ID NO 27
<211> LENGTH: 429
<212> TYPE: PRT
<213> ORGANISM: Artificial Sequence
<220> FEATURE:
<223> OTHER INFORMATION: Mature protein sequence of pMS1105

<400> SEQUENCE: 27

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Lys Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Asp Lys Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ser Pro
    210                 215                 220

Ser Glu Tyr Pro Pro Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255
```

```
Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
            290                 295                 300

Gln His Lys Trp Pro Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
            325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
            355                 360                 365

Tyr Ser Gly Leu Val Ala Thr Val Ser Gly Ser Gln Gln Thr Leu Val
            370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
            405                 410                 415

Arg Ser Gly Ser Gly Asp Gly Gly Asn Asp Gly Gly
            420                 425
```

<210> SEQ ID NO 28
<211> LENGTH: 429
<212> TYPE: PRT
<213> ORGANISM: Artificial Sequence
<220> FEATURE:
<223> OTHER INFORMATION: Mature protein sequence of pMS1723

<400> SEQUENCE: 28

```
Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Lys Ala Ser Thr Ile Ala Ala
            35                  40                  45

Asp Gly Phe Ser Ala Ile Trp Met Pro Val Pro Trp Arg Asp Phe Ser
    50                  55                  60

Ser Trp Thr Asp Gly Asp Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
            115                 120                 125

Leu Pro Ala Gly Gln Arg Phe Trp Arg Asn Asp Cys Pro Asp Pro Gly
130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190
```

-continued

```
Asp Phe Val Arg Gly Tyr Ala Pro Glu Arg Val Asp Ser Trp Met Ser
        195                 200                 205
Asp Ser Ala Asp Ser Ser Phe Cys Val Gly Glu Leu Trp Lys Ser Pro
210                 215                 220
Ser Glu Tyr Pro Pro Trp Asp Trp Arg Asn Thr Ala Ser Trp Gln Gln
225                 230                 235                 240
Ile Ile Lys Asp Trp Ser Asp Arg Ala Lys Cys Pro Val Phe Asp Phe
                245                 250                 255
Ala Leu Lys Glu Arg Met Gln Asn Gly Ser Val Ala Asp Trp Lys His
            260                 265                 270
Gly Leu Asn Gly Asn Pro Asp Pro Arg Trp Arg Glu Val Ala Val Thr
        275                 280                 285
Phe Val Asp Asn His Asp Thr Gly Tyr Ser Pro Gly Gln Asn Gly Gly
    290                 295                 300
Gln His Lys Trp Pro Leu Gln Asp Gly Leu Ile Arg Gln Ala Tyr Ala
305                 310                 315                 320
Tyr Ile Leu Thr Ser Pro Gly Thr Pro Val Val Tyr Trp Pro His Met
                325                 330                 335
Tyr Asp Trp Gly Tyr Gly Asp Phe Ile Arg Gln Leu Ile Gln Val Arg
            340                 345                 350
Arg Thr Ala Gly Val Arg Ala Asp Ser Ala Ile Ser Phe His Ser Gly
        355                 360                 365
Tyr Ser Gly Leu Val Ala Thr Val Ser Gly Ser Gln Gln Thr Leu Val
    370                 375                 380
Val Ala Leu Asn Ser Asp Leu Asp Asn Pro Gly Gln Val Ala Ser Gly
385                 390                 395                 400
Ser Phe Ser Glu Ala Val Asn Ala Ser Asn Gly Gln Val Arg Val Trp
                405                 410                 415
Arg Ser Gly Ser Gly Asp Gly Gly Asn Asp Gly Gly
            420                 425

<210> SEQ ID NO 29
<211> LENGTH: 429
<212> TYPE: PRT
<213> ORGANISM: Artificial Sequence
<220> FEATURE:
<223> OTHER INFORMATION: Mature protein sequence of pMS2104

<400> SEQUENCE: 29

Asp Gln Ala Gly Lys Ser Pro Ala Gly Val Arg Tyr His Gly Gly Asp
1               5                   10                  15
Glu Ile Ile Leu Gln Gly Phe His Trp Asn Val Val Arg Glu Ala Pro
                20                  25                  30
Tyr Asn Trp Tyr Asn Ile Leu Arg Gln Lys Ala Ser Thr Ile Ala Ala
            35                  40                  45
Asp Gly Phe Ser Ala Ile Trp Met Pro Val Pro Trp Arg Asp Phe Ser
        50                  55                  60
Ser Trp Thr Asp Gly Asp Lys Ser Gly Gly Glu Gly Tyr Phe Trp
65                  70                  75                  80
His Asp Phe Asn Lys Asn Gly Leu Tyr Gly Ser Asp Ala Gln Leu Arg
                85                  90                  95
Gln Ala Ala Gly Ala Leu Gly Gly Ala Gly Val Lys Val Leu Tyr Asp
            100                 105                 110
Val Val Pro Asn His Met Asn Arg Phe Tyr Pro Asp Lys Glu Ile Asn
        115                 120                 125
Leu Pro Ala Gly Gln Arg Phe Trp Arg Asn Asp Cys Pro Asp Pro Gly
```

```
            130                 135                 140
Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
            195                 200                 205

Asp Ser Ala Asp Ser Ser Phe Cys Val Gly Glu Leu Trp Lys Ala Pro
210                 215                 220

Ser Glu Tyr Pro Pro Trp Asp Trp Arg Asn Arg Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
290                 295                 300

Gln His Lys Trp Pro Leu Pro Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
            355                 360                 365

Tyr Ser Gly Leu Val Ala Thr Val Ser Gly Ser Gln Gln Thr Leu Val
            370                 375                 380

Val Ala Leu Asn Ser Asp Leu Asp Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly
            420                 425

<210> SEQ ID NO 30
<211> LENGTH: 429
<212> TYPE: PRT
<213> ORGANISM: Artificial Sequence
<220> FEATURE:
<223> OTHER INFORMATION: Mature protein sequence of pMS2138

<400> SEQUENCE: 30

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Lys Ala Ser Thr Ile Ala Ala
        35                  40                  45

Asp Gly Phe Ser Ala Ile Trp Met Pro Val Pro Trp Arg Asp Phe Ser
50                  55                  60

Ser Trp Thr Asp Gly Asp Lys Ser Gly Gly Gly Glu Gly Tyr Phe Trp
65                  70                  75                  80
```

His Asp Phe Asn Lys Asn Gly Leu Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
        115                 120                 125

Leu Pro Ala Gly Gln Arg Phe Trp Arg Asn Asp Cys Pro Asp Pro Gly
130                 135                 140

Asn Gly Pro Asn Asp Cys Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Leu Trp Met Ser
        195                 200                 205

Asp Ser Ala Asp Ser Ser Phe Cys Val Gly Glu Leu Trp Lys Ser Pro
210                 215                 220

Ser Glu Tyr Pro Pro Trp Asp Trp Arg Asn Arg Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
290                 295                 300

Gln His Lys Trp Pro Leu Pro Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
370                 375                 380

Val Ala Leu Asn Ser Asp Leu Asp Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
            420                 425

<210> SEQ ID NO 31
<211> LENGTH: 429
<212> TYPE: PRT
<213> ORGANISM: Artificial Sequence
<220> FEATURE:
<223> OTHER INFORMATION: Mature protein sequence of pMS2124

<400> SEQUENCE: 31

Asp Gln Ala Gly Lys Ser Pro Ala Gly Val Arg Tyr His Gly Gly Asp
1               5                   10                  15

-continued

```
Glu Ile Ile Leu Gln Gly Phe His Trp Asn Val Val Arg Glu Ala Pro
         20                  25                  30

Tyr Asn Trp Tyr Asn Ile Leu Arg Gln Lys Ala Ser Thr Ile Ala Ala
             35                  40                  45

Asp Gly Phe Ser Ala Ile Trp Met Pro Val Pro Trp Arg Asp Phe Ser
 50                  55                  60

Ser Trp Thr Asp Gly Asp Lys Ser Gly Gly Glu Gly Tyr Phe Trp
 65                  70                  75                  80

His Asp Phe Asn Lys Asn Gly Leu Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
            115                 120                 125

Leu Pro Ala Gly Gln Arg Phe Trp Arg Asn Asp Cys Pro Asp Pro Gly
        130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Leu Trp Met Ser
        195                 200                 205

Asp Ser Ala Asp Ser Ser Phe Cys Val Gly Glu Leu Trp Lys Lys Pro
    210                 215                 220

Ser Glu Tyr Pro Pro Trp Asp Trp Arg Asn Arg Ala Ser Trp Gln Glu
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Lys Trp Pro Leu Pro Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Asp Asn Pro Gly Gln Val Ala Ser Gly
385                 390                 395                 400

Ser Phe Ser Glu Ala Val Asn Ala Glu Asn Gly Gln Val Arg Val Trp
                405                 410                 415

Arg Ser Gly Ser Gly Asp Gly Gly Gly Asn Asp Gly Gly
            420                 425
```

<210> SEQ ID NO 32

```
<211> LENGTH: 429
<212> TYPE: PRT
<213> ORGANISM: Artificial Sequence
<220> FEATURE:
<223> OTHER INFORMATION: Mature protein sequence of pMS2177

<400> SEQUENCE: 32

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Gln Trp Tyr Asn Ile Leu Arg Gln Lys Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Asp Lys Ser Gly Gly Glu Gly Tyr Phe Trp
65                  70                  75                  80

His Asp Phe Asn Lys Asn Gly Leu Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Leu Trp Met Ser
        195                 200                 205

Asp Ser Ala Asp Ser Ser Phe Cys Val Gly Glu Leu Trp Lys Lys Pro
    210                 215                 220

Ser Glu Tyr Pro Pro Trp Asp Trp Arg Asn Arg Ala Ser Trp Gln Glu
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Lys Trp Pro Leu Pro Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380
```

Val Ala Leu Asn Ser Asp Leu Asp Asn Pro Gly Gln Val Ala Ser Gly
385                 390                 395                 400

Ser Phe Ser Glu Ala Val Asn Ala Glu Asn Gly Gln Val Arg Val Trp
            405                 410                 415

Arg Ser Gly Ser Gly Asp Gly Gly Asn Asp Gly Gly
            420                 425

<210> SEQ ID NO 33
<211> LENGTH: 429
<212> TYPE: PRT
<213> ORGANISM: Artificial Sequence
<220> FEATURE:
<223> OTHER INFORMATION: Mature protein sequence of pMS2178

<400> SEQUENCE: 33

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
                20                  25                  30

Tyr Asn Trp Tyr Asn Ile Leu Arg Gln Lys Ala Ser Thr Ile Ala Ala
            35                  40                  45

Asp Gly Phe Ser Ala Ile Trp Met Pro Val Pro Trp Arg Asp Phe Ser
50                  55                  60

Ser Trp Thr Asp Gly Asp Lys Ser Gly Gly Glu Gly Tyr Phe Trp
65                  70                  75                  80

His Asp Phe Asn Lys Asn Gly Leu Tyr Gly Ser Asp Ala Gln Leu Arg
                85                  90                  95

Gln Ala Ala Gln Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
            115                 120                 125

Leu Pro Ala Gly Gln Arg Phe Trp Arg Asn Asp Cys Pro Asp Pro Gly
130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Leu Trp Met Ser
            195                 200                 205

Asp Ser Ala Asp Ser Ser Phe Cys Val Gly Glu Leu Trp Lys Lys Pro
210                 215                 220

Ser Glu Tyr Pro Pro Trp Asp Trp Arg Asn Arg Ala Ser Trp Gln Glu
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
            290                 295                 300

Gln His Lys Trp Pro Leu Pro Asp Gly Leu Ile Arg Gln Ala Tyr Ala
305                 310                 315                 320

Tyr Ile Leu Thr Ser Pro Gly Thr Pro Val Val Tyr Trp Pro His Met

```
                        325                 330                 335
Tyr Asp Trp Gly Tyr Gly Asp Phe Ile Arg Gln Leu Ile Gln Val Arg
                340                 345                 350

Arg Thr Ala Gly Val Arg Ala Asp Ser Ala Ile Ser Phe His Ser Gly
            355                 360                 365

Tyr Ser Gly Leu Val Ala Thr Val Ser Gly Ser Gln Gln Thr Leu Val
        370                 375                 380

Val Ala Leu Asn Ser Asp Leu Asp Asn Pro Gly Gln Val Ala Ser Gly
385                 390                 395                 400

Ser Phe Ser Glu Ala Val Asn Ala Glu Asn Gly Gln Val Arg Val Trp
                405                 410                 415

Arg Ser Gly Ser Gly Asp Gly Gly Asn Asp Gly Gly
            420                 425

<210> SEQ ID NO 34
<211> LENGTH: 429
<212> TYPE: PRT
<213> ORGANISM: Artificial Sequence
<220> FEATURE:
<223> OTHER INFORMATION: Mature protein sequence of pMS2118

<400> SEQUENCE: 34

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
                20                  25                  30

Tyr Asn Trp Tyr Asn Ile Leu Arg Gln Lys Ala Ser Thr Ile Ala Ala
            35                  40                  45

Asp Gly Phe Ser Ala Ile Trp Met Pro Val Pro Trp Arg Asp Phe Ser
        50                  55                  60

Ser Trp Thr Asp Gly Asp Lys Ser Gly Gly Gly Glu Gly Tyr Phe Trp
65                  70                  75                  80

His Asp Phe Asn Lys Asn Gly Leu Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Leu Trp Met Ser
        195                 200                 205

Asp Ser Ala Asp Ser Ser Phe Cys Val Gly Glu Leu Trp Lys Ser Pro
    210                 215                 220

Ser Glu Tyr Pro Pro Trp Asp Trp Arg Asn Arg Ala Ser Trp Gln Glu
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270
```

-continued

```
Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
            290                 295                 300

Gln His Lys Trp Pro Leu Pro Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
            355                 360                 365

Tyr Ser Gly Leu Val Ala Thr Val Ser Gly Ser Gln Gln Thr Leu Val
        370                 375                 380

Val Ala Leu Asn Ser Asp Leu Asp Asn Pro Gly Gln Val Ala Ser Gly
385                 390                 395                 400

Ser Phe Ser Glu Ala Val Asn Ala Glu Asn Gly Gln Val Arg Val Trp
                405                 410                 415

Arg Ser Gly Ser Gly Asp Gly Gly Asn Asp Gly Gly
            420                 425
```

<210> SEQ ID NO 35
<211> LENGTH: 11
<212> TYPE: PRT
<213> ORGANISM: Artificial Sequence
<220> FEATURE:
<223> OTHER INFORMATION: Linker Sequence

<400> SEQUENCE: 35

```
Gly Ser Gly Asp Gly Gly Gly Asn Asp Gly Gly
1               5                   10
```

<210> SEQ ID NO 36
<211> LENGTH: 101
<212> TYPE: PRT
<213> ORGANISM: Artificial Sequence
<220> FEATURE:
<223> OTHER INFORMATION: Sequence of PS4 SBD

<400> SEQUENCE: 36

```
Glu Gly Gly Leu Val Asn Val Asn Phe Arg Cys Asp Asn Gly Val Thr
1               5                   10                  15

Gln Met Gly Asp Ser Val Tyr Ala Val Gly Asn Val Ser Gln Leu Gly
            20                  25                  30

Asn Trp Ser Pro Ala Ser Ala Val Arg Leu Thr Asp Thr Ser Ser Tyr
        35                  40                  45

Pro Thr Trp Lys Gly Ser Ile Ala Leu Pro Asp Gly Gln Asn Val Glu
    50                  55                  60

Trp Lys Cys Leu Ile Arg Asn Glu Ala Asp Ala Thr Leu Val Arg Gln
65                  70                  75                  80

Trp Gln Ser Gly Gly Asn Asn Gln Val Gln Ala Ala Gly Ala Ser
                85                  90                  95

Thr Ser Gly Ser Phe
            100
```

<210> SEQ ID NO 37
<211> LENGTH: 13
<212> TYPE: PRT
<213> ORGANISM: Artificial Sequence

```
<220> FEATURE:
<223> OTHER INFORMATION: Amino acid residues in position 13-26 of
      SEQ ID NO: 1

<400> SEQUENCE: 37

His Gly Gly Asp Glu Ile Ile Leu Gln Phe His Trp Asn
1               5                   10

<210> SEQ ID NO 38
<211> LENGTH: 18
<212> TYPE: PRT
<213> ORGANISM: Artificial Sequence
<220> FEATURE:
<223> OTHER INFORMATION: Subsequence variant motif of amino acids
      49-66 of D1
<220> FEATURE:
<221> NAME/KEY: MISC_FEATURE
<222> LOCATION: (4)..(4)
<223> OTHER INFORMATION: Xaa in position 4 is S or T
<220> FEATURE:
<221> NAME/KEY: MISC_FEATURE
<222> LOCATION: (8)..(8)
<223> OTHER INFORMATION: Xaa in position 8 is M or L
<220> FEATURE:
<221> NAME/KEY: MISC_FEATURE
<222> LOCATION: (10)..(10)
<223> OTHER INFORMATION: Xaa in position 10 is any natural occurring
      amino acid residue
<220> FEATURE:
<221> NAME/KEY: MISC_FEATURE
<222> LOCATION: (15)..(15)
<223> OTHER INFORMATION: Xaa in position 15 is any natural occurring
      amino acid residue

<400> SEQUENCE: 38

Asp Gly Phe Xaa Ala Ile Trp Xaa Pro Xaa Pro Trp Arg Asp Xaa Ser
1               5                   10                  15

Ser Trp

<210> SEQ ID NO 39
<211> LENGTH: 7
<212> TYPE: PRT
<213> ORGANISM: Artificial Sequence
<220> FEATURE:
<223> OTHER INFORMATION: Subsequence of amino acids 74-80 of
      SEQ ID NO:1

<400> SEQUENCE: 39

Gly Gly Glu Gly Tyr Phe Trp
1               5

<210> SEQ ID NO 40
<211> LENGTH: 4
<212> TYPE: PRT
<213> ORGANISM: Artificial Sequence
<220> FEATURE:
<223> OTHER INFORMATION: Subsequence of amino acids 114-117 of
      SEQ ID NO:1

<400> SEQUENCE: 40

Val Pro Asn His
1

<210> SEQ ID NO 41
<211> LENGTH: 5
<212> TYPE: PRT
<213> ORGANISM: Artificial Sequence
<220> FEATURE:
<223> OTHER INFORMATION: Subsequence of amino acids 150-154 of
      SEQ ID NO:1
```

```
<400> SEQUENCE: 41

Cys Asp Asp Gly Asp
1               5

<210> SEQ ID NO 42
<211> LENGTH: 11
<212> TYPE: PRT
<213> ORGANISM: Artificial Sequence
<220> FEATURE:
<223> OTHER INFORMATION: Artificial subsequence

<400> SEQUENCE: 42

Ala Gly Gly Phe Arg Phe Asp Phe Val Arg Gly
1               5                   10

<210> SEQ ID NO 43
<211> LENGTH: 4
<212> TYPE: PRT
<213> ORGANISM: Artificial Sequence
<220> FEATURE:
<223> OTHER INFORMATION: Subsequence of amino acids 256-259 of
      SEQ ID NO:1

<400> SEQUENCE: 43

Phe Ala Leu Lys
1

<210> SEQ ID NO 44
<211> LENGTH: 13
<212> TYPE: PRT
<213> ORGANISM: Artificial Sequence
<220> FEATURE:
<223> OTHER INFORMATION: Subsequence of amino acids 282-294 of
      SEQ ID NO:1

<400> SEQUENCE: 44

Trp Arg Glu Val Ala Val Thr Phe Val Asp Asn His Asp
1               5                   10

<210> SEQ ID NO 45
<211> LENGTH: 5
<212> TYPE: PRT
<213> ORGANISM: Artificial Sequence
<220> FEATURE:
<223> OTHER INFORMATION: Subsequence of amino acids 296-300 of
      SEQ ID NO:1

<400> SEQUENCE: 45

Gly Tyr Ser Pro Gly
1               5

<210> SEQ ID NO 46
<211> LENGTH: 3
<212> TYPE: PRT
<213> ORGANISM: Artificial Sequence
<220> FEATURE:
<223> OTHER INFORMATION: Subsequence of amino acids 304-306 of
      SEQ ID NO:1

<400> SEQUENCE: 46

Gly Gln His
1

<210> SEQ ID NO 47
<211> LENGTH: 5
<212> TYPE: PRT
<213> ORGANISM: Artificial Sequence
<220> FEATURE:
```

<223> OTHER INFORMATION: Subsequence of amino acids 318-322 of
      SEQ ID NO:1

<400> SEQUENCE: 47

Ala Tyr Ala Tyr Ile
1               5

<210> SEQ ID NO 48
<211> LENGTH: 5
<212> TYPE: PRT
<213> ORGANISM: Artificial Sequence
<220> FEATURE:
<223> OTHER INFORMATION: Subsequence of amino acids 325-329 of
      SEQ ID NO:1

<400> SEQUENCE: 48

Ser Pro Gly Thr Pro
1               5

<210> SEQ ID NO 49
<211> LENGTH: 3
<212> TYPE: PRT
<213> ORGANISM: Artificial Sequence
<220> FEATURE:
<223> OTHER INFORMATION: Subsequence of amino acids 331-333 of
      SEQ ID NO:1

<400> SEQUENCE: 49

Val Tyr Trp
1

<210> SEQ ID NO 50
<211> LENGTH: 6
<212> TYPE: PRT
<213> ORGANISM: Artificial Sequence
<220> FEATURE:
<223> OTHER INFORMATION: Subsequence of amino acids 335-340 of
      SEQ ID NO:1

<400> SEQUENCE: 50

His Met Tyr Asp Trp Gly
1               5

<210> SEQ ID NO 51
<211> LENGTH: 686
<212> TYPE: PRT
<213> ORGANISM: Artificial Sequence
<220> FEATURE:
<223> OTHER INFORMATION: AA sequence of Novamyl

<400> SEQUENCE: 51

Ser Ser Ser Ala Ser Val Lys Gly Asp Val Ile Tyr Gln Ile Ile
1               5                   10                  15

Asp Arg Phe Tyr Asp Gly Asp Thr Thr Asn Asn Pro Ala Lys Ser
                20                  25                  30

Tyr Gly Leu Tyr Asp Pro Thr Lys Ser Lys Trp Lys Met Tyr Trp Gly
            35                  40                  45

Gly Asp Leu Glu Gly Val Arg Gln Lys Leu Pro Tyr Leu Lys Gln Leu
        50                  55                  60

Gly Val Thr Thr Ile Trp Leu Ser Pro Val Leu Asp Asn Leu Asp Thr
65                  70                  75                  80

Leu Ala Gly Thr Asp Asn Thr Gly Tyr His Gly Tyr Trp Thr Arg Asp
                85                  90                  95

Phe Lys Gln Ile Glu Glu His Phe Gly Asn Trp Thr Thr Phe Asp Thr
            100                 105                 110

```
Leu Val Asn Asp Ala His Gln Asn Gly Ile Lys Val Ile Val Asp Phe
            115                 120                 125

Val Pro Asn His Ser Thr Pro Phe Lys Ala Asn Asp Ser Thr Phe Ala
130                 135                 140

Glu Gly Gly Ala Leu Tyr Asn Asn Gly Thr Tyr Met Gly Asn Tyr Phe
145                 150                 155                 160

Asp Asp Ala Thr Lys Gly Tyr Phe His His Asn Gly Asp Ile Ser Asn
            165                 170                 175

Trp Asp Asp Arg Tyr Glu Ala Gln Trp Lys Asn Phe Thr Asp Pro Ala
            180                 185                 190

Gly Phe Ser Leu Ala Asp Leu Ser Gln Glu Asn Gly Thr Ile Ala Gln
            195                 200                 205

Tyr Leu Thr Asp Ala Ala Val Gln Leu Val Ala His Gly Ala Asp Gly
            210                 215                 220

Leu Arg Ile Asp Ala Val Lys His Phe Asn Ser Gly Phe Ser Lys Ser
225                 230                 235                 240

Leu Ala Asp Lys Leu Tyr Gln Lys Lys Asp Ile Phe Leu Val Gly Glu
            245                 250                 255

Trp Tyr Gly Asp Asp Pro Gly Thr Ala Asn His Leu Glu Lys Val Arg
            260                 265                 270

Tyr Ala Asn Asn Ser Gly Val Asn Val Leu Asp Phe Asp Leu Asn Thr
            275                 280                 285

Val Ile Arg Asn Val Phe Gly Thr Phe Thr Gln Thr Met Tyr Asp Leu
            290                 295                 300

Asn Asn Met Val Asn Gln Thr Gly Asn Glu Tyr Lys Tyr Lys Glu Asn
305                 310                 315                 320

Leu Ile Thr Phe Ile Asp Asn His Asp Met Ser Arg Phe Leu Ser Val
            325                 330                 335

Asn Ser Asn Lys Ala Asn Leu His Gln Ala Leu Ala Phe Ile Leu Thr
            340                 345                 350

Ser Arg Gly Thr Pro Ser Ile Tyr Tyr Gly Thr Glu Gln Tyr Met Ala
            355                 360                 365

Gly Gly Asn Asp Pro Tyr Asn Arg Gly Met Met Pro Ala Phe Asp Thr
            370                 375                 380

Thr Thr Thr Ala Phe Lys Glu Val Ser Thr Leu Ala Gly Leu Arg Arg
385                 390                 395                 400

Asn Asn Ala Ala Ile Gln Tyr Gly Thr Thr Thr Gln Arg Trp Ile Asn
            405                 410                 415

Asn Asp Val Tyr Ile Tyr Glu Arg Lys Phe Phe Asn Asp Val Val Leu
            420                 425                 430

Val Ala Ile Asn Arg Asn Thr Gln Ser Ser Tyr Ser Ile Ser Gly Leu
            435                 440                 445

Gln Thr Ala Leu Pro Asn Gly Ser Tyr Ala Asp Tyr Leu Ser Gly Leu
450                 455                 460

Leu Gly Gly Asn Gly Ile Ser Val Ser Asn Gly Ser Val Ala Ser Phe
465                 470                 475                 480

Thr Leu Ala Pro Gly Ala Val Ser Val Trp Gln Tyr Ser Thr Ser Ala
            485                 490                 495

Ser Ala Pro Gln Ile Gly Ser Val Ala Pro Asn Met Gly Ile Pro Gly
            500                 505                 510

Asn Val Val Thr Ile Asp Gly Lys Gly Phe Gly Thr Thr Gln Gly Thr
            515                 520                 525

Val Thr Phe Gly Gly Val Thr Ala Thr Val Lys Ser Trp Thr Ser Asn
```

```
                530              535              540
Arg Ile Glu Val Tyr Val Pro Asn Met Ala Ala Gly Leu Thr Asp Val
545                  550                  555                  560

Lys Val Thr Ala Gly Gly Val Ser Ser Asn Leu Tyr Ser Tyr Asn Ile
                565                  570                  575

Leu Ser Gly Thr Gln Thr Ser Val Val Phe Thr Val Lys Ser Ala Pro
            580                  585                  590

Pro Thr Asn Leu Gly Asp Lys Ile Tyr Leu Thr Gly Asn Ile Pro Glu
        595                  600                  605

Leu Gly Asn Trp Ser Thr Asp Thr Ser Gly Ala Val Asn Asn Ala Gln
    610                  615                  620

Gly Pro Leu Leu Ala Pro Asn Tyr Pro Asp Trp Phe Tyr Val Phe Ser
625                  630                  635                  640

Val Pro Ala Gly Lys Thr Ile Gln Phe Lys Phe Ile Lys Arg Ala
                645                  650                  655

Asp Gly Thr Ile Gln Trp Glu Asn Gly Ser Asn His Val Ala Thr Thr
            660                  665                  670

Pro Thr Gly Ala Thr Gly Asn Ile Thr Val Thr Trp Gln Asn
        675                  680                  685

<210> SEQ ID NO 52
<211> LENGTH: 1290
<212> TYPE: DNA
<213> ORGANISM: Artificial Sequence
<220> FEATURE:
<223> OTHER INFORMATION: Nucleotide sequence of pMS382

<400> SEQUENCE: 52
gatcaagcag gaaaaagccc ggcaggcgtc agatatcatg gcggcgatga atcatccttt      60
cagggctttc attggaacgt cgtcagagaa gcgccgtata actggtataa catcctgaga     120
caacaagcga gcacaattgc cgctgatggc ttttccgcaa tctggatgcc ggttccgtgg     180
agagatttta gcagctggac ggatggagat aaaagcggag gcggcgaagg atatttttgg     240
catgacttta caaaaacgg ccgctatgga agcgatgctc aactgagaca agcagcagga     300
gcacttggag gagcaggagt caaagtcctg tacgatgtcg tcccgaacca tatgaaccgc     360
ttttatccgg acaagaaat caatctgccg gcaggccaaa gattttggag aaacgattgc     420
ccggacccgg gaaatggacc gaatgattgc gatgatggcg atagatttct gggcggcgaa     480
gcggatctga atacaggcca tccgcaaatc tatggcatgt tcggacgaa atttacgaat     540 ctgagaagcg gatatggagc gggcggattt cgctttgatt ttgtcagagg ctatgccccg     600
gaaagagttg atagctggat gagcgattca gcggatagca gcttttgcgt cggcgaactt     660
tggaaagaac cgagcgaata tccgccgtgg gattggagaa atacagcgag ctggcagcag     720
atcatcaaag attggagcga tagagcaaaa tgcccggtct ttgactttgc cctgaaagaa     780
cgcatgcaaa atggaagcgt cgccgattgg aaacatggcc tgaacggaaa tccggacccg     840
agatggagag aagtcgccgt cacgtttgtc gataaccatg acacaggata tagcccggga     900
caaaatggag acaacataa atggccgctt caagatggcc ttatcagaca ggcgtatgcc     960
tatatcctta catcaccggg aacaccggtt gtttattggc cgcatatgta tgattgggc    1020 tatggcgatt catccggcca actgatccag gttagaagaa cagcaggagt cagagcggat    1080
agcgccatta gctttcatag cggctatagc ggacttgtcg ctacagttag cggcagccaa    1140
caaacactgg tcgtcgccct gaatagcgat ctggcaaatc cggacaagt tgctagcggc    1200 agctttagcg aagcagtcaa tgccagcaat ggccaagtca gagtctggag aagcggaagc    1260
```

```
ggagatggag gaggaaatga cggaggataa                                     1290

<210> SEQ ID NO 53
<211> LENGTH: 38
<212> TYPE: DNA
<213> ORGANISM: Artificial Sequence
<220> FEATURE:
<223> OTHER INFORMATION: DNA primer

<400> SEQUENCE: 53
gtataacatc ctgagacaaa aagcgagcac aattgccg                            38

<210> SEQ ID NO 54
<211> LENGTH: 37
<212> TYPE: DNA
<213> ORGANISM: Artificial Sequence
<220> FEATURE:
<223> OTHER INFORMATION: DNA primer

<400> SEQUENCE: 54
gtataacatc ctgagacaaa acgcgagcac aattgcc                             37

<210> SEQ ID NO 55
<211> LENGTH: 41
<212> TYPE: DNA
<213> ORGANISM: Artificial Sequence
<220> FEATURE:
<223> OTHER INFORMATION: DNA primer

<400> SEQUENCE: 55
gcatgacttt aacaaaaacg gcctgtatgg aagcgatgct c                        41

<210> SEQ ID NO 56
<211> LENGTH: 45
<212> TYPE: DNA
<213> ORGANISM: Artificial Sequence
<220> FEATURE:
<223> OTHER INFORMATION: DNA primer

<400> SEQUENCE: 56
ggcatgactt taacaaaaac ggctattatg aagcgatgc tcaac                     45

<210> SEQ ID NO 57
<211> LENGTH: 45
<212> TYPE: DNA
<213> ORGANISM: Artificial Sequence
<220> FEATURE:
<223> OTHER INFORMATION: DNA primer

<400> SEQUENCE: 57
ggcatgactt taacaaaaac ggcaaatatg aagcgatgc tcaac                     45

<210> SEQ ID NO 58
<211> LENGTH: 39
<212> TYPE: DNA
<213> ORGANISM: Artificial Sequence
<220> FEATURE:
<223> OTHER INFORMATION: DNA primer

<400> SEQUENCE: 58
gccccggaaa gagttgatct gtggatgagc gattcagcg                           39

<210> SEQ ID NO 59
<211> LENGTH: 32
<212> TYPE: DNA
<213> ORGANISM: Artificial Sequence
```

```
<220> FEATURE:
<223> OTHER INFORMATION: DNA primer

<400> SEQUENCE: 59
gtgggattgg agaaatagag cgagctggca gc                                    32

<210> SEQ ID NO 60
<211> LENGTH: 32
<212> TYPE: DNA
<213> ORGANISM: Artificial Sequence
<220> FEATURE:
<223> OTHER INFORMATION: DNA primer

<400> SEQUENCE: 60
gtgggattgg agaaataaag cgagctggca gc                                    32

<210> SEQ ID NO 61
<211> LENGTH: 37
<212> TYPE: DNA
<213> ORGANISM: Artificial Sequence
<220> FEATURE:
<223> OTHER INFORMATION: DNA primer

<400> SEQUENCE: 61
gccgtgggat tggagaaatc atgcgagctg gcagcag                               37

<210> SEQ ID NO 62
<211> LENGTH: 36
<212> TYPE: DNA
<213> ORGANISM: Artificial Sequence
<220> FEATURE:
<223> OTHER INFORMATION: DNA primer

<400> SEQUENCE: 62
ccgtgggatt ggagaaatca ggcgagctgg cagcag                                36

<210> SEQ ID NO 63
<211> LENGTH: 36
<212> TYPE: DNA
<213> ORGANISM: Artificial Sequence
<220> FEATURE:
<223> OTHER INFORMATION: DNA primer

<400> SEQUENCE: 63
cgctccaatc tttgatgatt tcctgccagc tcgctg                                36

<210> SEQ ID NO 64
<211> LENGTH: 36
<212> TYPE: DNA
<213> ORGANISM: Artificial Sequence
<220> FEATURE:
<223> OTHER INFORMATION: DNA primer

<400> SEQUENCE: 64
cagcgagctg gcaggatatc atcaaagatt ggagcg                                36

<210> SEQ ID NO 65
<211> LENGTH: 39
<212> TYPE: DNA
<213> ORGANISM: Artificial Sequence
<220> FEATURE:
<223> OTHER INFORMATION: DNA primer

<400> SEQUENCE: 65
caacataaat ggccgcttcc ggatggcctt atcagacag                             39
```

```
<210> SEQ ID NO 66
<211> LENGTH: 38
<212> TYPE: DNA
<213> ORGANISM: Artificial Sequence
<220> FEATURE:
<223> OTHER INFORMATION: DNA primer

<400> SEQUENCE: 66
gccctgaata gcgatctgga taatccggga caagttgc                            38

<210> SEQ ID NO 67
<211> LENGTH: 42
<212> TYPE: DNA
<213> ORGANISM: Artificial Sequence
<220> FEATURE:
<223> OTHER INFORMATION: DNA primer

<400> SEQUENCE: 67
cgccctgaat agcgatctgt ataatccggg acaagttgct ag                       42

<210> SEQ ID NO 68
<211> LENGTH: 40
<212> TYPE: DNA
<213> ORGANISM: Artificial Sequence
<220> FEATURE:
<223> OTHER INFORMATION: DNA primer

<400> SEQUENCE: 68
gcgaagcagt caatgccgaa aatggccaag tcagagtctg                          40

<210> SEQ ID NO 69
<211> LENGTH: 43
<212> TYPE: DNA
<213> ORGANISM: Artificial Sequence
<220> FEATURE:
<223> OTHER INFORMATION: DNA primer

<400> SEQUENCE: 69
catcaaagat tggagcgatc atgcaaaatg cccggtcttt gac                      43

<210> SEQ ID NO 70
<211> LENGTH: 37
<212> TYPE: DNA
<213> ORGANISM: Artificial Sequence
<220> FEATURE:
<223> OTHER INFORMATION: DNA primer

<400> SEQUENCE: 70
cgcatgcaaa atggaacggt cgccgattgg aaacatg                             37

<210> SEQ ID NO 71
<211> LENGTH: 25
<212> TYPE: DNA
<213> ORGANISM: Artificial Sequence
<220> FEATURE:
<223> OTHER INFORMATION: DNA primer

<400> SEQUENCE: 71
ctaccgtcga tggcagccag cagac                                          25

<210> SEQ ID NO 72
<211> LENGTH: 25
<212> TYPE: DNA
<213> ORGANISM: Artificial Sequence
<220> FEATURE:
<223> OTHER INFORMATION: DNA primer
```

```
<400> SEQUENCE: 72
ctacagttga tggcagccaa caaac                                              25
```

AMYLASE POLYPEPTIDES

RELATED APPLICATIONS AND INCORPORATION BY REFERENCE

This application is a continuation-in-part application of international patent application Serial No. PCT/EP2010/056913 filed May 19, 2010, which published as PCT Publication No. WO 2010/133644 on Nov. 25, 2010, which claims benefit of U.S. provisional patent application Ser. No. 61/179,525 filed May 19, 2009 and European patent application Serial No. 09160655.8 filed May 19, 2009.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

This invention relates to polypeptides, specifically amylase polypeptides and nucleic acids encoding these, and their uses e.g. as non-maltogenic exoamylases in producing food or feed products.

BACKGROUND OF THE INVENTION

Improved amylases can ameliorate problems inherent in certain processes, such as in conversion of vegetable starches or baking.

Crystallisation of amylopectin takes place in starch granules days after baking, which leads to increased firmness of bread and causes bread staling. When bread stales, bread loses crumb softness and crumb moisture. As a result, crumbs become less elastic, and bread develops a leathery crust.

Enzymatic hydrolysis (by amylases, for example) of amylopectin side chains can reduce crystallization and increase anti-staling. Crystallization depends upon the length of amylopectin side chains: the longer the side chains, the greater the crystallization. Most starch granules are composed of a mixture of two polymers: amylopectin and amylose, of which about 75% is amylopectin. Amylopectin is a very large, branched molecule consisting of chains of α-D-glucopyranosyl units joined by (1-4) linkages, where the chains are attached by α-D-(1-6) linkages to form branches. Amylose is a linear chain of (1-4) linked α-D-glucopyranosyl units having few α-D-(1-6) branches.

Baking of farinaceous bread products such as white bread, bread made from bolted rye flour and wheat flour and rolls is accomplished by baking the bread dough at oven temperatures in the range of from 180 to 250° C. for about 15 to 60 minutes. During the baking process a steep temperature gradient (200 to 120° C.) prevails over the outer dough layers where the crust of the baked product is developed. However, due to steam, the temperature in the crumb is only about 100° C. at the end of the baking process. Above temperatures of about 85° C., enzyme inactivation can take place and the enzyme will have no anti-staling properties. Only thermostable amylases, thus, are able to modify starch efficiently during baking.

Endoamylase activity can negatively affect the quality of the final bread product by producing a sticky or gummy crumb due to the accumulation of branched dextrins. Exoamylase activity is preferred, because it accomplishes the desired modification of starch that leads to retardation of staling, with fewer of the negative effects associated with endo-amylase activity. Reduction of endoamylase activity can lead to greater exospecifity, which can reduce branched dextrins and produce a higher quality bread.

The conversion of vegetable starches, especially corn starch, to ethanol is a rapidly expanding industry. Maltotetraose (G4 or DP4) syrup is one of many commercially important products derived from enzymatic treatment of starch. The conversion of vegetable starches, especially cornstarch, to maltotetraose and lower sugars, such as glucose or maltose, is a rapidly expanding industry.

The current process consists of two sequential enzyme-catalyzed steps that result in the production of glucose or maltose. Yeast can then be used to ferment the glucose to ethanol.

The first enzyme-catalyzed step is starch liquefaction. Typically, a starch suspension is gelatinized by rapid heating to 85° C. or more. α-Amylases (EC 3.2.1.1) are used to degrade the viscous liquefact to maltodextrins. α-amylases are endohydrolases that catalyze the random cleavage of internal α-1,4-D glucosidic bonds. As α-amylases break down the starch, the viscosity decreases. Because liquefaction typically is conducted at high temperatures, thermostable α-amylases, such as an α-amylase from Bacillus sp., are preferred for this step.

The maltodextrins produced in this manner generally cannot be fermented by yeast to form alcohol. A second enzyme-catalyzed saccharification step thus is required to break down the maltodextrins. Glucoamylases and/or maltogenic α-amylases commonly are used to catalyze the hydrolysis of non-reducing ends of the maltodextrins formed after liquefaction, releasing D-glucose, maltose and isomaltose. Debranching enzymes, such as pullulanases, can be used to aid saccharification. Saccharification typically takes place under acidic conditions at elevated temperatures, e.g., 60° C., pH 4.3.

G4 (also referred to as DP4) syrup has a number of advantageous properties compared to sucrose syrups. For example, partially replacing sucrose with G4 syrup in a food reduces the food's sweetness without affecting its taste or flavor. G4 syrup has high moisture retention in foods and exhibits less deleterious Maillard reaction products because of its lower glucose and maltose content. G4 syrup also has higher viscosity than sucrose, thus improving food texture. G4 syrup depresses the freezing point of water less than sucrose or high fructose syrup, so G4 syrup can better control the freezing points of frozen foods. After ingestion, G4 syrup also affects osmotic pressure less than sucrose. Together, these qualities make G4 syrup ideally suited as an ingredient in foods and medical products. G4 syrup is useful in other industries, as well. For example, G4 syrup imparts gloss and can be used advantageously as a paper sizer. See, e.g., Kimura et al., "Maltotetraose, a new saccharide of tertiary property," Starch 42: 151-57 (1990).

One of the yeasts used to produce ethanol is *Saccharomyces cerevisiae*. *S. cerevisiae* contains α-glucosidase that has been shown to utilize mono-, di-, and tri-saccharides as substrates. Yoon et al., Carbohydrate Res. 338: 1127-32 (2003). The ability of *S. cerevisiae* to utilize tri-saccharides can be improved by $Mg^{2+}$ supplementation and over-expression of AGT1 permease (Stambuck et al., *Lett. Appl. Microbiol.* 43: 370-76 (2006)), over-expression of MTT1 and MTT1alt to increase maltotriose uptake (Dietvorst et al., *Yeast* 22: 775-88 (2005)), or expression of the maltase MAL32 on the cell surface (Dietvorst et al., *Yeast* 24: 27-38 (2007)). The saccharification step could be omitted altogether, if the liquefaction step produced sufficient levels of mono-, di-, or tri-saccharides and *S. cerevisiae* or its genetically modified variants were used for the fermentation step.

*Pseudomonas saccharophila* expresses a maltotetraose-forming maltotetraohydrolase (EC 3.2.1.60; G4-forming amylase; G4-amylase). The nucleotide sequence of the *P. saccharophila* gene encoding PS4 has been determined. Zhou et al., "Nucleotide sequence of the maltotetraohydrolase gene from *Pseudomonas saccharophila*," *FEBS Lett.* 255: 37-41 (1989); GenBank Acc. No. X16732. PS4 is expressed as a precursor protein with an N-terminal 21-residue signal peptide. The mature form of PS4, as set forth in SEQ ID NO: 10, contains 530 amino acid residues with a catalytic domain at the N terminus and a starch binding domain at the C-terminus. PS4 displays both endo- and exo-α-amylase activity. Endo-α-amylase activity is useful for decreasing the viscosity of gelatinized starch, and exo-α-amylase activity is useful for breaking down maltodextrins to smaller saccharides.

Citation or identification of any document in this application is not an admission that such document is available as prior art to the present invention.

SUMMARY OF THE INVENTION

This invention relates to polypeptides, specifically amylase polypeptides and nucleic acids encoding these, and their uses e.g. as non-maltogenic exoamylases in producing food products. The amylases of the present invention have been engineered to have more beneficial qualities. Specifically, the amylases of the current invention show an altered exospecifity and/or altered thermostability. In particular, the polypeptides may be derived from polypeptides having non-maltogenic exoamylase activity, in particular, glucan 1,4-alpha-maltotetraohydrolase (EC 3.2.1.60) activity. In one aspect, the polypeptides as defined herein may have an improved anti-staling effect compared to the amylase of SEQ ID NO: 1.

In another aspect, the polypeptides as defined herein may have an improved thermostability compared to the amylase of SEQ ID NO: 1.

A variant polypeptide as set out in the claims is provided. In a further aspect, the use of such a variant polypeptide, including in and as food additives, food products, bakery products, improver compositions, feed products including animal feeds, etc as set out in the claims, is provided. In yet a further aspect, nucleic acids which encode and which relate to variant polypeptides, as set out in the claims, are provided. Methods for producing such variant polypeptides, as well as other aspects, are also set out in the claims.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DISCLOSURE OF THE INVENTION

Figure 1:
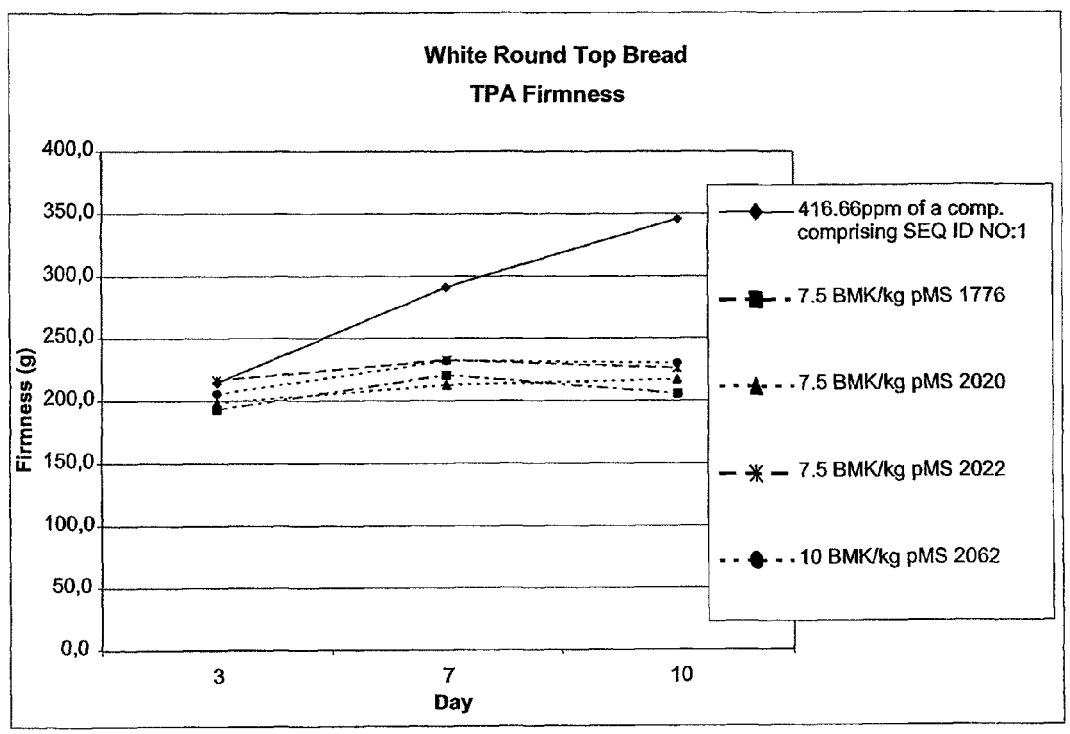
FIG. 1 shows firmness development of bread baked with pMS1776 (SEQ ID NO: 12), pMS2020 (SEQ ID NO: 14), pMS2022 (SEQ ID NO: 15) and pMS2062 (SEQ ID NO: 16) compared to bread baked with a composition comprising SEQ ID NO: 1.

In accordance with this detailed description, the following abbreviations and definitions apply. It should be noted that as used herein, the singular forms "a," "an," and "the" include plural referents unless the context clearly dictates otherwise. Thus, for example, reference to "an enzyme" includes a plurality of such enzymes, and reference to "the formulation" includes reference to one or more formulations and equivalents thereof known to those skilled in the art, and so forth.

In one aspect, a polypeptide having amylase activity comprising an amino acid sequence having
   a) at least 65% sequence identity to the amino acid sequence of SEQ ID NO: 1, and wherein the polypeptide comprises one or more amino acid substitutions at the following positions: 88 or 205, and/or
   b) at least 78% sequence identity to the amino acid sequence of SEQ ID NO: 1, and wherein the polypeptide comprises one or more amino acid substitutions at the following positions: 16, 48, 97, 105, 235, 240, 248, 266, 311, 347, 350, 362, 364, 369, 393, 395, 396, 400, 401, 403, 412 or 409, and/or
   c) at least 78% sequence identity to the amino acid sequence of SEQ ID NO: 1, and wherein the polypeptide comprises one or more of the following amino acid substitutions: 42K/A/V/N/I/H/F, 34Q, 100Q/K/N/R, 272D, 392 K/D/E/Y/N/Q/R/T/G or 399C/H, and/or
   d) at least 95% sequence identity to the amino acid sequence of SEQ ID NO: 1, and wherein the polypeptide comprises one or more amino acid substitutions at the following positions: 44, 96, 204, 354 or 377, and/or
   e) at least 95% sequence identity to the amino acid sequence of SEQ ID NO: 1, and wherein the polypeptide comprises the following amino acid substitution: 392S with reference to the position numbering of the sequence shown as SEQ ID NO: 1, is provided.

In one aspect, a polypeptide having amylase activity comprising an amino acid sequence having at least 65% sequence identity to the amino acid sequence of SEQ ID NO: 1, and wherein the polypeptide comprises one or more amino acid substitutions at the following positions: 88, or 205 and/or one or more of the following amino acid substitutions: 42K, 235H/K/R, 240E, 392 K/D/E/Y or 409E with reference to the position numbering of the sequence shown as SEQ ID NO: 1, is provided.

The present invention also encompasses the use of polypeptides having a degree of sequence identity or sequence homology with amino acid sequence(s) defined herein or with a polypeptide having the specific properties defined herein. The present invention encompasses, in particular, peptides having a degree of sequence identity with SEQ ID NO: 1, defined below, or homologues thereof. Here, the term "homologue" means an entity having sequence identity with the subject amino acid sequences or the subject nucleotide sequences, where the subject amino acid sequence preferably is SEQ ID NO: 1 and the subject nucleotide sequence preferably is SEQ ID NO: 52.

In one aspect, the homologous amino acid sequence and/or nucleotide sequence should provide and/or encode a polypeptide which retains the functional activity and/or enhances the activity of a polypeptide of SEQ ID NO: 1 or SEQ ID NO: 10, preferably the activity of a polypeptide of SEQ ID NO: 1.

In the present context, a homologous sequence is taken to include an amino acid sequence which may be at least 65%, 70%, 75%, 78%, at least 80%, at least 85%, at least 90%, at least 95%, at least 96%, at least 97%, at least 98% or at least 99%, identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

Sequence identity comparisons can be conducted by eye, or more usually, with the aid of readily available sequence comparison programs. These commercially available computer programs use complex comparison algorithms to align two or more sequences that best reflect the evolutionary events that might have led to the difference(s) between the two or more sequences. Therefore, these algorithms operate with a scoring system rewarding alignment of identical or similar amino acids and penalising the insertion of gaps, gap extensions and alignment of non-similar amino acids. The scoring system of the comparison algorithms include:

i) assignment of a penalty score each time a gap is inserted (gap penalty score),
ii) assignment of a penalty score each time an existing gap is extended with an extra position (extension penalty score),
iii) assignment of high scores upon alignment of identical amino acids, and
iv) assignment of variable scores upon alignment of non-identical amino acids.

Most alignment programs allow the gap penalties to be modified. However, it is preferred to use the default values when using such software for sequence comparisons.

The scores given for alignment of non-identical amino acids are assigned according to a scoring matrix also called a substitution matrix. The scores provided in such substitution matrices are reflecting the fact that the likelihood of one amino acid being substituted with another during evolution varies and depends on the physical/chemical nature of the amino acid to be substituted. For example, the likelihood of a polar amino acid being substituted with another polar amino acid is higher compared to being substituted with a hydrophobic amino acid. Therefore, the scoring matrix will assign the highest score for identical amino acids, lower score for non-identical but similar amino acids and even lower score for non-identical non-similar amino acids. The most frequently used scoring matrices are the PAM matrices (Dayhoff et al. (1978), Jones et al. (1992)), the BLOSUM matrices (Henikoff and Henikoff (1992)) and the Gonnet matrix (Gonnet et al. (1992)).

Suitable computer programs for carrying out such an alignment include, but are not limited to, Vector NTI (Invitrogen Corp.) and the ClustalV, ClustalW and ClustalW2 programs (Higgins D G & Sharp P M (1988), Higgins et al. (1992), Thompson et al. (1994), Larkin et al. (2007). A selection of different alignment tools are available from the ExPASy Proteomics server at www.expasy.org. Another example of software that can perform sequence alignment is BLAST (Basic Local Alignment Search Tool), which is available from the webpage of National Center for Biotechnology Information which can currently be found at http://www.ncbi.nlm.nih.gov/ and which was firstly described in Altschul et al. (1990) J. Mol. Biol. 215; 403-410.

Once the software has produced an alignment, it is possible to calculate % similarity and % sequence identity. The software typically does this as part of the sequence comparison and generates a numerical result.

In one embodiment, it is preferred to use the ClustalW software for performing sequence alignments. Preferably, alignment with ClustalW is performed with the following parameters for pairwise alignment:

| | |
|---|---|
| Substitution matrix: | Gonnet 250 |
| Gap open penalty: | 20 |
| Gap extension penalty: | 0.2 |
| Gap end penalty: | None |

ClustalW2 is for example made available on the internet by the European Bioinformatics Institute at the EMBL-EBI webpage www.ebi.ac.uk under tools—sequence analysis—ClustalW2. Currently, the exact address of the ClustalW2 tool is www.ebi.ac.uk/Tools/clustalw2.

In another embodiment, it is preferred to use the program Align X in Vector NTI (Invitrogen) for performing sequence alignments. In one embodiment, Exp10 has is used with the default settings:

| | |
|---|---|
| Gap opening penalty: | 10 |
| Gap extension penalty: | 0.05 |
| Gapseparation penalty range: | 8 |
| Score matrix: | blosum62mt2 |

Thus, the present invention also encompasses the use of variants, homologues and derivatives of any amino acid sequence of a protein or polypeptide as defined herein, particularly those of SEQ ID NO: 1 or those of SEQ ID NO: 2, 4, 6, 8 or 10 defined below.

The sequences, particularly those of variants, homologues and derivatives of SEQ ID NO: 1, may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

The present invention also encompasses conservative substitution (substitution and replacement are both used herein to mean the interchange of an existing amino acid residue, with an alternative residue) that may occur i.e. like-for-like substitution such as basic for basic, acidic for acidic, polar for polar etc. Non-conservative substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Conservative substitutions that may be made are, for example within the groups of basic amino acids (Arginine, Lysine and Histidine), acidic amino acids (glutamic acid and aspartic acid), aliphatic amino acids (Alanine, Valine, Leucine, Isoleucine), polar amino acids (Glutamine, Asparagine, Serine, Threonine), aromatic amino acids (Phenylalanine, Tryptophan and Tyrosine), hydroxyl amino acids (Serine, Threonine), large amino acids (Phenylalanine and Tryptophan) and small amino acids (Glycine, Alanine).

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ϵ-amino caproic acid#, 7-amino heptanoic acid*, L-methionine sulfone#*, L-norleucine*, L-norvaline*, p-nitro-L-phenylalanine*, L-hydroxyproline, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid and L-Phe (4-benzyl)*. The notation * has been utilised for the purpose of the discussion above (relating to homologous or non-conservative substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al. (1992), Horwell D C. (1995).

In one embodiment, the variant polypeptide is a *Pseudomonas saccharophila* amylase (PS4) variant having the sequence shown in SEQ ID NO: 1 and having at least at least 65%, at least 70%, at least 75%, at least 78%, at least 80%, at least 85%, at least 90%, at least 95%, at least 96%, at least 97%, at least 98% or at least 99% amino acid sequence identity therewith.

In one aspect, preferably the sequence used in the present invention is in a purified form. The term "purified" means that a given component is present at a high level. The component is desirably the predominant active component present in a composition.

Unless defined otherwise, all technical and scientific terms used herein have the same meaning as commonly understood by one of ordinary skill in the art. The following terms are provided below.

"Amylase" means an enzyme that is, among other things, capable of catalyzing the degradation of starch. An endo-acting amylase activity cleaves α-D-(1→4) O-glycosidic linkages within the starch molecule in a random fashion. In contrast, an exo-acting amylolytic activity cleaves a starch molecule from the non-reducing end of the substrate. "Endo-acting amylase activity," "endo-activity," "endo-specific activity," and "endo-specificity" are synonymous, when the terms refer to the variant polypeptides as defined in the claims. The same is true for the corresponding terms for exo-activity.

"maltotetraose-forming maltotetrahydrolase; EC 3.2.1.60; G4-forming amylase; G4-amylase and glucan 1,4-alpha-maltotetrahydrolase" may be used interchangeably.

In the present context, "PS4" is used to designate the maltotetrahydrolase from *Pseudomonas saccharophila*.

A "variant" or "variants" refers to either polypeptides or nucleic acids. The term "variant" may be used interchangeably with the term "mutant." Variants include insertions, substitutions, transversions, truncations, and/or inversions at one or more locations in the amino acid or nucleotide sequence, respectively. The phrases "variant polypeptide", "polypeptide", "variant" and "variant enzyme" mean a polypeptide/protein that has an amino acid sequence that has been modified from the amino acid sequence of SEQ ID NO: 1. The variant polypeptides include a polypeptide having a certain percent, e.g., 65%, 66%, 68%, 70%, 72%, 74%, 76%, 78%, 80%, 85%, 90%, 91%, 92%, 93%, 94%, 95%, 96%, 97%, 98%, or 99%, of sequence identity with SEQ ID NO: 1. As used herein, "parent enzymes," "parent sequence," "parent polypeptide" mean enzymes and polypeptides from which the variant polypeptides are based, e.g., SEQ ID NO: 1. A "parent nucleic acid" means a nucleic acid sequence encoding the parent polypeptide. The signal sequence of a "variant" may be the same (such as SEQ ID NO: 11) or may differ from the signal sequence of the wild-type PS4. A variant may be expressed as a fusion protein containing a heterologous polypeptide.

For example, the variant can comprise a signal peptide of another protein or a sequence designed to aid identification or purification of the expressed fusion protein, such as a His-Tag sequence.

To describe the various variants that are contemplated to be encompassed by the present disclosure, the following nomenclature will be adopted for ease of reference. Where the substitution includes a number and a letter, e.g., 141P, then this refers to {position according to the numbering system/substituted amino acid}. Accordingly, for example, the substitution of an amino acid to proline in position 141 is designated as 141P. Where the substitution includes a letter, a number, and a letter, e.g., A141P, then this refers to {original amino acid/position according to the numbering system/substituted amino acid}. Accordingly, for example, the substitution of alanine with proline in position 141 is designated as A141P.

Where two or more substitutions are possible at a particular position, this will be designated by contiguous letters, which may optionally be separated by slash marks "/", e.g., G303ED or G303E/D.

Position(s) and amino acid substitutions referred to herein are listed with reference to the corresponding position and the corresponding amino acid of SEQ ID NO: 1. Equivalent positions in another sequence may be found by aligning this sequence with SEQ ID NO:1 to find an alignment with the highest percent identity and thereafter determining which amino acid aligns to correspond with an amino acid of a specific position of SEQ ID NO:1. Such alignment and use of one sequence as a first reference is simply a matter of routine for one of ordinary skill in the art.

"Variant nucleic acids" can include sequences that are complementary to sequences that are capable of hybridizing to the nucleotide sequences presented herein, in particular to SEQ ID NO:52. For example, a variant sequence is complementary to sequences capable of hybridizing under stringent conditions, e.g., 50° C. and 0.2×SSC (1×SSC=0.15 M NaCl, 0.015 M sodium citrate, pH 7.0), to the nucleotide sequences presented herein, in particular to SEQ ID NO:52 (pMS 382 DNA) More particularly, the term variant encompasses sequences that are complementary to sequences that are capable of hybridizing under highly stringent conditions, e.g., 65° C. and 0.1×SSC, to the nucleotide sequences presented herein, in particular to SEQ ID NO:52 (pMS 382 DNA) The melting point (Tm) of a variant nucleic acid may be about 1, 2, or 3° C. lower than the Tm of the wild-type nucleic acid. The variant nucleic acids include a polynucleotide having a certain percent, e.g., 80%, 85%, 90%, 95%, or 99%, of sequence identity with the nucleic acid encoding SEQ ID NO: 1.

As used herein, the term "expression" refers to the process by which a polypeptide is produced based on the nucleic acid sequence of a gene. The process includes both transcription and translation.

"Isolated" means that the sequence is at least substantially free from at least one other component that the sequence is naturally associated and found in nature, e.g., genomic sequences.

"Purified" means that the material is in a relatively pure state, e.g., at least about 90% pure, at least about 95% pure, or at least about 98% pure.

"Thermostable" means the enzyme retains activity after exposure to elevated temperatures. The thermostability of an enzyme may be measured by its half-life ($t_{1/2}$), where half of the enzyme activity is lost by the half-life. The half-life value is calculated under defined conditions by measuring the residual amylase activity. To determine the half-life of the enzyme, the sample is heated to the test temperature for 1-10 min, and activity is measured using a standard assay for amylase activity, such as the Betamyl® assay (Megazyme, Ireland).

As used herein, "optimum pH" means the pH at which the variant polypeptides disclosed herein displays the activity in a standard assay for amylase activity, measured over a range of pH's.

As used herein, "polypeptide" is used interchangeably with the terms "amino acid sequence", "enzyme", "peptide" and/or "protein." As used herein, "nucleotide sequence" or "nucleic acid sequence" refers to an oligonucleotide sequence or polynucleotide sequence and variants, homologues, fragments and derivatives thereof. The nucleotide sequence may be of genomic, synthetic or recombinant origin and may be double-stranded or single-stranded, whether representing the sense or anti-sense strand. As used herein, the term "nucleotide sequence" includes genomic DNA, cDNA, synthetic DNA, and RNA.

"Homologue" means an entity having a certain degree of identity or "homology" with the subject amino acid sequences and the subject nucleotide sequences. A "homologous sequence" includes a polynucleotide or a polypeptide having a certain percent, e.g., 80%, 85%, 90%, 95%, or 99%, of sequence identity with another sequence. Percent identity means that, when aligned, that percentage of bases or amino acid residues are the same when comparing the two sequences. Amino acid sequences are not identical, where an amino acid is substituted, deleted, or added compared to the subject sequence. The percent sequence identity typically is measured with respect to the mature sequence of the subject protein, i.e., following removal of a signal sequence, for example. Typically, homologues will comprise the same active site residues as the subject amino acid sequence. Homologues also retain amylase activity, although the homologue may have different enzymatic properties than the wild-type PS4.

As used herein, "hybridization" includes the process by which a strand of nucleic acid joins with a complementary strand through base pairing, as well as the process of amplification as carried out in polymerase chain reaction (PCR) technologies. The variant nucleic acid may exist as single- or double-stranded DNA or RNA, an RNA/DNA heteroduplex or an RNA/DNA copolymer. As used herein, "copolymer" refers to a single nucleic acid strand that comprises both ribonucleotides and deoxyribonucleotides. The variant nucleic acid may be codon-optimized to further increase expression.

As used herein, a "synthetic" compound is produced by in vitro chemical or enzymatic synthesis. It includes, but is not limited to, variant nucleic acids made with optimal codon usage for host organisms, such as a yeast cell host or other expression hosts of choice.

As used herein, "transformed cell" includes cells, including both bacterial and fungal cells, which have been transformed by use of recombinant DNA techniques. Transformation typically occurs by insertion of one or more nucleotide sequences into a cell. The inserted nucleotide sequence may be a heterologous nucleotide sequence, i.e., is a sequence that is not natural to the cell that is to be transformed, such as a fusion protein.

As used herein, "operably linked" means that the described components are in a relationship permitting them to function in their intended manner. For example, a regulatory sequence operably linked to a coding sequence is ligated in such a way that expression of the coding sequence is achieved under condition compatible with the control sequences.

As used herein the term "starch" refers to any material comprised of the complex polysaccharide carbohydrates of plants, such as corn, comprised of amylose and amylopectin with the formula $(C_6H_{10}O_5)_x$, where X can be any number. The term "granular starch" refers to raw, i.e., uncooked starch, e.g., starch that has not been subject to gelatinization.

The term "liquefaction" refers to the stage in starch conversion in which gelatinized starch is hydrolyzed to give low molecular weight soluble dextrins. As used herein the term "saccharification" refers to enzymatic conversion of starch to glucose. The term "degree of polymerization" (DP) refers to the number (n) of anhydroglucopyranose units in a given saccharide. Examples of DP1 are the monosaccharides glucose and fructose. Examples of DP2 are the disaccharides maltose and sucrose.

As used herein the term "dry solids content" (ds) refers to the total solids of a slurry in a dry weight percent basis. The term "slurry" refers to an aqueous mixture containing insoluble solids.

The phrase "simultaneous saccharification and fermentation (SSF)" refers to a process in the production of biochemicals in which a microbial organism, such as an ethanol producing microorganism and at least one enzyme, such as PS4 or a variant thereof, are present during the same process step. SSF refers to the contemporaneous hydrolysis of granular starch substrates to saccharides and the fermentation of the saccharides into alcohol, for example, in the same reactor vessel.

As used herein "ethanologenic microorganism" refers to a microorganism with the ability to convert a sugar or oligosaccharide to ethanol.

The following abbreviations apply unless indicated otherwise:

| | |
|---|---|
| ADA | azodicarbonamide |
| cDNA | complementary DNA |
| CGTase | cyclodextrin glucanotransferase |
| DEAE | diethylamino ethanol |
| dH$_2$O | deionized water |
| DNA | deoxyribonucleic acid |
| ds-DNA | double-stranded DNA |
| EC | enzyme commission for enzyme classification |
| FGSC | Fungal Genetics Stock Center |
| G121F | glycine (G) residue at position 121 of SEQ ID NO: 2 is replaced with a phenylalanine (F) residue, where amino acids are designated by single letter abbreviations commonly known in the art |
| HPLC | High Performance Liquid Chromatography |
| mRNA | messenger ribonucleic acid |
| PCR | polymerase chain reaction |
| PDB | Protein Database Base |
| PEG | polyethyleneglycol |
| ppm | parts per million |
| PS4 | *P. saccharophila* G4 forming amylase |
| RT-PCR | reverse transcriptase polymerase chain reaction |
| SAS | *P. saccharophila* G4 forming amylase |
| SDS-PAGE | sodium dodecyl sulfate-polyacrylamide gel electrophoresis |
| 1X SSC | 0.15M NaCl, 0.015M sodium citrate, pH 7.0 |
| SSF | simultaneous saccharification and fermentation |
| t$\frac{1}{2}$ | half life |
| Tm | melting temperature (° C.) at which 50% of the subject protein is melted |
| ΔTm | ° C. increase in the Tm |
| w/v | weight/volume |
| w/w | weight/weight |

In one aspect, a polypeptide having a substitution at one or more positions which effect an altered property, which may be any combination of altered exospecificity, endospecifity or altered thermostability, or an altered handling property, relative to SEQ ID NO: 1, is provided. Such variant polypeptides are also referred to in this document for convenience as "variant polypeptide", "polypeptide variant" or "variant". In one aspect, the polypeptides as defined herein have an improved antistaling effect compared to the amylase of SEQ ID NO: 1. In another aspect, the polypeptides as defined herein have an improved thermostability compared to the amylase of SEQ ID NO: 1. In highly preferred embodiments, they have the added advantage of higher thermostability, or higher exoamylase activity or higher pH stability, or any combination.

In one aspect, the variants as defined herein exhibit enzyme activity. In one aspect, the variant polypeptides comprise amylase activity. In a further aspect, the variant polypeptides comprise exoamylase activity. In a further aspect, the variant polypeptides exhibit non-maltogenic exoamylase activity. In one aspect, the variants as defined herein are derivable form *Pseudomonas saccharophila* α-amylase (PS4). In one aspect, the variants as defined herein are a maltotetraose-forming maltotetrahydrolase, also called EC 3.2.1.60; G4-forming amylase; G4-amylase or glucan 1,4-alpha-maltotetrahydrolase.

Compositions, including food additives, food products, bakery products, improver compositions, feed products including animal feeds, etc comprising such variant polypeptides as defined herein, such as those which have non-maltogenic exoamylase activity, as well as methods of making and using such polypeptides and the compositions, are provided herein.

As noted above, the variant polypeptides may comprise one or more improved handling properties, preferably improved baking properties. Thus, the variant polypeptides are such that the food products so treated have one or more of (preferably all of) a lower firmness, a higher resilience, a higher cohesiveness, a lower crumbliness or a higher foldability. Such improved handling or baking properties exhibited by the variant polypeptides are described in further detail below.

Furthermore a treatment of food products, particularly doughs and bakery products with such polypeptides, and such that the food products exhibit the desired qualities set out above, is provided.

Further is provided other uses of the variants described herein and compositions comprising these variants, such as in the preparation of detergents, as sweeteners, syrups, etc. The compositions include the polypeptide together with at least one other component. In particular, food or feed additives comprising the polypeptides, are provided.

An isolated and/or purified polypeptide comprising a variant polypeptide as defined herein is provided. In one embodiment, the variant polypeptide is a mature form of the polypeptide (SEQ ID NO: 1), wherein the 21 amino acid leader sequence is cleaved, so that the N-terminus of the polypeptide begins at the aspartic acid (D) residue. In one aspect, the variants include a C-terminal starch binding domain. A representative amino acid sequence of a starch binding domain comprises or consist of an amino acid sequence of SEQ ID NO: 36. Other variants include variants wherein between one and about 25 amino acid residues have been added or deleted with respect to SEQ ID NO: 1. In one aspect, the variant has the amino acid sequence of SEQ ID NO: 1, wherein any number between one and about 25 amino acids have been substituted. In a further aspect, the variant has the amino acid sequence of SEQ ID NO: 1, wherein any number between three and twelve amino acids has been substituted. In a further aspect, the variant has the amino acid sequence of SEQ ID NO: 1, wherein any number between five and nine amino acids has been substituted.

In one aspect, at least at least two, in another aspect at least three, and yet in another aspect at least five amino acids of SEQ ID NO: 1 has been substituted.

In a further aspect, the length of the polypeptide variant is 390 to 540 amino acids. In a further aspect, the length of the polypeptide variant is 410 to 440 amino acids. In a further aspect, the length of the polypeptide variant is 420 to 435 amino acids. In a further aspect, the length of the polypeptide variant is 429 to 430 amino acids.

In one aspect, the invention relates to a polypeptide having amylase activity comprising an amino acid sequence having:
  a) at least 65% sequence identity to the amino acid sequence of SEQ ID NO: 1, and wherein the polypeptide comprises one or more amino acid substitutions at the following positions: 88 or 205, and/or b) at least 78% sequence identity to the amino acid sequence of SEQ ID NO: 1, and wherein the polypeptide comprises one or more amino acid substitutions at the following positions: 16, 48, 97, 105, 235, 240, 248, 266, 311, 347, 350, 362, 364, 369, 393, 395, 396, 400, 401, 403, 412 or 409, and/or c) at least 78% sequence identity to the amino acid sequence of SEQ ID NO: 1, and wherein the polypeptide comprises one or more of the following amino acid substitutions: 42K/A/V/N/I/H/F, 34Q, 100Q/K/N/R, 272D, 392 K/D/E/Y/N/Q/R/T/G or 399C/H, and/or d) at least 95% sequence identity to the amino acid sequence of SEQ ID NO: 1, and wherein the polypeptide comprises one or more amino acid substitutions at the following positions: 44, 96, 204, 354 or 377, and/or e) at least 95% sequence identity to the amino acid sequence of SEQ ID NO: 1, and wherein the polypeptide comprises the following amino acid substitution: 392S wherein an amino acid substitution is relative to the corresponding amino acid of SEQ ID NO:1 and the positions are with reference to the position numbering of the sequence shown as SEQ ID NO: 1.

In a further aspect, the polypeptide as defined herein comprises one or more amino acid substitutions at the following positions: 88, 205, 235, 240, 248, 266, 311, 377 or 409 and/or one or more of the following amino acid substitutions: 42K/A/V/N/I/H/F, 34Q, 100Q/K/N/R, 272D or 392K/D/E/Y/N/Q/R/S/T/G. In a further aspect, the polypeptide as defined herein comprises one or more amino acid substitutions at the following positions: 88, 205, 235, 240, 311 or 409 and/or one or more of the following amino acid substitutions: 42K/N/I/H/F, 272D, or 392 K/D/E/Y/N/Q/R/S/T/G. In a further aspect, the polypeptide as defined herein comprises amino acid substitutions at least in four, five or in all of the following positions: 88, 205, 235, 240, 311 or 409 and/or has at least one, or two the following amino acid substitutions: 42K/N/I/H/F, 272D or 392 K/D/E/Y/N/Q/R/S/T/G. In a further aspect, the polypeptide as defined herein further comprises one or more of the following amino acids 33Y, 34N, 70D, 121F, 134R, 141P, 146G, 157L, 161A, 178F, 179T, 223E/S/K/A, 229P, 307K, 309P and 334P. In a further aspect, the polypeptide as defined herein further has the following amino acids 33Y, 34N, 70D, 121F, 134R, 141P, 146G, 157L, 161A, 178F, 179T, 229P, 307K, 309P and 334P. In a further aspect, the polypeptide as defined herein has at least one of the amino acid substitutions in a) of claim 1 and further comprises one or more amino acid substitutions at the following positions: 44, 96, 204, 354 or 377. In a further aspect, the polypeptide as defined herein has at least 90, 91, 92, 93, 94, 95, 96, 97, 98, or 99% sequence identity to the amino acid sequence of SEQ ID NO: 1. In a further aspect, the polypeptide as defined herein has the amino acid 34Q. In a further aspect, the polypeptide as defined herein has the amino acid 42K/F/H/I/N/A/V. In a further aspect, the polypeptide as defined herein has the amino acid 42K/F/H/I/N. In a further aspect, the polypeptide as defined herein has the amino acid 42K. In a further aspect, the polypeptide as defined herein comprises an amino acid substitution in position 88. In a further aspect, the polypeptide as defined herein has the amino acid 88L/Y/K. In a further aspect, the polypeptide as defined herein has the amino acid 88L. In a further aspect, the polypeptide as defined herein has the amino acid 88Y. In a further aspect, the polypeptide as defined herein comprises an amino acid substitution in position 205. In a further aspect, the polypeptide as defined herein has the amino acid 205L/K/M/N/Q/R/V/Y. In a further aspect, the polypeptide as defined herein has the amino acid 205L/K/M/N/Q/R/V. In a further aspect, the polypeptide as defined herein has the amino acid 205L. In a further aspect, the polypeptide as defined herein comprises an amino acid substitution in position 235. In a further aspect, the polypeptide as defined herein has the amino acid 235H/K/R/Q/S. In a further aspect, the polypeptide as defined herein has the amino acid 235H/K/R/Q. In a further aspect, the polypeptide as defined herein has the amino acid 235H/K/R. In a further aspect, the polypeptide as defined herein has the amino acid 235R. In a further aspect, the polypeptide as defined herein has the amino acid 235H. In a further aspect, the polypeptide as defined herein has the amino acid 235K. In a further aspect, the polypeptide as defined herein comprises an amino acid substitution in position 240. In a further aspect, the polypeptide as defined herein has the amino acid 240E/H/M/D/S. In a further aspect, the polypeptide as defined herein has the amino acid 240E/H/M/D. In a further aspect, the polypeptide as defined herein has the amino acid 240E. In a further aspect, the polypeptide as defined herein has the amino acid 272D. In a further aspect, the polypeptide as defined herein comprises an amino acid substitution in position 311. In a further aspect, the polypeptide as defined herein has the amino acid 311P. In a further aspect, the polypeptide as defined herein comprises an amino acid substitution in position 409. In a further aspect, the polypeptide as defined herein has the amino acid 409H/Q/T/E. In a further aspect, the polypeptide as defined herein has the amino acid 409E. In a further aspect, the polypeptide as defined herein has the amino acid 100Q/K/N/R. In a further aspect, the polypeptide as defined herein has the amino acid 100Q. In a further aspect, the polypeptide as defined herein has the amino acid 392D/E/K/Y/N/Q/R/S/T/G. In a further aspect, the polypeptide as defined herein has the amino acid 392D/E/K/Y/N/Q/R/S/T. In a further aspect, the polypeptide as defined herein has the amino acid 392D/E/K/Y. In a further aspect, the polypeptide as defined herein has the amino acid 392D. In a further aspect, the polypeptide as defined herein has the amino acid 392E. In a further aspect, the polypeptide as defined herein has the amino acid 392K. In a further aspect, the polypeptide as defined herein has the amino acid 392Y. In a further aspect, the polypeptide as defined herein has both of the following amino acids 235R and 311P. In a further aspect, the polypeptide as defined herein comprises an amino acid substitution in position 16. In a further aspect, the polypeptide as defined herein has the amino acid 16/A/E/K. In a further aspect, the polypeptide as defined herein comprises an amino acid substitution in position 48. In a further aspect, the polypeptide as defined herein has the amino acid 48/C/L. In a further aspect, the polypeptide as defined herein comprises an amino acid substitution in position 97. In a further aspect, the polypeptide as defined herein comprises an amino acid substitution in position 105. In a further aspect, the polypeptide as defined herein has the amino acid 105/N/R. In a further aspect, the polypeptide as defined herein comprises an amino acid substitution in position 248. In a further aspect, the polypeptide as defined herein comprises an amino acid substitution in position 266. In a further aspect, the polypeptide as defined herein comprises an amino acid substitution in position 347. In a further aspect, the polypeptide as defined herein has the amino acid 347/C/D/H/K. In a further aspect, the polypeptide as defined herein comprises an amino acid substitution in position 350. In a further aspect, the polypeptide as defined herein has the amino acid 350E/H/N. In a further aspect, the polypeptide as defined herein comprises an amino acid substitution in position 354. In a further aspect, the polypeptide as defined herein has the amino acid 354D/E. In a further aspect, the polypeptide as defined herein comprises an amino acid substitution in position 362. In a further aspect, the polypeptide as defined herein has the amino acid 362E/H/P. In a further aspect, the polypeptide as defined herein comprises an amino acid substitution in position 364. In a further aspect, the polypeptide as defined herein has the amino acid 364E/K/NQ. In a further aspect, the polypeptide as defined herein comprises an amino acid substitution in position 369. In a further aspect, the polypeptide as defined herein has the amino acid 369I/N. In a further aspect, the polypeptide as defined herein comprises an amino acid substitution in position 377. In a further aspect, the polypeptide as defined herein comprises an amino acid substitution in position 393. In a further aspect, the polypeptide as defined herein has the amino acid 393D/E/K. In a further aspect, the polypeptide as defined herein comprises an amino acid substitution in position 395. In a further aspect, the polypeptide as defined herein has the amino acid 395C/E/K. In a further aspect, the polypeptide as defined herein comprises an amino acid substitution in position 396. In a further aspect, the polypeptide as defined herein has the amino acid 396D/E. In a further aspect, the polypeptide as defined herein comprises an amino acid substitution in position 399. In a further aspect, the polypeptide as defined herein has the amino acid 399C/H. In a further aspect, the polypeptide as defined herein comprises an amino acid substitution in position 400. In a further aspect, the polypeptide as defined herein has the amino acid 400S/W. In a further aspect, the polypeptide as defined herein comprises an amino acid substitution in position 401. In a further aspect, the polypeptide as defined herein has the amino acid 401D/K. In a further aspect, the polypeptide as defined herein comprises an amino acid substitution in position 403. In a further aspect, the polypeptide as defined herein has the amino acid 403E/T/V. In a further aspect, the polypeptide as defined herein comprises an amino acid substitution in position 412. In a further aspect, the polypeptide as defined herein has the amino acid 412D/N. In a further aspect, the polypeptide as defined herein further comprises one or more of the following amino acids 121F, 134R, 141P, 229P, or 307K. In a further aspect, the polypeptide as defined herein has one or more of the following amino acids 42K, 88L, 205L, 235R, 240E, 272D, 311P, 392D, or 409E. In a further aspect, the polypeptide as defined herein comprises the following amino acids 42K, 88L, 235R, 311P, 392D and either 223S, 223K or 223A. In a further aspect, the polypeptide as defined herein further comprises one or more selected from the group consisting of 272D, 409E, 205L and 240E. In a further aspect, the polypeptide as defined herein has at least four, five, six, seven or eight of the following amino acids 42K, 88L, 205L, 235R, 240E, 272D, 311P, 392D, or 409E. In a further aspect, the polypeptide as defined herein has the amino acid 223A/K/S. In a further aspect, the polypeptide as defined herein has the following amino acids 42K, 88L, 223S, 235R, 311P and 392D. In a further aspect, the polypeptide as defined herein has the following amino acids 42K, 88L, 223K, 235R, 272D, 311P and 392D. In a further aspect, the polypeptide as defined herein has the following amino acids 42K, 88L, 223S, 235R, 311P, 392D and 409E. In a further aspect, the polypeptide as defined herein has the following amino acids 42K, 88L, 205L, 223S, 235R, 311P, 392D and 409E. In a further aspect, the polypeptide as defined herein has the following amino acids 42K, 88L, 205L, 223K, 240E, 235R, 311P, 392D and 409E. In a further aspect, the polypeptide as defined herein has the following amino acids 42K, 88L, 205L, 223A, T235R, 311P, 392D and 409E. In a further aspect, the polypeptide as defined herein has one or more amino acids in the N-terminus. In one aspect, the polypeptide as defined herein has the amino acid M at the N-terminus. In a further aspect, the polypeptide as defined herein comprises one or more amino acid substitutions at the following positions: 88, 205, 235 or 409 and/or one or more of the following amino acid substitutions: 42K, 34Q, 100Q, 223A/S, 240E, 311P, 392D, or 409E with reference to the position numbering of the sequence shown as SEQ ID NO: 1. In a further aspect, the polypeptide as defined herein comprises one or more of the following amino acid substitutions: 42K, 34Q, 88K/L/Y, 100Q, 205L, 223A/S/K, 235K/H/Q/R, 240E/D, 248H, 266T, 311P, 377D/E/P, 392K/D/Y or 409E. In a further aspect, the polypeptide as defined herein comprises one or more of the following amino acid substitutions: 34Q, 42K, 88L, 100Q, 205L, 223A/S/K, 235K/R, 240E, 311P, 392D or 409E. In a further aspect, the polypeptide as defined herein comprises the following amino acid substitutions: 235R and 311P. In a further aspect, the polypeptide as defined herein comprises the amino acid substitution 42K. In a further aspect, the polypeptide as defined herein comprises the following amino acid substitutions: 42K and 223S. In a further aspect, the polypeptide as defined herein comprises the following amino acid substitutions: 42K, 223S and 392D. In a further aspect, the polypeptide as defined herein comprises the following amino acid substitutions: 42K, 88L, 223A, 235R, 311P and 392D. In a further aspect, the polypeptide as defined herein comprises the following amino acid substitutions: 42K, 88L, 205L, 223S, 235R, 240E, 311P, 392D and 409E. In a further aspect, the polypeptide as defined herein comprises the following amino acid substitutions: 42K, 88L, 205L, 223K, 235R, 240E, 311P, 392D and 409E. In a further aspect, the polypeptide as defined herein comprises the following amino acid substitutions: 42K, 88L, 205L, 223S, 235R, 311P and 392D. In a further aspect, the polypeptide as defined herein comprises the following amino acid substitutions: 34Q, 42K, 88L, 205L, 223K, 235R, 240E, 311P, 392D and 409E. In a further aspect, the polypeptide as defined herein comprises the following amino acid substitutions: 42K, 88L, 100Q, 205L, 223K, 235R, 240E, 311P, 392D and 409E.

Representative embodiments of the polypeptides as defined herein comprises an amino acid sequence selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34. Further representative embodiments of the polypeptides as defined herein comprises an amino acid sequence selected from the group consisting of SEQ ID NO: 12, SEQ ID NO: 13, SEQ ID NO: 14, SEQ ID NO: 15, SEQ ID NO: 16, and SEQ ID NO: 17. Further representative embodiments of the polypeptides as defined herein has an amino acid sequence selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34. Further representative embodiments of the polypeptides as defined herein has an amino acid sequence selected from the group consisting of SEQ ID NO: 12, SEQ ID NO: 13, SEQ ID NO: 14, SEQ ID NO: 15, SEQ ID NO: 16, and SEQ ID NO: 17, and optionally one or more amino acids at the N-terminus.

In one aspect, the polypeptides as defined herein comprises the sequence HGGDEIILQFHWN (SEQ ID NO: 37) at the positions corresponding to positions 13-26 with reference to the position numbering of the sequence shown as SEQ ID NO: 1.

In one aspect, the polypeptides as defined herein comprises the sequence DGF-X1-AIW-X2-P-X3-PWRD-X4-SSW (SEQ ID NO: 38), wherein X1 is S or T, X2 is M or L, X3 is V or P and X4 is any natural occurring amino acid residue, preferably an L-amino acid, at the positions corresponding to positions 49-66 with reference to the position numbering of the sequence shown as SEQ ID NO: 1.

In one aspect, the polypeptides as defined herein comprises the sequence GGEGYFW (SEQ ID NO: 39) at the positions corresponding to positions 79-85 with reference to the position numbering of the sequence shown as SEQ ID NO: 1.

In one aspect, the polypeptides as defined herein comprises the sequence VPNH (SEQ ID NO: 40) at the positions corresponding to positions 114-117 with reference to the position numbering of the sequence shown as SEQ ID NO: 1.

In one aspect, the polypeptides as defined herein comprises the sequence CDDGD (SEQ ID NO: 41) at the positions corresponding to positions 150-154 with reference to the position numbering of the sequence shown as SEQ ID NO: 1.

In one aspect, the polypeptides as defined herein comprises the sequence AGGFRFDFVRG (SEQ ID NO: 42) at the positions corresponding to positions 187-197 with reference to the position numbering of the sequence shown as SEQ ID NO: 1.

In one aspect, the polypeptides as defined herein comprises the sequence FALK (SEQ ID NO: 43) at the positions corresponding to positions 256-259 with reference to the position numbering of the sequence shown as SEQ ID NO: 1.

In one aspect, the polypeptides as defined herein comprises the sequence WREVAVTFVDNHD (SEQ ID NO: 44) at the positions corresponding to positions 282-294 with reference to the position numbering of the sequence shown as SEQ ID NO: 1.

In one aspect, the polypeptides as defined herein comprises the sequence GYSPG (SEQ ID NO: 45) at the positions corresponding to positions 296-300 with reference to the position numbering of the sequence shown as SEQ ID NO: 1.

In one aspect, the polypeptides as defined herein comprises the sequence GQH (SEQ ID NO: 46) at the positions corresponding to positions 304-306 with reference to the position numbering of the sequence shown as SEQ ID NO: 1.

In one aspect, the polypeptides as defined herein comprises the sequence AYAYI (SEQ ID NO: 47) at the positions corresponding to positions 318-322 with reference to the position numbering of the sequence shown as SEQ ID NO: 1.

In one aspect, the polypeptides as defined herein comprises the sequence SPGTP (SEQ ID NO: 48) at the positions corresponding to positions 325-329 with reference to the position numbering of the sequence shown as SEQ ID NO: 1.

In one aspect, the polypeptides as defined herein comprises the sequence VYW (SEQ ID NO: 49) at the positions corresponding to positions 331-333 with reference to the position numbering of the sequence shown as SEQ ID NO: 1.

In one aspect, the polypeptides as defined herein comprises the sequence HMYDWG (SEQ ID NO: 50) at the positions corresponding to positions 335-340 with reference to the position numbering of the sequence shown as SEQ ID NO: 1.

In another aspect, the polypeptide variant as defined herein has the sequence of SEQ ID NO:1, wherein any number between about one and about 25 amino acids have been substituted. Representative examples of polypeptide variants as defined herein having single or several amino acid substitutions are shown in below TABLE A:

| pMS | Mutations compared to pMS382 having SEQ ID NO: 1 |
|---|---|
| pms1104 (SEQ ID NO: 20) | Q42K |
| pms1105 (SEQ ID NO: 27) | Q42K, E223S |
| pms1723 (SEQ ID NO: 28) | Q42K, E223S, A392D |
| pms2104 (SEQ ID NO: 29) | Q42K, R88L, E223A, T235R, Q311P, A392D |
| pms2118 (SEQ ID NO: 34) | Q42K, R88L, S205L, E223S, T235R, Q240E, Q311P, A392D, S409E |
| pms2124 (SEQ ID NO: 31) | Q42K, R88L, S205L, E223K, T235R, Q240E, Q311P, A392D, S409E |
| pms1284 (SEQ ID NO: 23) | T235R, Q311P |
| pms1286 (SEQ ID NO: 22) | T235R |
| pms1290 (SEQ ID NO: 24) | T235K |
| pms465 (SEQ ID NO: 18) | E223S |
| pms1042 (SEQ ID NO: 19) | Q311P |
| pms1153 (SEQ ID NO: 21) | R88L |
| pms1484 (SEQ ID NO: 25) | S205L |
| pms1579 (SEQ ID NO: 26) | S409E |
| pms2138 (SEQ ID NO: 30) | Q42K, R88L, S205L, E223S, T235R, Q311P, A392D |
| pms2177 (SEQ ID NO: 32) | N34Q, Q42K, R88L, S205L, E223K, T235R, Q240E, Q311P, A392D, S409E |
| pms2178 (SEQ ID NO: 33) | Q42K, R88L, G100Q, S205L, E223K, T235R, Q240E, Q311P, A392D, S409E |
| pms1776 (SEQ ID NO: 12) | Q42K, R88L, E223S, T235R, Q311P, A392D |
| pms1934 (SEQ ID NO: 13) | Q42K, R88L, E223K, T235R, H272D, Q311P, A392D |
| pms2020 (SEQ ID NO: 14) | Q42K, R88L, E223S, T235R, Q311P, A392D, S409E |
| pms2022 (SEQ ID NO: 15) | Q42K, R88L, S205L, E223S, T235R, Q311P, A392D, S409E |
| pms2062 (SEQ ID NO: 16) | Q42K, R88L, S205L, E223K, Q240E, T235R, Q311P, A392D, S409E |
| pms2171 (SEQ ID NO: 17) | Q42K, R88L, S205L, E223A, T235R, Q311P, A392D, S409E |

The polypeptide variants as defined herein may have an altered thermostability, an altered endo-amylase activity, an altered exo-amylase activity, and/or an altered ratio of exo- to endo-amylase activity compared to the amino acid sequence of SEQ ID NO: 1 or SEQ ID NO: 10. In one aspect, the polypeptides as defined herein have an improved antistaling effect compared to the amylase of SEQ ID NO: 1. In another aspect, the polypeptides as defined herein have an improved thermostability compared to the amylase of SEQ ID NO: 1.

The polypeptide variants as defined herein may have up to 25, 23, 21, 19, 17, 15, 13, 11, 9, 8, 7, 6, 5 amino acid deletions, additions, insertions, or substitutions compared to the amino acid sequence of SEQ ID NO: 1.

The present disclosure also relates to each and every G4-amylase backbone having SEQ ID NO: 2, 4, 6, or 8 comprising the substitutions as further defined herein.

Nucleic acids encoding the polypeptide variants above also are provided. In one embodiment, a nucleic acid encoding a polypeptide variant as defined herein is a nucleotide sequence encoding the protein comprising an amino acid sequence of residues 1-429 of SEQ ID NO: 1 as set forth in SEQ ID NO: 52. For example nucleotide sequence SEQ ID NO: 3 encodes the G4 amylase backbone with SEQ ID NO: 2. As is well understood by one skilled in the art, the genetic code is degenerate, meaning that multiple codons in some cases may encode the same amino acid. Nucleic acids can include genomic DNA, mRNA, and cDNA that encodes a polypeptide variant.

Enzyme variants can be characterized by their nucleic acid and primary polypeptide sequences, by three dimensional structural modeling, and/or by their specific activity. Additional characteristics of the polypeptide variants as defined herein include stability, pH range, oxidation stability, and thermostability, for example. Levels of expression and enzyme activity can be assessed using standard assays known to the artisan skilled in this field. In another aspect, variants demonstrate improved performance characteristics relative to the polypeptide with SEQ ID NO: 1, such as improved stability at high temperatures, e.g., 65-85° C. In one aspect, the polypeptide variants as defined herein are advantageous for use in liquefaction or other processes that require elevated temperatures, such as baking. For example, a thermostable polypeptide variant as defined herein can degrade starch at temperatures of about 55° C. to about 85° C. or more.

An expression characteristic means an altered level of expression of the variant, when the variant is produced in a particular host cell. Expression generally relates to the amount of active variant that is recoverable from a fermentation broth using standard techniques known in this art over a given amount of time. Expression also can relate to the amount or rate of variant produced within the host cell or secreted by the host cell. Expression also can relate to the rate of translation of the mRNA encoding the variant enzyme.

A nucleic acid complementary to a nucleic acid encoding any of the polypeptide variants as defined herein set forth herein is provided. Additionally, a nucleic acid capable of hybridizing to the complement is provided. In another embodiment, the sequence for use in the methods and compositions described here is a synthetic sequence. It includes, but is not limited to, sequences made with optimal codon usage for expression in host organisms, such as yeast.

The polypeptide variants as provided herein may be produced synthetically or through recombinant expression in a host cell, according to procedures well known in the art. The expressed polypeptide variant as defined herein optionally is isolated prior to use. In another embodiment, the polypeptide variant as defined herein is purified following expression. Methods of genetic modification and recombinant production of polypeptide variants are described, for example, in U.S. Pat. Nos. 7,371,552, 7,166,453; 6,890,572; and 6,667,065; and U.S. Published Application Nos. 2007/0141693; 2007/0072270; 2007/0020731; 2007/0020727; 2006/0073583; 2006/0019347; 2006/0018997; 2006/0008890; 2006/0008888; and 2005/0137111. The relevant teachings of these disclosures, including polypeptide-encoding polynucleotide sequences, primers, vectors, selection methods, host cells, purification and reconstitution of expressed polypeptide variants, and characterization of polypeptide variants as defined herein, including useful buffers, pH ranges, $Ca^{2+}$ concentrations, substrate concentrations and enzyme concentrations for enzymatic assays, are herein incorporated by reference.

In another embodiment, suitable host cells include a Gram positive bacterium selected from the group consisting of *Bacillus subtilis, B. licheniformis, B. lentus, B. brevis, B. stearothermophilus, B. alkalophilus, B. amyloliquefaciens, B. coagulans, B. circulans, B. lautus, B. thuringiensis, Streptomyces lividans,* or *S. murinus*; or a Gram negative bacterium, wherein said Gram negative bacterium is *Escherichia coli* or a *Pseudomonas* species. In one aspect, the host cell is a *B. subtilus* or *B. licheniformis*. In one embodiment, the host cell is *B. subtilis*, and the expressed protein is engineered to comprise a *B. subtilis* signal sequence, as set forth in further detail below. In one aspect, the host cell expresses the polynucleotide as set out in the claims.

In some embodiments, a host cell is genetically engineered to express a polypeptide variant as defined herein with an amino acid sequence having at least about 78%, 80%, 85%, 90%, 91%, 92%, 93%, 94%, 95%, 96%, 97%, 98% or 99% identity with the polypeptide of SEQ ID NO:1. In some embodiments, the polynucleotide encoding a polypeptide variant as defined herein will have a nucleic acid sequence encoding the protein of SEQ ID NO: 1 or a nucleic acid sequence having at least about 78%, 80%, 85%, 90%, 95%, 96%, 97%, 98% or 99% sequence identity with a nucleic acid encoding the protein of SEQ ID NO: 1. In one embodiment, the nucleic acid sequence has at least about 78%, 80%, 85%, 90%, 95%, 96%, 97%, 98% or 99% sequence identity to the nucleic acid of SEQ ID NO: 52.

In one aspect, the invention relates to a vector comprising a polynucleotide. In one aspect, of the invention a bacterial cell comprises the vector. In some embodiments, a DNA construct comprising a nucleic acid encoding a variant is transferred to a host cell in an expression vector that comprises regulatory sequences operably linked to an encoding sequence. The vector may be any vector that can be integrated into a fungal host cell genome and replicated when introduced into the host cell. The FGSC Catalogue of Strains, University of Missouri, lists suitable vectors. Additional examples of suitable expression and/or integration vectors are provided in Sambrook et al., MOLECULAR CLONING: A LABORATORY MANUAL, $3^{rd}$ ed., Cold Spring Harbor Laboratory Press, Cold Spring Harbor, N.Y. (2001); Bennett et al., MORE GENE MANIPULATIONS IN FUNGI, Academic Press, San Diego (1991), pp. 396-428; and U.S. Pat. No. 5,874,276. Exemplary vectors include pFB6, pBR322, PUC18, pUC100 and pENTR/D, pDON™201, pDONR™221, pENTR™, pGEM®3Z and pGEM®4Z. Exemplary for use in bacterial cells include pBR322 and pUC19, which permit replication in *E. coli*, and pE194, for example, which permits replication in *Bacillus*.

In some embodiments, a nucleic acid encoding a variant is operably linked to a suitable promoter, which allows transcription in the host cell. The promoter may be derived from genes encoding proteins either homologous or heterologous to the host cell. Suitable non-limiting examples of promoters include cbh1, cbh2, egl1, and egl2 promoters. In one embodiment, the promoter is one that is native to the host cell. For example, when *P. saccharophila* is the host, the promoter is a native *P. saccharophila* promoter. An "inducible promoter" is a promoter that is active under environmental or developmental regulation. In another embodiment, the promoter is one that is heterologous to the host cell.

In some embodiments, the coding sequence is operably linked to a DNA sequence encoding a signal sequence. A representative signal peptide is SEQ ID NO: 11, which is the native signal sequence of the PS4 precursor. In other embodiments, the DNA encoding the signal sequence is replaced with a nucleotide sequence encoding a signal sequence from a species other than *P. saccharophila*. In this embodiment, the polynucleotide that encodes the signal sequence is immediately upstream and in-frame of the polynucleotide that encodes the polypeptide. The signal sequence may be selected from the same species as the host cell. In one non-limiting example, the signal sequence is a cyclodextrin glucanotransferase (CGTase; EC 2.4.1.19) signal sequence from *Bacillus* sp., and the variant polypeptides disclosed herein is expressed in a *B. subtilis* host cell. A methionine residue may be added to the N-terminus of the signal sequence.

In additional embodiments, a signal sequence and a promoter sequence comprising a DNA construct or vector to be introduced into a fungal host cell are derived from the same source. In some embodiments, the expression vector also includes a termination sequence. In one embodiment, the termination sequence and the promoter sequence are derived from the same source. In another embodiment, the termination sequence is homologous to the host cell.

In some embodiments, an expression vector includes a selectable marker. Examples of suitable selectable markers include those that confer resistance to antimicrobial agents, e.g., hygromycin or phleomycin. Nutritional selective markers also are suitable and include amdS, argB, and pyr4. In one embodiment, the selective marker is the amdS gene, which encodes the enzyme acetamidase; it allows transformed cells to grow on acetamide as a nitrogen source. The use of an *A. nidulans* amdS gene as a selective marker is described in Kelley et al., *EMBO J.* 4: 475-479 (1985) and Penttila et al., *Gene* 61: 155-164 (1987).

A suitable expression vector comprising a DNA construct with a polynucleotide encoding a variant may be any vector that is capable of replicating autonomously in a given host organism or integrating into the DNA of the host. In some embodiments, the expression vector is a plasmid. In some embodiments, two types of expression vectors for obtaining expression of genes are contemplated. The first expression vector comprises DNA sequences in which the promoter, coding region, and terminator all originate from the gene to be expressed. In some embodiments, gene truncation is obtained by deleting undesired DNA sequences, e.g., DNA encoding the C-terminal starch-binding domain, to leave the domain to be expressed under control of its own transcriptional and translational regulatory sequences. The second type of expression vector is preassembled and contains sequences required for high-level transcription and a selectable marker. In some embodiments, the coding region for a gene or part thereof is inserted into this general-purpose expression vector, such that it is under the transcriptional control of the expression construct promoter and terminator sequences. In some embodiments, genes or part thereof are inserted downstream of the strong cbh1 promoter.

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Ausubel et al. (1987), supra, chapter 9; Sambrook et al. (2001), supra; and Campbell et al., *Curr. Genet.* 16: 53-56 (1989). The expression of heterologous protein in *Trichoderma* is described, for example, in U.S. Pat. No. 6,022,725; U.S. Pat. No. 6,268,328; Harkki et al., *Enzyme Microb. Technol.* 13: 227-233 (1991); Harkki et al., *BioTechnol.* 7: 596-603 (1989); EP 244,234; and EP 215,594. In one embodiment, genetically stable transformants are constructed with vector systems whereby the nucleic acid encoding a variant is stably integrated into a host cell chromosome. Transformants are then purified by known techniques.

In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on solid non-selective medium, e.g., a medium that lacks acetamide, harvesting spores from this culture medium and determining the percentage of these spores that subsequently germinate and grow on selective medium containing acetamide. Other methods known in the art may be used to select transformants.

To evaluate the expression of a variant in a host cell, assays can measure the expressed protein, corresponding mRNA, or α-amylase activity. For example, suitable assays include Northern and Southern blotting, RT-PCR (reverse transcriptase polymerase chain reaction), and in situ hybridization, using an appropriately labeled hybridizing probe. Suitable assays also include measuring activity in a sample. Suitable assays of the exo-activity of the variant include, but are not limited to, the Betamyl® assay (Megazyme, Ireland). Suitable assays of the endo-activity of the variant include, but are not limited to, the Phadebas blue assay (Pharmacia and Upjohn Diagnostics AB). Assays also include HPLC analysis of liquefact prepared in the presence of the variant. HPLC can be used to measure amylase activity by separating DP-3 and DP-4 saccharides from other components of the assay.

The variant polypeptides described here preferably have improved properties when compared to SEQ ID NO:1, such as any one or more of improved thermostability, improved pH stability, or improved exo-specificity. The variant polypeptides described here preferably also have improved handling properties, such that a food product treated with a variant polypeptide has any one or all of lower firmness, higher resilience, higher cohesiveness, lower crumbliness, or higher foldability compared to a food product which has been treated with SEQ ID NO:1.

Without wishing to be bound by any particular theory, we believe that the mutations at the particular positions have individual and cumulative effects on the properties of a polypeptide comprising such mutations.

Preferably, the variant polypeptide is thermostable; preferably, it has higher thermostability than SEQ ID NO:1.

In wheat and other cereals the external side chains in amylopectin are in the range of DP 12-19. Thus, enzymatic hydrolysis of the amylopectin side chains, for example, by variant polypeptides as described having non-maltogenic exoamylase activity, can markedly reduce their crystallisation tendencies.

Starch in wheat and other cereals used for baking purposes is present in the form of starch granules which generally are resistant to enzymatic attack by amylases. Thus starch modification is mainly limited to damaged starch and is progressing very slowly during dough processing and initial baking until gelatinisation starts at about 60 C. As a consequence hereof only amylases with a high degree of thermostability are able to modify starch efficiently during baking. And generally the efficiency of amylases is increased with increasing thermostability. That is because the more thermostable the enzyme is the longer time it can be active during baking and thus the more antistaling effect it will provide.

Accordingly, the use of variant polypeptides as described here when added to the starch at any stage of its processing into a food product, e.g., before during or after baking into bread can retard or impede or slow down the retrogradation. Such use is described in further detail below.

As used herein the term "thermostable" relates to the ability of the enzyme to retain activity after exposure to elevated temperatures. Preferably, the variant polypeptide is capable of degrading starch at temperatures of from about 55° C. to about 80° C. or more. Suitably, the enzyme retains its activity after exposure to temperatures of up to about 95° C.

The thermostability of an enzyme such as a non-maltogenic exoamylase is measured by its half life. Thus, the variant polypeptides described here have half lives extended relative to the parent enzyme by preferably 10%, 20%, 30%, 40%, 50%, 60%, 70%, 80%, 90%, 100%, 200% or more, preferably at elevated temperatures of from 55° C. to about 95° C. or more, preferably at about 80° C.

As used here, the half life (t½) is the time (in minutes) during which half the enzyme activity is inactivated under defined heat conditions. In preferred embodiments, the half life is assayed at 80 degrees C. Preferably; the sample is heated for 1-10 minutes at 80° C. or higher. The half life value is then calculated by measuring the residual amylase activity, by any of the methods described here. Preferably, a half life assay is conducted as described in more detail in the Examples.

Preferably, the variant polypeptides described here are active during baking and hydrolyse starch during and after the gelatinization of the starch granules which starts at temperatures of about 55 degrees C. The more thermostable the non-maltogenic exoamylase is the longer time it can be active and thus the more antistaling effect it will provide. However, during baking above temperatures of about 85 degrees C., enzyme inactivation can take place. If this happens, the non-maltogenic exoamylase may be gradually inactivated so that there is substantially no activity after the baking process in the final bread. Therefore preferentially the non-maltogenic exoamylases suitable for use as described have an optimum temperature above 50 degrees C. and below 98 degrees C.

The thermostability of the variant polypeptides described here can be improved by using protein engineering to become more thermostable and thus better suited for the uses described here; we therefore encompass the use of variant polypeptides modified to become more thermostable by protein engineering.

Preferably, the variant polypeptide is pH stable; more preferably, it has a higher pH stability than SEQ ID NO: 1. As used herein the term "pH stable" relates to the ability of the enzyme to retain activity over a wide range of pHs. Preferably, the variant polypeptide is capable of degrading starch at a pH of from about 5 to about 10.5. In one embodiment, the degree of pH stability may be assayed by measuring the half life of the enzyme in specific pH conditions. In another embodiment, the degree of pH stability may be assayed by measuring the activity or specific activity of the enzyme in specific pH conditions. The specific pH conditions may be any pH from pH5 to pH10.5.

Thus, the variant polypeptide may have a longer half life, or a higher activity (depending on the assay) when compared to SEQ ID NO:1 under identical conditions. The variant polypeptides may have 10%, 20%, 30%, 40%, 50%, 60%, 70%, 80%, 90%, 100%, 200% or longer half life when compared to SEQ ID NO:1 under identical pH conditions. Alternatively, or in addition, they may have such higher activity when compared to SEQ ID NO:1 under identical pH conditions.

It is known that some non-maltogenic exoamylases can have some degree of endoamylase activity. In some cases, this type of activity may need to be reduced or eliminated since endoamylase activity can possibly negatively effect the quality of the final bread product by producing a sticky or gummy crumb due to the accumulation of branched dextrins.

Exo-specificity can usefully be measured by determining the ratio of total amylase activity to the total endoamylase activity. This ratio is referred to in this document as a "Exo-specificity index". In preferred embodiments, an enzyme is considered an exoamylase if it has a exo-specificity index of 20 or more, i.e., its total amylase activity (including exo-amylase activity) is 20 times or more greater than its endoamylase activity. In highly preferred embodiments, the exo-specificity index of exoamylases is 30 or more, 40 or more, 50 or more, 60 or more, 70 or more, 80 or more, 90 or more, or 100 or more. In highly preferred embodiments, the exo-specificity index is 150 or more, 200 or more, 300 or more, 400 or more, 500 or more or 600 or more.

The total amylase activity and the endoamylase activity may be measured by any means known in the art. For example, the total amylase activity may be measured by assaying the total number of reducing ends released from a starch substrate. Alternatively, the use of a Betamyl assay is described in further detail in the Examples, and for convenience, amylase activity as assayed in the Examples is described in terms of "Betamyl Units" in the Tables.

Endoamylase activity may be assayed by use of a Phadebas Kit (Pharmacia and Upjohn). This makes use of a blue labelled crosslinked starch (labelled with an azo dye); only internal cuts in the starch molecule release label, while external cuts do not do so. Release of dye may be measured by spectrophotometry. Accordingly, the Phadebas Kit measures endoamylase activity, and for convenience, the results of such an assay are referred to in this document as "Phadebas units".

In a highly preferred embodiment, therefore, the exo-specificity index is expressed in terms of Betamyl Units/Phadebas Units, also referred to as "B/Phad".

Exo-specificity may also be assayed according to the methods described in the prior art, for example, in our International Patent Publication Number WO99/50399. This measures exo-specificity by way of a ratio between the endoamylase activity to the exoamylase activity. Thus, in a preferred aspect, the variant polypeptide described here will have less than 0.5 endoamylase units (EAU) per unit of exoamylase activity. Preferably the non-maltogenic exoamylases which are suitable for use according to the present invention have less than 0.05 EAU per unit of exoamylase activity and more preferably less than 0.01 EAU per unit of exoamylase activity.

The variant polypeptide described here will preferably have exospecificity, for example measured by exo-specificity indices, as described above, consistent with their being exoamylases. Moreover, they preferably have higher or increased exospecificity when compared to SEQ ID NO:1. Thus, for example, the variant polypeptide may have 10%, 20%, 30%, 40%, 50%, 60%, 70%, 80%, 90%, 100%, 200% or higher exo-specificity index when compared to SEQ ID NO:1, preferably under identical conditions. They may have 1.5× or higher, 2× or higher, 5× or higher, 10× or higher, 50× or higher, 100× or higher, when compared to SEQ ID NO:1, preferably under identical conditions.

In general, a variant produced in cell culture is secreted into the medium and may be purified or isolated, e.g., by removing unwanted components from the cell culture medium. In some cases, a variant may be recovered from a cell lysate. In such cases, the enzyme is purified from the cells in which it was produced using techniques routinely employed by those of skill in the art. Examples include, but are not limited to, affinity chromatography, ion-exchange chromatographic methods, including high resolution ion-exchange, hydrophobic interaction chromatography, two-phase partitioning, ethanol precipitation, reverse phase HPLC, chromatography on silica or on a cation-exchange resin, such as DEAE, chromatofocusing, SDS-PAGE, ammonium sulfate precipitation, and gel filtration using Sephadex G-75, for example.

A polypeptide variant produced and purified by the methods described above is useful for a variety of industrial applications. In one embodiment, the polypeptide variant as defined herein is useful in a starch conversion process, particularly in a liquefaction process of a starch, e.g., corn starch, wheat starch, or barley starch. The desired end-product may be any product that may be produced by the enzymatic conversion of the starch substrate. For example, the desired product may be a syrup rich in saccharides useful for fermentation, particularly maltotriose, glucose, and/or maltose. The end product then can be used directly in a fermentation process to produce alcohol for fuel or drinking (i.e., potable alcohol). The skilled artisan is aware of various fermentation conditions that may be used in the production of ethanol or other fermentation end-products. A microbial organism capable of fermenting maltotrioses and/or less complex sugars, such as *S. cerevisiae* or a genetically modified variant thereof, is particularly useful. Suitable genetically altered variants of *S. cerevisiae* particularly useful for fermenting maltotrioses include variants that express AGT1 permease (Stambuck et al., *Lett. Appl. Microbiol.* 43: 370-76 (2006)), MTT1 and MTT1alt (Dietvorst et al., *Yeast* 22: 775-88 (2005)), or MAL32 (Dietvorst et al., *Yeast* 24: 27-38 (2007)). The present polypeptide variants also are useful in compositions and methods of food preparation, where enzymes that express amylase activity at high temperatures are desired.

The desirability of using a particular polypeptide variant will depend on the overall properties displayed by the polypeptide variant relative to the requirements of a particular application. As a general matter, polypeptide variants useful for a starch conversion process have substantial endo-amylase activity compared to wild-type PS4 or SEQ ID NO:1, and/or have a lower exo- to endo-amylase activity compared to wild-type PS4 or SEQ ID NO:1. Such polypeptide variants may be particularly useful in a liquefaction process, when used alone or combination with other amylase variants, where internal cleavage of complex branching saccharides lowers the viscosity of the substrate. Some polypeptide variants useful for liquefaction, however, are expected to have an endo-amylase activity comparable or even lower than wild-type PS4. Useful polypeptide variants include those with more or less exo-amylase activity than the wild-type PS4 or the SEQ ID NO: 1 polypeptide, depending on the application. Compositions may include one or a combination of amylase variants, each of which may display a different set of properties.

Those of skill in the art are well aware of available methods that may be used to prepare starch substrates for use in the processes disclosed herein. For example, a useful starch substrate may be obtained from tubers, roots, stems, legumes, cereals or whole grain. More specifically, the granular starch comes from plants that produce high amounts of starch. For example, granular starch may be obtained from corns, cobs, wheat, barley, rye, milo, sago, cassava, tapioca, sorghum, rice, peas, bean, banana, or potatoes. Corn contains about 60-68% starch; barley contains about 55-65% starch; millet contains about 75-80% starch; wheat contains about 60-65% starch; and polished rice contains 70-72% starch. Specifically contemplated starch substrates are cornstarch, wheat starch, and barley starch. The starch from a grain may be ground or whole and includes corn solids, such as kernels, bran and/or cobs. The starch may be highly refined raw starch or feedstock from starch refinery processes. Various starches also are commercially available. For example, cornstarch is available from Cerestar, Sigma, and Katayama Chemical Industry Co. (Japan); wheat starch is available from Sigma; sweet potato starch is available from Wako Pure Chemical Industry Co. (Japan); and potato starch is available from Nakaari Chemical Pharmaceutical Co. (Japan).

Maltodextrins are useful as starch substrates in embodiments of the present invention. Maltodextrins comprise starch hydrolysis products having about 20 or fewer dextrose (glucose) units. Typical commercial maltodextrins contain mixtures of polysaccharides including from about three to about nineteen linked dextrose units. Maltodextrins are defined by the FDA as products having a dextrose equivalence (DE) of less than 20. They are generally recognized as safe (GRAS) food ingredients for human consumption. Dextrose equivalence (DE) is a measure of reducing power compared to a dextrose (glucose) standard of 100. The higher the DE, the greater the extent of starch depolymerization, resulting in a smaller average polymer (polysaccharide) size, and the greater the sweetness. A particularly useful maltodextrin is MALTRIN®M040 obtained from cornstarch, available from Grain Processing Corp. (Muscatine, Iowa): DE 4.0-7.0; bulk density 0.51 g/cc; measured water content 6.38% by weight.

The starch substrate can be a crude starch from milled whole grain, which contains non-starch fractions, e.g., germ residues and fibers. Milling may comprise either wet milling or dry milling. In wet milling, whole grain is soaked in water or dilute acid to separate the grain into its component parts, e.g., starch, protein, germ, oil, kernel fibers. Wet milling efficiently separates the germ and meal (i.e., starch granules and protein) and is especially suitable for production of syrups. In dry milling, whole kernels are ground into a fine powder and processed without fractionating the grain into its component parts. Dry milled grain thus will comprise significant amounts of non-starch carbohydrate compounds, in addition to starch. Most ethanol comes from dry milling. Alternatively, the starch to be processed may be a highly refined starch quality, for example, at least about 90%, at least 95%, at least 97%, or at least 99.5% pure.

As used herein, the term "liquefaction" or "liquefy" means a process by which starch is converted to less viscous and shorter chain dextrins. This process involves gelatinization of starch simultaneously with or followed by the addition of a polypeptide variant as described herein. A thermostable polypeptide variant as described herein is preferably used for this application. Additional liquefaction-inducing enzymes optionally may be added.

In some embodiments, the starch or maltodextrin substrate prepared as described above is slurried with water. The starch or maltodextrin slurry may contain starch as a weight percent of dry solids of about 10-55%, about 20-45%, about 30-45%, about 30-40%, or optionally about 30-35%. The α-amylases, e.g., bacterial alpha-amylases, including *Bacillus* alpha-amylases, is usually supplied, for example, at about 1500 units per kg dry matter of starch, for example. To optimize α-amylase stability and activity, the pH of the slurry may be adjusted to the optimal pH for the used polypeptide variant. Other α-amylases may be added and may require different optimal conditions. Bacterial α-amylase remaining in the slurry following liquefaction may be deactivated by lowering pH in a subsequent reaction step or by removing calcium from the slurry.

The slurry of starch plus the polypeptide variant may be pumped continuously through a jet cooker, which is steam heated from about 85° C. to up to 105° C. Gelatinization occurs very rapidly under these conditions, and the enzymatic activity, combined with the significant shear forces, begins the hydrolysis of the starch substrate. The residence time in the jet cooker is very brief. The partly gelatinized starch may be passed into a series of holding tubes maintained at about 85-105° C. and held for about 5 min. to complete the gelatinization process. These tanks may contain baffles to discourage back mixing. As used herein, the term "secondary liquefaction" refers the liquefaction step subsequent to primary liquefaction, when the slurry is allowed to cool to room temperature. This cooling step can be about 30 minutes to about 180 minutes, e.g. about 90 minutes to 120 minutes.

A polypeptide variant as defined herein can be added to the liquefied starch obtained by the process above or to a maltodextrin slurry at about 0.01 to about 1.0 kg/MTDS. 1 kg/MTDS=0.1% by weight dissolved solids. In one embodiment, a polypeptide as defined herein can be added to a liquefied starch or maltodextrin slurry at a treatment level in a range from about 0.001% by weight to about 0.01% by weight based on dissolved solids. In a typical embodiment, a polypeptide as defined herein can be added to a liquefied starch or maltodextrin slurry at a treatment level in a range from about 0.0025% by weight to about 0.01% by weight based on dissolved solids. In one embodiment, the polypeptide as defined herein is immobilized, and the liquefied starch or maltodextrin substrate is passed over the immobilized polypeptide as defined herein and converted to product in a continuous reaction. In this embodiment, the polypeptide as defined herein may be immobilized with additional enzymes, such as a pullulanase.

The production of maltotetraose may further comprise contacting the liquefied starch or other source of maltodextrins with an isoamylase, a protease, a cellulase, a hemicellulase, a lipase, a cutinase, or any combination thereof.

Also provided is a method of making a saccharide (e.g., maltotetraose) syrup, comprising adding a polypeptide variant as defined herein or a composition comprising the variant to a starch liquefact and saccharifying the starch liquefact to form the saccharide syrup. The polypeptide variant as defined herein may be added to the starch liquefact in a range from about 0.001% by weight to about 0.1% by weight based on dissolved solids. In one embodiment, the variant is added to the starch liquefact in a range from about 0.0025% by weight to about 0.01% by weight based on dissolved solids. The units of concentration also are expressed herein as kg of polypeptide variant per metric ton of dry solids (MTDS), where 1 kg/MTDS=0.1% by weight dissolved solids. The liquefied starch solution may be a slurry of liquefied starch at about 20-35% w/w dry solids. The starch may be obtained from corns, cobs, wheat, barley, rye, milo, sago, cassava, tapioca, sorghum, rice, peas, bean, banana, or potatoes. The starch liquefact may be saccharified at about 55° C. to about 65° C. such at about 60° C. to about 65° C. The starch liquefact may be saccharified at about pH 5.0 to about pH 7.0. A pullulanase, isoamylase, pullulanase, protease, cellulase, hemicellulase, lipase, cutinase, or any combination thereof, may be added with the polypeptide variant to the starch liquefact. In one embodiment, the saccharide syrup may be fermented to produce ethanol. The saccharide syrup produced by the method may comprise at least about 40%, about 45%, about 50%, about 55%, or about 60% by weight maltotetraose based on total saccharide content.

In another aspect a method of making a saccharide syrup, including adding a polypeptide variant as defined herein and an alpha-amylase to granular starch and hydrolyzing the granular starch to form the saccharide syrup is provided. In one embodiment, the granular starch liquefact is produced by an alpha-amylase. In one embodiment, the granular starch liquefact is an acid produced liquefact In one embodiment the polypeptide variant as defined herein is added to the granular starch in a range from about 0.001% by weight to about 0.1% by weight based on dissolved solids. In another embodiment the polypeptide variant as defined herein is added to the granular starch in a range from about 0.0025% by weight to about 0.01% by weight based on dissolved solids. The granular starch can be obtained from starch from corns, cobs, wheat, barley, rye, milo, sago, cassava, tapioca, sorghum, rice, peas, bean, banana, or potatoes.

In a particular embodiment the granular starch is saccharified at 55° C. to 65° C. such as 60° C. to 65° C. In another embodiment the granular starch is saccharified at pH 5.0 to pH 7.0. It is envisioned that the method can also include fermenting the saccharide syrup to produce ethanol.

In one embodiment the method includes a step of adding an enzyme having debranching activity to the granular starch. The enzyme having debranching activity can include but is not limited to an isoamylase, a pullulanase, an isopullulanase, a neopullulanase or any combination thereof. It is also envisioned that the method can optionally include a further step of adding a protease, a cellulase, a hemicellulase, a lipase, a cutinase, a pectate liase or any combination thereof to the granular starch.

In one embodiment the saccharide syrup includes at least 35% by weight maltotetraose based on total saccharide content. Alternatively, the saccharide syrup includes at least 45% by weight maltotetraose based on total saccharide content. In another embodiment the saccharide syrup includes at least 50% by weight maltotetraose based on total saccharide content. In a further embodiment the saccharide syrup includes from 45% by weight to 60% by weight maltotetraose based on total saccharide content.

It is envisioned that the polypeptide variant as defined herein of the method can be immobilized.

In another aspect a method is provided for making IMO, including adding a) a polypeptide variant as defined herein, b) an alpha-amylase, and c) a transglucosidase to starch in the form of a starch liquefact or granular starch and saccharifying the starch to form IMO. It is envisioned that the IMO can be formed at an IMO number of at least 30, at least 40 and/or at least 45. In one embodiment the starch is obtained from corns, cobs, wheat, barley, rye, milo, sago, cassava, tapioca, sorghum, rice, peas, bean, banana, or potatoes.

In another aspect a method is provided for making IMO, including adding a) a polypeptide variant, b) an alpha-amylase, and c) a transglucosidase to starch in the form of a starch liquefact or granular starch and saccharifying the starch to form IMO. Any of a number of transgucosidase enzymes (TG) can be use, for example, TRANSGLUCOSIDASE L-500® (Danisco US Inc., Genencor Division).

It is envisioned that the IMO can be formed at an IMO number of at least 30, at least 40 and/or at least 45. In one embodiment the starch is obtained from corns, cobs, wheat, barley, rye, milo, sago, cassava, tapioca, sorghum, rice, peas, bean, banana, or potatoes.

Yeast typically from *Saccharomyces* spp. is added to the mash and the fermentation is ongoing for 24-96 hours, such as typically 35-60 hours. The temperature is between about 26-34° C., typically at about 32° C., and the pH is from about pH 3-6, typically around about pH 4-5.

In one embodiment, a batch fermentation process is used in a closed system, where the composition of the medium is set at the beginning of the fermentation and is not altered during the fermentation. At the beginning of the fermentation, the medium is inoculated with the desired microbial organism(s). In this method, fermentation is permitted to occur without the addition of any components to the system. Typically, a batch fermentation qualifies as a "batch" with respect to the addition of the carbon source, and attempts are often made to control factors such as pH and oxygen concentration. The metabolite and biomass compositions of the batch system change constantly up to the time the fermentation is stopped. Within batch cultures, cells progress through a static lag phase to a high growth log phase and finally to a stationary phase, where growth rate is diminished or halted. If untreated, cells in the stationary phase eventually die. In general, cells in log phase are responsible for the bulk of production of product.

Continuous fermentation is an open system where a defined fermentation medium is added continuously to a bioreactor, and an equal amount of conditioned medium is removed simultaneously for processing. Continuous fermentation generally maintains the cultures at a constant high density, where cells are primarily in log phase growth. Continuous fermentation allows for the modulation of one or more factors that affect cell growth and/or product concentration. For example, in one embodiment, a limiting nutrient, such as the carbon source or nitrogen source, is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

A suitable variation on the standard batch system is the "fed-batch fermentation" system. In this variation of a typical batch system, the substrate is added in increments as the fermentation progresses. Fed-batch systems are useful when catabolite repression likely inhibits the metabolism of the cells and where it is desirable to have limited amounts of substrate in the medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are common and well known in the art.

Following the fermentation, the mash is distilled to extract the ethanol. The ethanol obtained according to the process of the disclosure may be used as, e.g., fuel ethanol; drinking ethanol, i.e., potable neutral spirits or industrial ethanol. Left over from the fermentation is the grain, which is typically used for animal feed, either in liquid form or dried. Further details on how to carry out liquefaction, saccharification, fermentation, distillation, and recovery of ethanol are well known to the skilled person. According to the process of the disclosure, the saccharification and fermentation may be carried out simultaneously or separately.

In one aspect, compositions, including food additives, food products, bakery products, improver compositions, feed products including animal feeds, etc comprising such altered variants as described herein, such as those which have non-maltogenic exoamylase activity, as well as methods of making and using such polypeptides and the compositions are provided.

As noted above, the variant polypeptides as described herein may comprise one or more improved handling properties, preferably improved baking properties. Thus, the variant polypeptides as described herein may provide that the food products so treated have one or more of (preferably all of) a lower firmness, a higher resilience, a higher cohesiveness, a lower crumbliness or a higher foldability. Such improved handling or baking properties exhibited by the variant polypeptides as described herein are described in further detail below. In one aspect, a variant, in which the half life ($t\frac{1}{2}$), preferably at 60 degrees C., is increased by 15% or more, preferably 50% or more, most preferably 100% or more, compared to the amino acid sequence of SEQ ID NO: 1, is provided.

In one aspect, a variant as described herein, in which a food product treated with the variant has any one or more, preferably all of the following properties: (a) lower firmness; (b) higher resilience; (c) higher cohesiveness; (d) lower crumbliness; and (e) higher foldability compared to a food product which has been treated with the amino acid sequence of SEQ ID NO: 1, is provided.

In one aspect, a variant as described herein, in which the resilience, cohesiveness or foldability of the food product is independently increased by 15% or more, preferably 50% or more, most preferably 100% or more, compared to a food product which has been treated with the amino acid sequence of SEQ ID NO: 1, is provided.

In one aspect, a variant as described herein, in which each of resilience cohesiveness and foldability of a food product treated with the variant is increased compared to a food product which has been treated with the amino acid sequence of SEQ ID NO: 1, is provided.

In one aspect, a variant as described herein, in which the firmness or the crumbliness of the food product is independently decreased by 15% or more, preferably 50% or more, most preferably 100% or more, relative to a food product which has been treated with the amino acid sequence of SEQ ID NO: 1, is provided.

In one aspect, a variant as described herein, in which each of the firmness and crumblines of a food product treated with the polypeptide is decreased compared to a food product which has been treated with the amino acid sequence of SEQ ID NO: 1 is provided.

In one aspect, a variant as described herein comprising a fragment of at least 20 residues of a polypeptide as set out in the claims, in which the polypeptide has non-maltogenic exoamylase activity, is provided.

In one aspect, a variant as described herein has non-maltogenic exoamylase activity. Such as activity may be determined by the methods described in U.S. Pat. No. 6,667,065 which is incorporated by reference herein.

In one aspect, the treatment of food products, particularly doughs and bakery products with such polypeptides, and such that the food products exhibit the desired qualities set out above are provided.

In one aspect, a process for treating a starch comprising contacting the starch with a variant as described herein and allowing the polypeptide to generate from the starch one or more linear products, is provided. In one aspect, the use of a variant as described herein in preparing a food or feed product, is provided. In one aspect, a process of preparing a food or feed product comprising admixing a variant as described herein with a food or feed ingredient, is provided. In one aspect, the use, or a process, in which the food product comprises a dough or a dough product, preferably a processed dough product, is provided. In one aspect, the use or process, in which the food product is a bakery product, is provided. In one aspect, a process for making a bakery product comprising: (a) providing a starch medium; (b) adding to the starch medium a variant as described herein; and (c) applying heat to the starch medium during or after step (b) to produce a bakery product, is provided. In one aspect, a food product, feed product, dough product or a bakery product obtained by a process as defined in the claims, is provided.

In one aspect, the use of a variant as described herein, in a dough product to retard or reduce staling, preferably detrimental retrogradation, of the dough product, is provided.

In one aspect, the use of a variant as described herein, in a dough product to improve any one or more of firmness, resilience, cohesiveness, crumbliness or foldability of the dough product, is provided.

In one aspect, a combination of a variant as described herein, together with any one or more of the following:
  a) maltogenic alpha-amylase also called glucan 1,4-α-maltohydrolase (EC 3.2.1.133) from *Bacillus stearothermophilus*, or a variant, homologue, or mutants thereof which have maltogenic alpha-amylase activity;
  b) a bakery xylanase (EC 3.2.1.8) from e.g. *Bacillus* sp., *Aspergillus* sp., *Thermomyces* sp. or *Trichoderma* sp.;
  c) α-amylase (EC 3.2.1.1) from *Bacillus amyloliqufaciens* or from *Aspergillus* sp. or a variant, homologue, or mutants thereof which have alpha-amylase activity; and d) a lipase such as glycolipase from *Fusarium heterosporum*, is provided.

The a variants as described herein preferably comprise one or more improved handling properties compared to a parent polypeptide or a wild type polypeptide, such as a polypeptide of SEQ ID NO:1 or SEQ ID NOs: 2, 4, 6, 8 or 10, preferably SEQ ID NO:1. The improved handling properties may in preferred embodiments comprise improved baking properties.

Thus, the variant as described herein are in one aspect such that a food product treated with the variant polypeptide has an improved handling or preferably baking property compared to a food product which has been treated with a parent polypeptide or a wild type polypeptide such as a polypeptide of SEQ ID NO:1 or SEQ ID NOs: 2, 4, 6, 8 or 10, preferably SEQ ID NO:1. The handling or baking property may be selected from the group consisting of: firmness, resilience, cohesiveness, crumbliness and foldability.

These handling properties may be tested by any means known in the art. For example, firmness, resilience and cohesiveness may be determined by analysing bread slices by Texture Profile Analysis using for example a Texture Analyser, as e.g. described in 11.

The variants described here are in one aspect such that a food product treated with the variant polypeptide has lower firmness compared to a food product which has been treated with a parent polypeptide or a wild type polypeptide such as a polypeptide of SEQ ID NO:1 or SEQ ID NOs: 2, 4, 6, 8 or 10, preferably SEQ ID NO:1.

The firmness is in preferred embodiments inversely correlated with the softness of the food product; thus, a higher softness may reflect a lower firmness, and vice versa.

Firmness may be measured by the "Firmness Evaluation Protocol" set out in example 11.

In one aspect, the variants described herein are such that a food product treated with the variant polypeptide has a 10%, 20%, 30%, 40%, 50%, 60%, 70%, 80%, 90%, 100%, 200% or more lower firmness compared to a food product which has been treated with a parent polypeptide or a wild type polypeptide such as a polypeptide of SEQ ID NO:1 or SEQ ID NOs: 2, 4, 6, 8 or 10, preferably SEQ ID NO:1. A food product treated with the variant polypeptides disclosed herein may have a 1.1×, 1.5×, 2×, 3×, 4×, 5×, 6×, 7×, 8×, 9×, 10× or more lower firmness compared to a food product which has been treated with a parent polypeptide or a wild type polypeptide such as a polypeptide of SEQ ID NO:1 or SEQ ID NOs: 2, 4, 6, 8 or 10, preferably SEQ ID NO:1.

In one aspect, the variants described herein are such that a food product treated with the variant polypeptide has a higher resilience compared to a food product which has been treated with a parent polypeptide or a wild type polypeptide such as a polypeptide of SEQ ID NO:1 or SEQ ID NOs: 2, 4, 6, 8 or 10, preferably SEQ ID NO:1.

Resilience may be measured by the "Resilience Evaluation Protocol" set out in 11.

Thus in one aspect, the variants described herein are such that a food product treated with the variant polypeptide has a 10%, 20%, 30%, 40%, 50%, 60%, 70%, 80%, 90%, 100%, 200% or more higher resilience compared to a food product which has been treated with a parent polypeptide or a wild type polypeptide such as a polypeptide of SEQ ID NO:1 or SEQ ID NOs: 2, 4, 6, 8 or 10, preferably SEQ ID NO:1. A food product treated with the variant polypeptide may have a 1.1×, 1.5×, 2×, 3×, 4×, 5×, 6×, 7×, 8×, 9×, 10× or more higher resilience compared to a food product which has been treated with a parent polypeptide or a wild type polypeptide such as a polypeptide of SEQ ID NO:1 or SEQ ID NOs: 2, 4, 6, 8 or 10, preferably SEQ ID NO:1.

In one aspect, the variants described herein are such that a food product treated with the variant polypeptide has higher cohesiveness compared to a food product which has been treated with a parent polypeptide or a wild type polypeptide such as a polypeptide of SEQ ID NO:1 or SEQ ID NOs: 2, 4, 6, 8 or 10, preferably SEQ ID NO:1.

Cohesiveness may be measured by the "Cohesiveness Evaluation Protocol" set out 11.

Thus in one aspect, the variants described here are such that a food product treated with the variant polypeptide as disclosed herein has a 10%, 20%, 30%, 40%, 50%, 60%, 70%, 80%, 90%, 100%, 200% or more higher cohesiveness compared to a food product which has been treated with a parent polypeptide or a wild type polypeptide such as a polypeptide of SEQ ID NO:1 or SEQ ID NOs: 2, 4, 6, 8 or 10, preferably SEQ ID NO:1. A food product treated with the variant polypeptide may have a 1.1×, 1.5×, 2×, 3×, 4×, 5×, 6×, 7×, 8×, 9×, 10× or more higher cohesiveness compared to a food product which has been treated with a parent polypeptide or a wild type polypeptide such as a polypeptide of SEQ ID NO:1 or SEQ ID NOs: 2, 4, 6, 8 or 10, preferably SEQ ID NO:1.

In one aspect, the variants described here are such that a food product treated with the variant polypeptide has lower crumbliness compared to a food product which has been treated with a parent polypeptide or a wild type polypeptide such as a polypeptide of SEQ ID NO:1 or SEQ ID NOs: 2, 4, 6, 8 or 10, preferably SEQ ID NO:1.

Crumbliness may be measured by the "Crumbliness Evaluation Protocol" set out in Example 13.

Thus in one aspect, the variants described here are such that a food product treated with the variant polypeptide has a 10%, 20%, 30%, 40%, 50%, 60%, 70%, 80%, 90%, 100%, 200% or more lower crumbliness compared to a food product which has been treated with a parent polypeptide or a wild type polypeptide such as a polypeptide of SEQ ID NO:1 or SEQ ID NOs: 2, 4, 6, 8 or 10, preferably SEQ ID NO:1. A food product treated with the variant polypeptide may have a 1.1×, 1.5×, 2×, 3×, 4×, 5×, 6×, 7×, 8×, 9×, 10× or more lower crumbliness compared to a food product which has been treated with a parent polypeptide or a wild type polypeptide such as a polypeptide of SEQ ID NO:1 or SEQ ID NOs: 2, 4, 6, 8 or 10, preferably SEQ ID NO:1.

In one aspect, the variants described here are such that a food product treated with the variant polypeptide has higher foldability compared to a food product which has been treated with a parent polypeptide or a wild type polypeptide such as a polypeptide of SEQ ID NO:1 or SEQ ID NOs: 2, 4, 6, 8 or 10, preferably SEQ ID NO:1.

Foldability is preferably measured by the "Foldability Evaluation Protocol" set out in Example 14.

Thus, the variants described here are such that a food product treated with the variant polypeptide has a 10%, 20%, 30%, 40%, 50%, 60%, 70%, 80%, 90%, 100%, 200% or more higher foldability compared to a food product which has been treated with a parent polypeptide or a wild type polypeptide such as a polypeptide of SEQ ID NO:1 or SEQ ID NOs: 2, 4, 6, 8 or 10, preferably SEQ ID NO:1. A food product treated with the variant polypeptide may have a 1.1×, 1.5×, 2×, 3×, 4×, 5×, 6×, 7×, 8×, 9×, 10× or more higher foldability compared to a food product which has been treated with a parent polypeptide or a wild type polypeptide such as a polypeptide of SEQ ID NO:1 or SEQ ID NOs: 2, 4, 6, 8 or 10, preferably SEQ ID NO:1.

In one aspect, the use of the variant polypeptides described here in combination with a xylanase for improving foldability are provided.

Further, a method for preparing a food product, the method comprising: (a) obtaining a non-maltogenic exoamylase; (b) introducing a mutation at any one or more of the positions of the non-maltogenic exoamylase as set out in this document; (c) admixing the resulting polypeptide with a food ingredient is provided.

The variant polypeptides may be used to enhance the volume of bakery products such as bread. While not wishing to be bound by any particular theory, we believe that this results from the reduction in viscosity of the dough during heating (such as baking) as a result of the amylase shortening amylose molecules. This enables the carbon dioxide generated by fermentation to increase the size of the bread with less hindrance.

Thus, food products comprising or treated with variant polypeptides are expanded in volume when compared to products which have not been so treated, or treated with parent polypeptides such as a polypeptide of SEQ ID NO:1 or SEQ ID NOs: 2, 4, 6, 8 or 10, preferably SEQ ID NO:1. In other words, the food products have a larger volume of air per volume of food product. Alternatively, or in addition, the food products treated with variant polypeptides as described herein have a lower density, or weight (or mass) per volume ratio. In particularly preferred embodiments, the variant polypeptides are used to enhance the volume of bread. Volume enhancement or expansion is beneficial because it reduces the gumminess or starchiness of foods. Light foods are preferred by consumers, and the customer experience is enhanced. In preferred embodiments, the use of variant polypeptides enhances the volume by 10%, 20%, 30% 40%, 50% or more.

The variant polypeptides and nucleic acids described here may be used as—or in the preparation of—a food. In particular, they may be added to a food, i.e., as a food additive. The term "food" is intended to include both prepared food, as well as an ingredient for a food, such as a flour. In a preferred aspect, the food is for human consumption. The food may be in the form of a solution or as a solid—depending on the use and/or the mode of application and/or the mode of administration.

The variant polypeptides and nucleic acids may be used as a food ingredient. As used herein the term "food ingredient" includes a formulation, which is or can be added to functional foods or foodstuffs and includes formulations which can be used at low levels in a wide variety of products that require, for example, acidifying or emulsifying. The food ingredient may be in the form of a solution or as a solid—depending on the use and/or the mode of application and/or the mode of administration.

The variant polypeptides and nucleic acids disclosed here may be—or may be added to—food supplements. The variant polypeptides and nucleic acids disclosed here may be—or may be added to—functional foods. As used herein, the term "functional food" means food which is capable of providing not only a nutritional effect and/or a taste satisfaction, but is also capable of delivering a further beneficial effect to consumer. Although there is no legal definition of a functional food, most of the parties with an interest in this area agree that they are foods marketed as having specific health effects.

The variant polypeptides may also be used in the manufacture of a food product or a foodstuff. Typical foodstuffs include dairy products, meat products, poultry products, fish products and dough products. The dough product may be any processed dough product, including fried, deep fried, roasted, baked, steamed and boiled doughs, such as steamed bread and rice cakes. In highly preferred embodiments, the food product is a bakery product.

Preferably, the foodstuff is a bakery product. Typical bakery (baked) products include bread—such as loaves, rolls, buns, bagels, pizza bases etc. pastry, pretzels, tortillas, cakes, cookies, biscuits, crackers etc.

The food products preferably benefit from one or more of the improved handling or baking properties of the variant polypeptides described here. The improved handling or baking property may be selected from the group consisting of: improved firmness, improved resilience, improved cohesiveness, improved crumbliness and improved foldability.

Further in one aspect, a method of modifying a food additive comprising a non-maltogenic exoamylase, the method comprising introducing a mutation at any one or more of the positions of the non-maltogenic exoamylase as set out in this document is provided. The same method can be used to modify a food ingredient, or a food supplement, a food product, or a foodstuff.

In one aspect, the use of variant polypeptides that are capable of retarding the staling of starch media, such as starch gels are provided. The variant polypeptides are especially capable of retarding the detrimental retrogradation of starch.

Most starch granules are composed of a mixture of two polymers: an essentially linear amylose and a highly branched amylopectin. Amylopectin is a very large, branched molecule consisting of chains of α-D-glucopyranosyl units joined by (1-4) linkages, wherein said chains are attached by α-D-(1-6) linkages to form branches. Amylopectin is present in all natural starches, constituting about 75% of most common starches. Amylose is essentially a linear chain of (1-4) linked α-D-glucopyranosyl units having few α-D-(1-6) branches. Most starches contain about 25% amylose.

Starch granules heated in the presence of water undergo an order-disorder phase transition called gelatinization, where liquid is taken up by the swelling granules. Gelatinization temperatures vary for different starches. Upon cooling of freshly baked bread the amylose fraction, within hours, retrogrades to develop a network. This process is beneficial in that it creates a desirable crumb structure with a low degree of firmness and improved slicing properties. More gradually crystallisation of amylopectin takes place within the gelatinised starch granules during the days after baking. In this process amylopectin is believed to reinforce the amylose network in which the starch granules are embedded. This reinforcement leads to increased firmness of the bread crumb. This reinforcement is one of the main causes of bread staling.

It is known that the quality of baked products gradually deteriorates during storage. As a consequence of starch recystallisation (also called retrogradation), the water-holding capacity of the crumb is changed with important implications on the organoleptic and dietary properties. The crumb looses softness and elasticity and becomes firm and crumbly. The increase in crumb firmness is often used as a measure of the staling process of bread.

The rate of detrimental retrogradation of amylopectin depends on the length of the side chains of amylopectin. Thus, enzymatic hydrolysis of the amylopectin side chains, for example, by variant polypeptides as described herein having non-maltogenic exoamylase activity, can markedly reduce their crystallisation tendencies.

Accordingly, in one aspect the use of variant polypeptides as described here when added to the starch at any stage of its processing into a food product e.g., before during or after baking into bread can retard or impede or slow down the retrogradation. Such use is described in further detail below.

In one aspect, a method of improving the ability of a non-maltogenic exoamylase to prevent staling, preferably detrimental retrogradation, of a dough product, the method comprising introducing a mutation at any one or more of the positions of the non-maltogenic exoamylase as set out in this document are provided.

For evaluation of the antistaling effect of the variant polypeptides such a variant having non-maltogenic exoamylase activity described here, the crumb firmness can be measured 1, 3 and 7 days after baking by means of an Instron 4301 Universal Food Texture Analyzer or similar equipment known in the art.

Another method used traditionally in the art and which is used to evaluate the effect on starch retrogradation of a variant polypeptide such as a variant having exoamylase activity is based on DSC (differential scanning calorimetry). Here, the melting enthalpy of retrograded amylopectin in bread crumb or crumb from a model system dough baked with or without enzymes (control) is measured. The DSC equipment applied may be a Mettler-Toledo DSC 820 run with a temperature gradient of 10° C. per min. from 20 to 95° C. For preparation of the samples 10-20 mg of crumb are weighed and transferred into Mettler-Toledo aluminium pans which then are hermetically sealed.

The model system doughs may contain standard wheat flour and optimal amounts of water or buffer with or without the polypeptide variant. They are mixed in a 10 or 50 g Brabender Farinograph for 6 or 7 min., respectively. Samples of the doughs are placed in glass test tubes (15*0.8 cm) with a lid. These test tubes are subjected to a baking process in a water bath starting with 30 min. incubation at 33° C. followed by heating from 33 to 95° C. with a gradient of 1.1° C. per min. and finally a 5 min. incubation at 95° C. Subsequently, the tubes are stored in a thermostat at 20° C. prior to DSC analysis.

In one embodiment, the variants described here have a reduced melting enthalpy, compared to the control. In a further embodiment, the variants have a 10% or more reduced melting enthalpy. In yet a further aspect, they have a 20% or more, 30%, 40%, 50%, 60%, 70%, 80%, 90% or more reduced melting enthalpy when compared to the control.

In one aspect, the use of variant polypeptides in the preparation of food products, in particular, starch products is provided. The method comprises forming the starch product by adding a non-maltogenic exoamylase enzyme such as a variant polypeptide, to a starch medium. If the starch medium is a dough, then the dough is prepared by mixing together flour, water, the non-maltogenic exoamylase which is a variant polypeptide as described herein and optionally other possible ingredients and additives.

The term "starch" should be taken to mean starch per se or a component thereof, especially amylopectin. The term "starch medium" means any suitable medium comprising starch. The term "starch product" means any product that contains or is based on or is derived from starch. Preferably, the starch product contains or is based on or is derived from starch obtained from wheat flour. The term "flour" as used herein is a synonym for the finely-ground meal of wheat or other grain. Preferably, however, the term means flour obtained from wheat per se and not from another grain. Thus, and unless otherwise expressed, references to "wheat flour" as used herein preferably mean references to wheat flour per se as well as to wheat flour when present in a medium, such as a dough.

A preferred flour is wheat flour or rye flour or mixtures of wheat and rye flour. However, dough comprising flour derived from other types of cereals such as for example from rice, maize, barley, and durra are also contemplated. Preferably, the starch product is a bakery product. More preferably, the starch product is a bread product. Even more preferably, the starch product is a baked farinaceous bread product. The term "baked farinaceous bread product" refers to any baked product based on a dough obtainable by mixing flour, water, and a leavening agent under dough forming conditions. Further components can of course be added to the dough mixture.

Thus, if the starch product is a baked farinaceous bread product, then the process comprises mixing—in any suitable order—flour, water, and a leavening agent under dough forming conditions and further adding a variant polypeptide as described herein, optionally in the form of a premix. The leavening agent may be a chemical leavening agent such as sodium bicarbonate or any strain of *Saccharomyces cerevisiae* (Baker's Yeast).

The variant polypeptide as described herein can be added together with any dough ingredient including the water or dough ingredient mixture or with any additive or additive mixture. The dough can be prepared by any conventional dough preparation method common in the baking industry or in any other industry making flour dough based products.

Baking of farinaceous bread products such as for example white bread, bread made from bolted rye flour and wheat flour, rolls and the like is typically accomplished by baking the bread dough at oven temperatures in the range of from 180 to 250° C. for about 15 to 60 minutes. During the baking process a steep temperature gradient (200 to 120° C.) is prevailing in the outer dough layers where the characteristic crust of the baked product is developed. However, owing to heat consumption due to steam generation, the temperature in the crumb is only close to 100° C. at the end of the baking process.

A process for making a bread product comprising: (a) providing a starch medium; (b) adding to the starch medium a variant polypeptide as described in this document; and (c) applying heat to the starch medium during or after step (b) to produce a bread product is provided. A process for making a bread product comprising adding to a starch medium a variant polypeptide as described is also provided.

In one aspect, the variant polypeptide can be added as a liquid preparation or as a dry pulverulent composition either comprising the enzyme as the sole active component or in admixture with one or more additional dough ingredient or dough additive.

In a further aspect, the improver compositions, which include bread improving compositions and dough improving compositions are provided. These comprise a variant polypeptide, optionally together with a further ingredient, or a further enzyme, or both.

In one aspect, an improver composition for a dough, in which the improver composition comprises a variant as set out in any of the claims, and at least one further dough ingredient or dough additive, is provided.

In one aspect, a composition comprising a flour and a variant as set out in any of the claims, is provided.

In a further aspect, the use of such a bread and dough improving compositions in baking is provided. In a further aspect, a baked product or dough obtained from the bread improving composition or dough improving composition is provided. In another aspect, a baked product or dough obtained from the use of a bread improving composition or a dough improving composition is provided.

A dough may be prepared by admixing flour, water, a dough improving composition comprising variant polypeptide (as described above) and optionally other ingredients and additives.

The dough improving composition can be added together with any dough ingredient including the flour, water or optional other ingredients or additives. The dough improving composition can be added before the flour or water or optional other ingredients and additives. The dough improving composition can be added after the flour or water, or optional other ingredients and additives. The dough can be prepared by any conventional dough preparation method common in the baking industry or in any other industry making flour dough based products.

The dough improving composition can be added as a liquid preparation or in the form of a dry powder composition either comprising the composition as the sole active component or in admixture with one or more other dough ingredients or additive.

The amount of the variant polypeptide that is added is normally in an amount which results in the presence in the finished dough of 50 to 100,000 units per kg of flour, preferably 100 to 50,000 units per kg of flour. Preferably, the amount is in the range of 200 to 20,000 units per kg of flour. Alternatively, the variant polypeptide is added in an amount which results in the presence in the finished dough of 0.02-50 ppm of enzyme based on flour (0.02-50 mg enzyme per kg of flour), preferably 0.2-10 ppm.

In the present context, 1 unit of the non-maltogenic exoamylase is defined as the amount of enzyme which releases hydrolysis products equivalent to 1 μmol of reducing sugar per min. when incubated at 50 degrees C. in a test tube with 4 ml of 10 mg/ml waxy maize starch in 50 mM MES, 2 mM calcium chloride, pH 6.0 as described hereinafter.

The dough as described here generally comprises wheat meal or wheat flour and/or other types of meal, flour or starch such as corn flour, corn starch, maize flour, rice flour, rye meal, rye flour, oat flour, oat meal, soy flour, sorghum meal, sorghum flour, potato meal, potato flour or potato starch. The dough may be fresh, frozen, or part-baked.

The dough may be a leavened dough or a dough to be subjected to leavening. The dough may be leavened in various ways, such as by adding chemical leavening agents, e.g., sodium bicarbonate or by adding a leaven (fermenting dough), but it is preferred to leaven the dough by adding a suitable yeast culture, such as a culture of *Saccharomyces cerevisiae* (baker's yeast), e.g. a commercially available strain of *S. cerevisiae*.

The dough may comprise fat such as granulated fat or shortening. The dough may further comprise a further emulsifier such as mono- or diglycerides, sugar esters of fatty acids, polyglycerol esters of fatty acids, lactic acid esters of monoglycerides, acetic acid esters of monoglycerides, polyoxethylene stearates, or lysolecithin.

A pre-mix comprising flour together with the combination as described herein are furthermore provided. The pre-mix may contain other dough-improving and/or bread-improving additives, e.g. any of the additives, including enzymes, mentioned herein.

In order to improve further the properties of the baked product and impart distinctive qualities to the baked product further dough ingredients and/or dough additives may be incorporated into the dough. Typically, such further added components may include dough ingredients such as salt, grains, fats and oils, sugar or sweetener, dietary fibres, protein sources such as milk powder, gluten soy or eggs and dough additives such as emulsifiers, other enzymes, hydrocolloids, flavouring agents, oxidising agents, minerals and vitamins The emulsifiers are useful as dough strengtheners and crumb softeners. As dough strengtheners, the emulsifiers can provide tolerance with regard to resting time and tolerance to shock during the proofing. Furthermore, dough strengtheners will improve the tolerance of a given dough to variations in the fermentation time. Most dough strengtheners also improve on the oven spring which means the increase in volume from the proofed to the baked goods. Lastly, dough strengtheners will emulsify any fats present in the recipe mixture.

Suitable emulsifiers include lecithin, polyoxyethylene stearat, mono- and diglycerides of edible fatty acids, acetic acid esters of mono- and diglycerides of edible fatty acids, lactic acid esters of mono- and diglycerides of edible fatty acids, citric acid esters of mono- and diglycerides of edible fatty acids, diacetyl tartaric acid esters of mono- and diglycerides of edible fatty acids, sucrose esters of edible fatty acids, sodium stearoyl-2-lactylate, and calcium stearoyl-2-lactylate.

The further dough additive or ingredient can be added together with any dough ingredient including the flour, water or optional other ingredients or additives, or the dough improving composition. The further dough additive or ingredient can be added before the flour, water, optional other ingredients and additives or the dough improving composition. The further dough additive or ingredient can be added after the flour, water, optional other ingredients and additives or the dough improving composition.

The further dough additive or ingredient may conveniently be a liquid preparation. However, the further dough additive or ingredient may be conveniently in the form of a dry composition.

In one aspect the further dough additive or ingredient is at least 1% the weight of the flour component of dough. In a further aspect, the further dough additive or ingredient is at least 2%, preferably at least 3%, preferably at least 4%, preferably at least 5%, preferably at least 6%. If the additive is a fat, then typically the fat may be present in an amount of from 1 to 5%, typically 1 to 3%, more typically about 2%.

For the commercial and home use of flour for baking and food production, it is important to maintain an appropriate level of α-amylase activity in the flour. A level of activity that is too high may result in a product that is sticky and/or doughy and therefore unmarketable. Flour with insufficient α-amylase activity may not contain enough sugar for proper yeast function, resulting in dry, crumbly bread, or baked products. Accordingly, a variant as described herein, by itself or in combination with another α-amylase(s) or another variant, may be added to the flour to augment the level of endogenous α-amylase activity in flour. The variant in this embodiment can have a temperature optimum in the presence of starch in the ranges of about 30-90° C., 40-80° C., 40 50° C., 45-65° C., or 50-60° C., for example. The pH optimum in a 1% solution of soluble starch may be between pH 4.5 to 6.0, for example.

Grains, such as barley, oats, wheat, as well as plant components, such as corn, hops, and rice, also are used for brewing, both in industry and for home brewing. The components used in brewing may be unmalted or may be malted, i.e., partially germinated, resulting in an increase in the levels of enzymes, including α-amylase. For successful brewing, adequate levels of α-amylase enzyme activity are necessary to ensure the appropriate levels of sugars for fermentation. A variant, by itself or in combination with another α-amylase(s), accordingly may be added to the components used for brewing.

As used herein, the term "flour" means milled or ground cereal grain. The term "flour" also may mean Sago or tuber products that have been ground or mashed. In some embodiments, flour may also contain components in addition to the milled or mashed cereal or plant matter. An example of an additional component, although not intended to be limiting, is a leavening agent. Cereal grains include wheat, oat, rye, and barley. Tuber products include tapioca flour, cassava flour, and custard powder. The term "flour" also includes ground corn flour, maize-meal, rice flour, whole-meal flour, self-rising flour, tapioca flour, cassava flour, ground rice, enriched flower, and custard powder.

As used herein, the term "stock" means grains and plant components that are crushed or broken. For example, barley used in beer production is a grain that has been coarsely ground or crushed to yield a consistency appropriate for producing a mash for fermentation. As used herein, the term "stock" includes any of the aforementioned types of plants and grains in crushed or coarsely ground forms. The methods described herein may be used to determine α-amylase activity levels in both flours and stock.

One or more further enzymes may be used in combination with the variant polypeptides as described herein. Such combinations may for example be added to the food, dough preparation, foodstuff or starch composition.

Baking amylases may be from a fungus, bacterium or plant. It may a alpha-amylase (EC 3.2.1.1). The alpha-amylase may be a fungal alpha-amylase from *Aspergillus* or *Trichoderma*, e.g. from *Aspergillus oryzae*. Or it may be a alpha-amylase from *Bacillus*, e.g. *B. amyloliquefaciens* or *B. licheniformis*. Or it may be a plant beta-amylase (EC 3.2.1.2), e.g. beta-amylase from barley malt or soy bean. Or it may be an exo-amylase used for antistaling, e.g. non-maltogenic exo-amylase (EC 3.2.1.60) developed from *Pseudomonas saccharophila* maltotetrahydrolase (SEQ ID NO: 10) or maltogenic amylase (EC 3.2.1.133) developed from *Bacillus stearothermophilus* as further described below.

In one aspect, the further amylase is a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic alpha-amylase from *Bacillus* (EP 120 693) is commercially available under the trade name Novamyl (Novozymes, Denmark) and is widely used in the baking industry as an anti-staling agent due to its ability to reduce retrogradation of starch. Novamyl is described in detail in International Patent Publication WO 91/04669. The maltogenic alpha-amylase Novamyl shares several characteristics with cyclodextrin glucanotransferases (CGTases), including sequence homology (Henrissat B, Bairoch A; Biochem. J., 316, 695-696 (1996)) and formation of transglycosylation products (Christophersen, C., et al., 1997, Starch, vol. 50, No. 1, 39-45). The Novamyl may in particular comprise Novamyl 1500 MG. Other documents describing Novamyl and its uses include Christophersen, C., Pedersen, S., and Christensen, T., (1993) Method for production of maltose an a limit dextrin, the limit dextrin, and use of the limit dextrin. Denmark, and WO 95/10627. It is further described in U.S. Pat. No. 4,598, 048 and U.S. Pat. No. 4,604,355. Preferred examples of anti-staling amylases are exo-amylases, e.g. non-maltogenic exo-amylase or G4-amylase (EC 3.2.1.60) developed from *Pseudomonas saccharophila* maltotetraohydrolase having SEQ ID NO: 1 or maltogenic amylase (EC 3.2.1.133) developed from *Bacillus stearothermophilus* having SEQ ID NO: 51.

An antistaling amylase reduces staling after baking and leads to a reduction in firmness increase and a reduction in resilience decrease from day 1 to day 7 after baking relative to a control without enzyme. An antistaling amylase can be assayed by doing a baking trial and using texture analysis to determine firmness and resilience development over time. Texture analysis is described in example 11.

The further enzymes may be selected from, for example, any combination of the following: (a) Novamyl, or a variant, homologue, or mutants thereof which have maltogenic alpha-amylase activity; (b) a xylanase such as GRINDAMYL™ POWERBake 900 (Danisco A/S); (c) a bacterial α-amylase such as Max-Life U4 (Danisco A/S); and (d) a lipase such as GRINDAMYL™ POWERBake 4050 (Danisco A/S).

In one embodiment a variant polypeptide as described herein is used in combination with at least one enzyme selected from the list consisting of oxidoreductases, hydrolases, lipases, esterases, glycosidases, amylases, pullulanases, xylanases, cellulases, hemicellulases, starch degrading enzymes, proteases and lipoxygenases. In one embodiment, the composition comprises at least one variant polypeptide as described herein and a maltogenic amylase from *Bacillus*, as disclosed in WO91/04669. One embodiment comprises a variant polypeptide as described herein and flour.

Further enzymes that may be added to the dough include oxidoreductases, hydrolases, such as lipases and esterases as well as glycosidases like α-amylase, pullulanase, and xylanase. Oxidoreductases, such as for example glucose oxidase and hexose oxidase, can be used for dough strengthening and control of volume of the baked products and xylanases and other hemicellulases may be added to improve dough handling properties, crumb firmness and bread volume. Lipases are useful as dough strengtheners and crumb softeners and α-amylases and other amylolytic enzymes may be incorporated into the dough to control bread volume and further reduce crumb firmness.

Further enzymes that may be used may be selected from the group consisting of a cellulase, a hemicellulase, a starch degrading enzyme, a protease, a lipoxygenase.

A variant as defined herein further can be added alone or in a combination with other amylases, including other amylase variants, to prevent or retard staling, i.e., crumb firming of baked products. The amount of anti-staling amylase will typically be in the range of 0.01-10 mg of enzyme protein per kg of flour, e.g., 0.5 mg/kg ds. Additional anti-staling amylases that can be used in combination with a variant polypeptide as described herein include an endo-amylase, e.g., a bacterial endo-amylase from *Bacillus*. The additional amylase can be a maltogenic α-amylase (EC 3.2.1.133), e.g., from *Bacillus*. Novamyl® is an exemplary maltogenic α-amylase from *B. stearothermophilus* strain NCIB 11837 and is described in Christophersen et al., *Starch* 50: 39-45 (1997). Other examples of anti-staling endo-amylases include bacterial α-amylases derived from *Bacillus*, such as *B. licheniformis* or *B. amyloliquefaciens*. The anti-staling amylase may be an exo-amylase, such as β-amylase, e.g., from plant sources, such as soybean, or from microbial sources, such as *Bacillus*.

The baking composition comprising a variant polypeptide as described herein further can comprise a phospholipase. The phospholipase may have $A_1$ or $A_2$ activity to remove fatty acid from the phospholipids, forming a lysophospholipid. It may or may not have lipase activity, i.e., activity on triglyceride substrates. The phospholipase typically has a temperature optimum in the range of 30-90° C., e.g., 30-70° C. The added phospholipases can be of animal origin, for example, from pancreas, e.g., bovine or porcine pancreas, snake venom or bee venom. Alternatively, the phospholipase may be of microbial origin, e.g., from filamentous fungi, yeast or bacteria, such as the genus or species. Exemplary sources of phospholipases include *Aspergillus, A. niger; Dictyostelium, D. discoideum; Mucor, M. javanicus, M. mucedo, M. subtilissimus; Neurospora, N. crassa; Rhizomucor, R. pusillus; Rhizopus, R. arrhizus, R. japonicus, R. stolonifer; Sclerotinia, S. libertiana; Trichophyton, T. rubrum; Whetzelinia, W.*

*sclerotiorum; Bacillus, B. megaterium, B. subtilis; Citrobacter, C. freundii; Enterobacter, E. aerogenes, E. cloacae; Edwardsiella, E. tarda; Etwinia, E. herbicola; Escherichia, E. coli; Klebsiella, K. pneumoniae; Proteus, P. vulgaris; Providencia, P. stuartii; Salmonella, S. typhimurium; Serratia, S. liquefasciens, S. marcescens; Shigella, S. flexneri; Streptomyces, S. violeceoruber; Yersinia, Y. enterocolitica; Fusarium*, and *F. oxysporum* (strain DSM 2672, for example).

The phospholipase is added in an amount that improves the softness of the bread during the initial period after baking, particularly the first 24 hours. The amount of phospholipase will typically be in the range of about 0.01-10 mg of enzyme protein per kg of flour, e.g., 0.1-5 mg/kg. Phospholipase activity generally will be in the range of about 20-1000 Lipase Unit (LU)/kg of flour, where a Lipase Unit is defined as the amount of enzyme required to release 1 µmol butyric acid per minute at 30° C., pH 7.0, with gum arabic as emulsifier and tributyrin as substrate.

Compositions of dough generally comprise wheat meal or wheat flour and/or other types of meal, flour or starch such as corn flour, cornstarch, rye meal, rye flour, oat flour, oatmeal, soy flour, sorghum meal, sorghum flour, potato meal, potato flour or potato starch. The dough may be fresh, frozen or par-baked. The dough can be a leavened dough or a dough to be subjected to leavening. The dough may be leavened in various ways, such as by adding chemical leavening agents, e.g., sodium bicarbonate or by adding a leaven, i.e., fermenting dough. Dough also may be leavened by adding a suitable yeast culture, such as a culture of *Saccharomyces cerevisiae* (baker's yeast), e.g., a commercially available strain of *S. cerevisiae*.

The dough may also comprise other conventional dough ingredients, e.g., proteins, such as milk powder, gluten, and soy; eggs (e.g., whole eggs, egg yolks or egg whites); an oxidant, such as ascorbic acid, potassium bromate, potassium iodate, azodicarbonamide (ADA) or ammonium persulfate; an amino acid such as L-cysteine; a sugar; or a salt, such as sodium chloride, calcium acetate, sodium sulfate or calcium sulfate. The dough further may comprise fat, e.g., triglyceride, such as granulated fat or shortening. The dough further may comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyetliylene stearates, or lysolecithin. In particular, the dough can be made without addition of emulsifiers.

Optionally, an additional enzyme may be used together with the anti-staling amylase and the phospholipase. The additional enzyme may be a second amylase, such as an amyloglucosidase, a β-amylase, a cyclodextrin glucanotransferase, or the additional enzyme may be a peptidase, in particular an exopeptidase, a transglutaminase, a lipase, a cellulase, a hemicellulase, in particular a pentosanase, such as xylanase, a protease, a protein disulfide isomerase, e.g., a protein disulfide isomerase as disclosed in WO 95/00636, for example, a glycosyltransferase, a branching enzyme (1,4-α-glucan branching enzyme), a 4-α-glucanotransferase (dextrin glycosyltransferase) or an oxidoreductase, e.g., a peroxidase, a laccase, a glucose oxidase, a pyranose oxidase, a lipooxygenase, an L-amino acid oxidase or a carbohydrate oxidase. The additional enzyme(s) may be of any origin, including mammalian and plant, and particularly of microbial (bacterial, yeast or fungal) origin and may be obtained by techniques conventionally used in the art.

The xylanase is typically of microbial origin, e.g., derived from a bacterium or fungus, such as a strain of *Aspergillus*, in particular of *A. aculeatus, A. niger* (cf. WO 91/19782), *A. awamori* (e.g., WO 91/18977), or *A. tubigensis* (e.g., WO 92/01793); from a strain of *Trichoderma*, e.g., *T. reesei*, or from a strain of *Humicola*, e.g., *H. insolens* (e.g., WO 92/17573). Pentopan® and Novozym 384® are commercially available xylanase preparations produced from *Trichoderma reesei*. The amyloglucosidase may be an *A. niger* amyloglucosidase (such as AMG®). Other useful amylase products include Grindamyl® A 1000 or A 5000 (available from Danisco, Denmark) and Amylase® H or Amylase® P (available from Gist-Brocades, The Netherlands). The glucose oxidase may be a fungal glucose oxidase, in particular an *Aspergillus niger* glucose oxidase (such as Gluzyme®). An exemplary protease is Neutrase®. An exemplary lipase can be derived from strains of *Thermomyces (Humicola), Rhizomucor, Candida, Aspergillus, Rhizopus*, or *Pseudomonas*, in particular from *Thermomyces lanuginosus (Humicola lanuginosa), Rhizomucor miehei, Candida antarctica, Aspergillus niger, Rhizopus delemar* or *Rhizopus arrhizus*, or *Pseudomonas cepacia*. In specific embodiments, the lipase may be Lipase A or Lipase B derived from *Candida antarctica* as described in WO 88/02775, for example, or the lipase may be derived from *Rhizomucor miehei* as described in EP 238,023, for example, or *Humicola lanuginosa*, described in EP 305, 216, for example, or *Pseudomonas cepacia* as described in EP 214,761 and WO 89/01032, for example.

The process may be used for any kind of baked product prepared from dough, either of a soft or a crisp character, either of a white, light or dark type. Examples are bread, particularly white, whole-meal or rye bread, typically in the form of loaves or rolls, such as, but not limited to, French baguette-type bread, pita bread, tortillas, cakes, pancakes, biscuits, cookies, pie crusts, crisp bread, steamed bread, pizza and the like.

In another embodiment, a variant polypeptide as described herein may be used in a pre-mix, comprising flour together with an anti-staling amylase, a phospholipase and a phospholipid. The pre-mix may contain other dough-improving and/or bread-improving additives, e.g., any of the additives, including enzymes, mentioned above. In one aspect, the variant polypeptide as described herein is a component of an enzyme preparation comprising an anti-staling amylase and a phospholipase, for use as a baking additive.

The enzyme preparation is optionally in the form of a granulate or agglomerated powder. The preparation can have a narrow particle size distribution with more than 95% (by weight) of the particles in the range from 25 to 500 µm. Granulates and agglomerated powders may be prepared by conventional methods, e.g., by spraying the variant polypeptide as described herein onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy.

Another aspect contemplates the enveloping of particles comprising a variant polypeptide as described herein, i.e., α-amylase particles. To prepare the enveloped α-amylase particles, the enzyme is contacted with a food grade lipid in sufficient quantity to suspend all of the a amylase particles. Food grade lipids, as used herein, may be any naturally organic compound that is insoluble in water but is soluble in non-polar organic solvents such as hydrocarbon or diethyl ether. Suitable food grade lipids include, but are not limited to, triglycerides either in the form of fats or oils that are either saturated or unsaturated. Examples of fatty acids and combinations thereof which make up the saturated triglycerides include, but are not limited to, butyric (derived from milk fat), palmitic (derived from animal and plant fat), and/or stearic (derived from animal and plant fat). Examples of fatty acids and combinations thereof which make up the unsaturated triglycerides include, but are not limited to, palmitoleic (derived from animal and plant fat), oleic (derived from animal and plant fat), linoleic (derived from plant oils), and/or linolenic (derived from linseed oil). Other suitable food grade lipids include, but are not limited to, monoglycerides and diglycerides derived from the triglycerides discussed above, phospholipids and glycolipids.

The food grade lipid, particularly in the liquid form, is contacted with a powdered form of the α-amylase particles in such a fashion that the lipid material covers at least a portion of the surface of at least a majority, e.g., 100% of the α-amylase particles. Thus, each α-amylase particle is individually enveloped in a lipid. For example, all or substantially all of the α-amylase particles are provided with a thin, continuous, enveloping film of lipid. This can be accomplished by first pouring a quantity of lipid into a container, and then slurrying the α-amylase particles so that the lipid thoroughly wets the surface of each α-amylase particle. After a short period of stifling, the enveloped α-amylase particles, carrying a substantial amount of the lipids on their surfaces, are recovered. The thickness of the coating so applied to the particles of α-amylase can be controlled by selection of the type of lipid used and by repeating the operation in order to build up a thicker film, when desired.

The storing, handling and incorporation of the loaded delivery vehicle can be accomplished by means of a packaged mix. The packaged mix can comprise the enveloped α-amylase. However, the packaged mix may further contain additional ingredients as required by the manufacturer or baker. After the enveloped α-amylase has been incorporated into the dough, the baker continues through the normal production process for that product.

The advantages of enveloping the α-amylase particles are two-fold. First, the food grade lipid protects the enzyme from thermal denaturation during the baking process for those enzymes that are heat labile. Consequently, while the α-amylase is stabilized and protected during the proving and baking stages, it is released from the protective coating in the final baked good product, where it hydrolyzes the glucosidic linkages in polyglucans. The loaded delivery vehicle also provides a sustained release of the active enzyme into the baked good. That is, following the baking process, active α-amylase is continually released from the protective coating at a rate that counteracts, and therefore reduces the rate of, staling mechanisms.

In general, the amount of lipid applied to the α-amylase particles can vary from a few percent of the total weight of the α-amylase to many times that weight, depending upon the nature of the lipid, the manner in which it is applied to the α-amylase particles, the composition of the dough mixture to be treated, and the severity of the dough-mixing operation involved.

The loaded delivery vehicle, i.e., the lipid-enveloped enzyme, is added to the ingredients used to prepare a baked good in an effective amount to extend the shelf-life of the baked good. The baker computes the amount of enveloped α-amylase, prepared as discussed above, that will be required to achieve the desired anti-staling effect. The amount of the enveloped α-amylase required is calculated based on the concentration of enzyme enveloped and on the proportion of α-amylase to flour specified. A wide range of concentrations has been found to be effective, although, as has been discussed, observable improvements in anti-staling do not correspond linearly with the α-amylase concentration, but above certain minimal levels, large increases in a amylase concentration produce little additional improvement. The α-amylase concentration actually used in a particular bakery production could be much higher than the minimum necessary in order to provide the baker with some insurance against inadvertent under-measurement errors by the baker. The lower limit of enzyme concentration is determined by the minimum anti-staling effect the baker wishes to achieve.

A method of preparing a baked good may comprise: (a) preparing lipid-coated α-amylase particles, where substantially all of the α-amylase particles are coated; (b) mixing a dough containing flour; (c) adding the lipid-coated α-amylase to the dough before the mixing is complete and terminating the mixing before the lipid coating is removed from the α-amylase; (d) proofing the dough; and (e) baking the dough to provide the baked good, where the α-amylase is inactive during the mixing, proofing and baking stages and is active in the baked good.

The enveloped α-amylase can be added to the dough during the mix cycle, e.g., near the end of the mix cycle. The enveloped α-amylase is added at a point in the mixing stage that allows sufficient distribution of the enveloped α-amylase throughout the dough; however, the mixing stage is terminated before the protective coating becomes stripped from the α-amylase particle(s). Depending on the type and volume of dough, and mixer action and speed, anywhere from one to six minutes or more might be required to mix the enveloped α-amylase into the dough, but two to four minutes is average. Thus, several variables may determine the precise procedure. First, the quantity of enveloped α-amylase should have a total volume sufficient to allow the enveloped α-amylase to be spread throughout the dough mix. If the preparation of enveloped α-amylase is highly concentrated, additional oil may need to be added to the pre-mix before the enveloped α-amylase is added to the dough. Recipes and production processes may require specific modifications; however, good results generally can be achieved when 25% of the oil specified in a bread dough formula is held out of the dough and is used as a carrier for a concentrated enveloped α-amylase when added near the end of the mix cycle. In bread or other baked goods, particularly those having a low fat content, e.g., French-style breads, an enveloped α-amylase mixture of approximately 1% of the dry flour weight is sufficient to admix the enveloped α-amylase properly with the dough. The range of suitable percentages is wide and depends on the formula, finished product, and production methodology requirements of the individual baker. Second, the enveloped α-amylase suspension should be added to the mix with sufficient time for complete mixture into the dough, but not for such a time that excessive mechanical action strips the protective lipid coating from the enveloped α-amylase particles.

Also contemplated are compositions and methods of treating fabrics (e.g., to desize a textile) using a variant polypeptide as described herein. In one aspect, a method of desizing textiles, comprising contacting the variant polypeptide as described herein with a textile for a time sufficient to desize the textile, is provided.

Fabric-treating methods are well known in the art (see, e.g., U.S. Pat. No. 6,077,316). For example, in one aspect, the feel and appearance of a fabric is improved by a method comprising contacting the fabric with a variant polypeptide as described herein in a solution. In one aspect, the fabric is treated with the solution under pressure.

In one aspect, a variant polypeptide as described herein is applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. A variant polypeptide as described herein can be applied during or after the weaving to remove these sizing starch or starch derivatives. After weaving, a variant polypeptide as described herein can be used to remove the size coating before further processing the fabric to ensure a homogeneous and wash-proof result.

A variant polypeptide as described herein can be used alone or with other desizing chemical reagents and/or desizing enzymes to desize fabrics, including cotton-containing fabrics, as detergent additives, e.g., in aqueous compositions. A variant polypeptide as described herein also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of amylolytic enzymes to provide softness to the fabric and make the cotton more accessible to the subsequent enzymatic finishing steps. A variant polypeptide as disclosed herein can be used in methods of finishing denim garments (e.g., a "bio-stoning process"), enzymatic desizing and providing softness to fabrics, and/or finishing process.

EXAMPLES

Example 1

Cloning of PS4 and G4-Amylases

*Pseudomonas sacharophila* is grown overnight on LB media and chromosomal DNA is isolated by standard methods (Sambrook J, 1989). A 2190 bp fragment containing the PS4 open reading frame (Zhou et al., 1989) is amplified from *P. sacharophila* chromosomal DNA by PCR using the primers P1 and P2 (see Table 3). The resulting fragment is used as a template in a nested PCR with primers P3 and P4, amplifying the openreading frame of PS4 without its signal sequence and introducing a NcoI site at the 5' end of the gene and a BamHI site at the 3' end. Together with the NcoI site a codon for a N-terminal Methionine is introduced, allowing for intracellular expression of PS4. The 1605 bp fragment is cloned into pCRBLUNT TOPO (Invitrogen) and the integrity of the construct analysed by sequencing. The *E. coli Bacillus* shuttle vector pDP66K (Penninga et al., 1996) is modified to allow for expression of the PS4 under control of the P32 promoter and the ctgase signal sequence. The resulting plasmid, pCSmta is transformed into *B. subtilis*.

A second expression construct is made in which the starch binding domain of PS4 is removed. In a PCR with primers P3 and P6 (Table 3) on pCSmta, a truncated version of the mta gene is generated. The full length mta gene in pCSmta is exchanged with the truncated version which resulted in the plasmid pCSmta-SBD.

G4 amylases of *Pseudomonas* sp. AM1 (2006), *Pseudomonas* sp. 7193, *Pseudomonas mendocina* (strain ymp) and *Hahella chejuensis* (strain KCTC 2396) were cloned into a *Bacillus* expression vector with signal sequence by gene synthesis (GeneScript; NJ, USA) of the sequences encoding the mature proteins with an M added at the N-terminus as shown in SEQ ID NO 3, 5, 7 and 9.

Example 2

Site-Directed Mutagenesis

Site-directed mutagenesis was used to produce variant polypeptide as disclosed herein. Mutations were introduced into a nucleic acid encoding pMS 382 having SEQ ID: 1, using the Quick Change™ method (Stratagene, California), according to instructions supplied with the kit with some modifications. Briefly, a single colony was picked and inoculated in 3 ml LB (22 g/l Lennox L Broth Base, Sigma) supplemented with 50 μg/ml kanamycin (Sigma) in a 10 ml Falcon tube. After overnight incubation at 37° C. at 200 rpm, the culture was spun down at 5000 rpm for 5 min. The medium was removed and the double-stranded DNA template was prepared using QIAGEN columns (QIAGEN). Primers were designed according to the manufacturers' protocol. For example, TABLE 1 lists primers that were used to generate new variants based on the nucleotide sequence of pMS382 as shown in SEQ ID NO: 52.

Next, PCR was performed to synthesize the mutant strand. The PCR reaction mix contained the following:
 2.5 μl 10 X QuickChange Multi reaction buffer
 0.75 μl QuickSolution
 X μl primers (10 pmol for primers of 28-35 nt; 7 pmol for primers of 24-27 nt; or 5 pmol for primers of 20-23 nt)
 1 μl dNTP mix
 X μl ds-DNA template (200 ng)
 1 μl QuickChange Multi enzyme blend (2.5 U/μl) (Pfu-Turbo DNA polymerase)
 X μl dH2O (to a final volume of 25 μl)

The PCR reaction was performed in an Eppendorf thermal cycler for 35 cycles of denaturation (96° C. for 1 min), primer annealing (62.8° C. for 1 min), and elongation (65° C. for 15 min), and then hold at 4° C. For each amplification reaction, 2 μl of DpnI restriction enzyme (10 U/μl) was added, and the mixture was incubated at 37° C. for ~3 hr.

The DpnI-treated DNA was then used to transform XL10-Gold® Ultracompetent cells (Stratagene). XL10-Gold® cells were thawed on ice. For each mutagenesis reaction, 45 μl cells were added to a pre-chilled Falcon tube. Subsequently, 2 μl of beta-mercaptoethanol mix was added to each tube. The mixture was incubated on ice for 10 min with swirling every 2 min. Then, 1.5 μl DpnI-treated DNA was added to each aliquot of cells, and the mixture was incubated on ice for 30 min. The sample was subject to a heat-pulse of 30 sec at 42° C., and was placed on ice for another 2 min. 0.5 ml of preheated NZY+ broth was added to each sample, and incubation was carried at 37° C. for 1 hr with shaking at 225-250 rpm. 200 μl of each transformation reaction were plated on LB plates (33.6 g/l Lennox L Agar, Sigma) supplemented with 1% starch and 50 μg/ml kanamycin. The plates were incubated overnight at 37° C. Individual colonies harboring the desired mutations were identified by DNA sequencing and subjected to plasmid preps to harvest plasmids with the desired mutations.

Example 3

Transformation into *Bacillus subtilis*

*Bacillus subtilis* (strain DB104A; Smith et al., *Gene* 70, 351-361 (1988)) is transformed with the mutated plasmid DNA according to the following protocol.

A. Media for Protoplasting and Transformation

| | |
|---|---|
| 2 x SMM | per litre: 342 g sucrose (1M); 4.72 g sodium maleate (0.04M); 8.12 g MgCl$_2$O•6H$_2$O (0.04M); pH 6.5 with concentrated NaOH. Distribute in 50-ml portions and autoclave for 10 min. |
| 4 x YT (½NaCl) | 2 g Yeast extract + 3.2 g Tryptone + 0.5 g NaCl per 100 ml. |
| SMMP | mix equal volumes of 2 x SMM and 4 x YT. |
| PEG | 10 g polyethyleneglycol 6000 (BDH) or 8000 (Sigma) in 25 ml 1 x SMM (autoclave for 10 min.). |

B. Media for Plating/Regeneration

| | |
|---|---|
| agar | 4% Difco minimal agar. Autoclave for 15 min. |
| sodium succinate | 270 g/l (1M), pH 7.3 with HCl. Autoclave for 15 min. |
| phosphate buffer | 3.5 g K$_2$HPO$_4$ + 1.5 g KH$_2$PO$_4$ per 100 ml. Autoclave for 15 min. |
| MgCl$_2$ | 20.3 g MgCl2•O6H$_2$O per 100 ml (1M). |
| casamino acids | 5% (w/v) solution. Autoclave for 15 min. |
| yeast extract | 10 g per 100 ml, autoclave for 15 min. |
| glucose | 20% (w/v) solution. Autoclave for 10 min. |
| DM3 regeneration medium: mix at 60° C. (water bath; 500-ml bottle): | 250 ml sodium succinate<br>50 ml casamino acids<br>25 ml yeast extract<br>50 ml phosphate buffer<br>15 ml glucose<br>10 ml MgCl$_2$<br>100 ml molten agar |

Add appropriate antibiotics: chloramphenicol and tetracycline, 5 μg/ml; erythromycin, 1 μg/ml. Selection on kanamycin is problematic in DM3 medium: concentrations of 250 μg/ml may be required.

C. Preparation of Protoplasts

Use detergent-free plastic or glassware throughout.

Inoculate 10 ml of 2×YT medium in a 100-ml flask from a single colony. Grow an overnight culture at 25-30° C. in a shaker (200 rev/min).

Dilute the overnight culture 20 fold into 100 ml of fresh 2×YT medium (250-ml flask) and grow until OD$_{600}$=0.4-0.5 (approx. 2 h) at 37° C. in a shaker (200-250 rev/min).

Harvest the cells by centrifugation (9000 g, 20 min, 4° C.).

Remove the supernatant with pipette and resuspend the cells in 5 ml of SMMP+5 mg lysozyme, sterile filtered.

Incubate at 37° C. in a waterbath shaker (100 rpm).

After 30 min and thereafter at 15 min intervals, examine 25 μl samples by microscopy. Continue incubation until 99% of the cells are protoplasted (globular appearance). Harvest the protoplasts by centrifugation (4000 g, 20 min, RT) and pipet off the supernatant. Resuspend the pellet gently in 1-2 ml of SMMP.

The protoplasts are now ready for use. Portions (e.g. 0.15 ml) can be frozen at −80° C. for future use (glycerol addition is not required). Although this may result in some reduction of transformability, 106 transformants per ug of DNA can be obtained with frozen protoplasts).

D. Transformation

Transfer 450 μl of PEG to a microtube.

Mix 1-10 μl of DNA (0.2 μg) with 150 μl of protoplasts and add the mixture to the microtube with PEG. Mix immediately, but gently.

Leave for 2 min at room temperature, and then add 1.5 ml of SMMP and mix.

Harvest protoplasts by microfuging (10 min, 13,000 rpm (10,000-12,000 g)) and pour off the supernatant. Remove the remaining droplets with a tissue.

Add 300 μl of SMMP (do not vortex) and incubate for 60-90 min at 37° C. in a waterbath shaker (100 rpm) to allow for expression of antibiotic resistance markers. (The protoplasts become sufficiently resuspended through the shaking action of the waterbath.) Make appropriate dilutions in 1×SSM and plate 0.1 ml on DM3 plates.

Example 4

Fermentation of Variants in Shake Flasks

The shake flask substrate is prepared by dissolving the following in water:

| | |
|---|---|
| Yeast extract | 2% (w/v) |
| Soy Flour | 2% (w/v) |
| NaCl | 0.5% (w/v) |
| Dipotassium phosphate | 0.5% (w/v) |
| Antifoam agent | 0.05% (w/v). |

The substrate is adjusted to pH 6.8 with 4 N sulfuric acid or sodium hydroxide before autoclaving. 100 ml of substrate is placed in a 500 ml flask with one baffle and autoclaved for 30 minutes. Subsequently, 6 ml of sterile dextrose syrup is added. The dextrose syrup is prepared by mixing one volume of 50% w/v dextrose with one volume of water followed by autoclaving for 20 minutes.

The shake flasks are inoculated with the variants and incubated for 24 hours at 35° C. and 180 rpm in an incubator. After incubation cells are separated from broth by centrifugation (10.000 g in 10 minutes) and finally, the supernatant is made cell free by microfiltration at 0.2 μm. The cell free supernatant is used for assays and application tests.

TABLE 1

Primers used to generate variants based on the nucleotide sequence of pMS382 as shown in SEQ ID NO: 52.

| Mutation | 5' Oligo Sequence 3' | modification | Strand | Purpose |
|---|---|---|---|---|
| Q42K | GTATAACATCCTGAGACAAaaaGCGAGCAC AATTGCCG | 5' phosphate | + | MSDM |
| Q42N | GTATAACATCCTGAGACAAaacGCGAGCAC AATTGCC | 5' phosphate | + | MSDM |
| R88L | GCATGACTTTAACAAAAACGGCctgTATGG AAGCGATGCTC | 5' phosphate | + | MSDM |
| R88Y | GGCATGACTTTAACAAAAACGGCtatTATG GAAGCGATGCTCAAC | 5' phosphate | + | MSDM |

TABLE 1-continued

Primers used to generate variants based on the nucleotide sequence of pMS382 as shown in SEQ ID NO: 52.

| Mutation | 5' Oligo Sequence 3' | modification | Strand | Purpose |
|---|---|---|---|---|
| L88K | GGCATGACTTTAACAAAAACGGCaaaTATGGAAGCGATGCTCAAC | 5' phosphate | + | MSDM |
| S205L | GCCCCGGAAAGAGTTGATctgTGGATGAGCGATTCAGCG | 5' phosphate | + | MSDM |
| T235R | GTGGGATTGGAGAAATagaGCGAGCTGGCAGC | 5' phosphate | + | MSDM |
| T235K | GTGGGATTGGAGAAATaaaGCGAGCTGGCAGC | 5' phosphate | + | MSDM |
| T235H | GCCGTGGGATTGGAGAAATcatGCGAGCTGGCAGCAG | 5' phosphate | + | MSDM |
| T235Q | CCGTGGGATTGGAGAAATcagGCGAGCTGGCAGCAG | 5' phosphate | + | MSDM |
| Q240E | CGCTCCAATCTTTGATGATTTCCTGCCAGCTCGCTG | 5' phosphate | – | MSDM |
| Q240D | CAGCGAGCTGGCAGgatATCATCAAAGATTGGAGCG | 5' phosphate | + | MSDM |
| Q311P | CAACATAAATGGCCGCTTccgGATGGCCTTATCAGACAG | 5' phosphate | + | MSDM |
| A392D | GCCCTGAATAGCGATCTGgatAATCCGGGACAAGTTGC | 5' phosphate | + | MSDM |
| A392Y | CGCCCTGAATAGCGATCTGtatAATCCGGGACAAGTTGCTAG | 5' phosphate | + | MSDM |
| S409E | GCGAAGCAGTCAATGCCgaaAATGGCCAAGTCAGAGTCTG | 5' phosphate | + | MSDM |
| R248H | CATCAAAGATTGGAGCGATcatGCAAAATGCCCGGTCTTTGAC | 5' phosphate | + | MSDM |
| S266T | CGCATGCAAAATGGAacgGTCGCCGATTGGAAACATG | 5' phosphate | + | MSDM |
| S377D | CTACAGTTgatGGCAGCCAACAAAC | 5' phosphate | + | MSDM |

Example 5

Amylase Assays

Betamyl Assay

One Betamyl unit is defined as activity degrading 0.0351 mmole per 1 min. of PNP-coupled maltopentaose so that 0.0351 mmole PNP per 1 min. can be released by excess alpha-glucosidase in the assay mix. The assay mix contains 50 ul 50 mM Na-citrate, 5 mM CaCl2, pH 6.5 with 25 ul enzyme sample and 25 ul Betamyl substrate (Glc5-PNP and alpha-glucosidase) from Megazyme, Ireland (1 vial dissolved in 10 ml water). The assay mix is incubated for 30 min. at 40° C. and then stopped by adding 150 ul 4% Tris. Absorbance at 420 nm is measured using an ELISA-reader and the Betamyl activity is calculate based on Activity=A420*d in Betamyl units/ml of enzyme sample assayed. For dosing in baking trials 1 BMK=1000 Betamyl units are used.

Endo-Amylase Assay

The endo-amylase assay is identical to the Phadebas assay run according to manufacturer (Pharmacia & Upjohn Diagnostics AB).

Exo-Specificity

The ratio of exo-amylase activity to Phadebas activity was used to evaluate exo-specificity.

Example 6

Procedure Heat Stability Determinations Based on Residual Activity

The enzyme samples in appropriate dilutions are incubated in 50 mM Na-acetate buffer, pH 5.0 with 0.5 M NaCl at room temperature (control) or for 4 minutes at 80° C. (heated sample), and immediately after that the control and heated sample are analysed using the Betamyl assay. The residual activity is calculated as the Betamyl activity of the heated sample divided by the Betamyl activity of the control sample.

Example 7

Stabilising Effects of Mutations

Using the procedure described in Example 6 the stabilising effects of the mutations Q42K, R88L, S205L, E223S, Q311P, S409E and T235K are shown in Table 2 as an increase in residual activity after heating. Likewise the stabilising effect of A392D is shown in Table 3, of S205L, S223A and S205L combined with S409 in Table 4, of N34Q and G100Q in Table 5 and of Q240E in Table 6. In tables 2-6, the variants have the same sequence as the one mentioned in the first line except for the further mutation(s) made as described in the second column.

TABLE 2

Stabilising effect of Q42K, R88L, S205L, E223S, Q311P, S409E and T235K combined with Q311P

| Variant | Further mutation in pMS382 | Residual activity (%) |
| --- | --- | --- |
| pMS382 (SEQ ID NO: 1) | | 8.4 |
| pMS465 (SEQ ID NO: 18) | E223S | 9.6 |
| pMS1042 (SEQ ID NO: 19) | Q311P | 13.1 |
| pMS1104 (SEQ ID NO: 20) | Q42K | 11.2 |
| pMS1153 (SEQ ID NO: 21) | R88L | 19.5 |
| pMS1286 (SEQ ID NO: 22) | T235R | 12.3 |
| pMS1284 (SEQ ID NO: 23) | T235R, Q311P | 17.2 |
| pMS1290 (SEQ ID NO: 24) | T235K | 14.1 |
| pMS1484 (SEQ ID NO: 25) | S205L | 8.8 |
| pMS1579 (SEQ ID NO: 26) | S409E | 16.4 |

TABLE 3

Stabilising effect of A392D

| Variant | Further mutation in pMS1105 | Residual activity (%) |
| --- | --- | --- |
| pMS1105 (SEQ ID NO: 27) | | 11.0 |
| pMS1723 (SEQ ID NO: 28) | A392D | 12.3 |

TABLE 4

Stabilising effect of S205L, S223A and S205L combined with S409E

| Variant | Further mutation in pMS1776 | Residual activity (%) |
| --- | --- | --- |
| pMS1776 (SEQ ID NO: 12) | | 18.9 |
| pMS2104 (SEQ ID NO: 29) | S223A | 22.1 |
| pMS2138 (SEQ ID NO: 30) | S205L | 22.4 |
| pMS2022 (SEQ ID NO: 15) | S205L, S409E | 23.3 |

TABLE 5

Stabilising effect of N34Q and G100Q

| Variant | Further mutation in pMS2124 | Residual activity (%) |
| --- | --- | --- |
| pMS2124 (SEQ ID NO: 31) | | 24.7 |
| pMS2177 (SEQ ID NO: 32) | N34Q | 28.8 |
| pMS2178 (SEQ ID NO: 33) | G100Q | 26.4 |

TABLE 6

Stabilising effect of Q240E

| Variant | Further mutation in pMS2022 | Residual activity (%) |
| --- | --- | --- |
| pMS2022 (SEQ ID NO: 15) | | 23.3 |
| pMS2118 (SEQ ID NO: 34) | Q240E | 26.8 |

Example 10

Recipe for Baking Trials

Baking trials were carried out with a standard white bread sponge and dough recipe for US toast. The sponge dough is prepared from 1500 g of flour "Gold Medal" from General Mills, USA, 890 g of water, 40 g of soy bean oil, 7.5 g GRINDSTED™ SSL P55 Veg, 10 g emulsifier DIMODAN™ PH300, 26 g dry yeast and ascorbic acid (20 ppm final concentration). The sponge is mixed for 1 min. at low speed and subsequently 3 min. at speed 2 on a Hobart spiral mixer. The sponge is subsequently fermented for 3 hours at 25° C., 85% RH.

Thereafter, 500 g of "Gold Medal" flour, 14 g dry yeast, 5 g of calcium propionate, 240 g High Fructose Corn Syrup (42%), 5 g of calcium propionate, 250 g of water and ascorbic acid (30 ppm final concentration) and 40 g of salt are added to the sponge. The resulting dough is mixed for 0.5 min. at low speed and then 10.5 min. on high speed on a Hobart spiral mixer.

The dough is rested for 5 min. at ambient temperature, and then 794 g dough pieces are scaled, moulded on a cross grain moulder and transferred to pans. After 60 min. proofing at 43° C. at 80% RH the doughs are baked for 21 min. at 200° C. in a Reed Rack Oven.

Example 11

Protocol for Evaluation of Firmness, Resilience and Cohesiveness

Texture Profile Analysis of Bread

Firmness, resilience and cohesiveness are determined by analysing bread slices by Texture Profile Analysis using a Texture Analyser from Stable Micro Systems, UK. Calculation of firmness, resilience, and cohesiveness is done according to preset standard supplied by Stable Micro System, UK. The probe used is aluminium 50 mm round.

Firmness is determined at 40% compression during the first compression. The figure is the force needed to compress the slice to 40% of the total thickness. The lower the value, the softer the bread. The firmness is expressed for example in grams.

Example 12

Evaluation of Antistaling Effects of G4 Amylase Variant Polypeptides

Bread was baked as described in Example 10 with pMS1776, pMS1934, pMS2020, pMS2022 and pMS2062 in dosages varying from 7.5 to 20 BMK/kg corresponding to 7,500 to 20,000 Betamyl units/kg.

The firmness of the bread is tested according to the protocol set out in Example 11 at various times after baking. As controls, bread baked with standard dosages of 600 ppm Novamyl 1500 and/or 416.66 ppm of a composition comprising SEQ ID NO: 1 was also baked.

Figure 2:
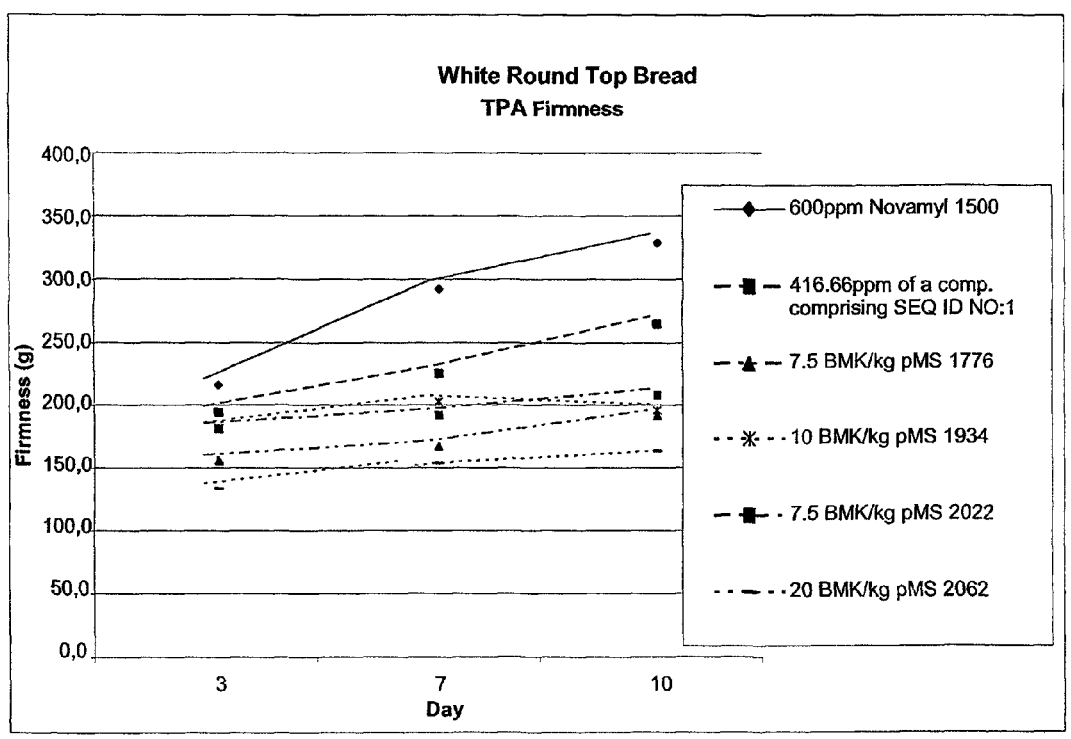
FIG. 2 shows firmness development of bread baked with pMS1776 (SEQ ID NO: 12), pMS1934 (SEQ ID NO: 13), pMS2022 (SEQ ID NO: 15) and pMS2062 (SEQ ID NO: 16) compared to bread baked with a composition comprising SEQ ID NO: 1 and Novamyl 1500.

FIGS. 1 and 2 show the firmness results. Relative to the controls with standard dosages 600 ppm Novamyl 1500 and/or 416.66 ppm of a composition comprising SEQ ID NO: 1 a much stronger reduction in the firming rate from day 3 to day 10 after baking is obtained with pMS1776, pMS1934, pMS2020, pMS2022 and pMS2062. Also these breads were strongly improved in resilience and cohesiveness relative to the controls.

This indicates that the variant polypeptide(s) as described herein have highly improved antistaling effects compared to Novamyl 1500 and a composition comprising SEQ ID NO: 1.

Example 13

Protocol for Evaluation of Crumbliness (Resistance to Crumbling)

Two slices of bread are placed on a piece of paper. Each slice is divided into 4 squares by vertical and subsequent horizontal tears of the slice.

Tearing is done by pulling the crumb apart by the fingers. First the slice is torn from the middle of the top bread surface to the middle of the bottom bread surface. Thereafter, each half of the original slice is torn from the crust side to the inside of the slice. The small crumb pieces, which are separated from the 4 squares, are removed by shaking each piece after a tear at least 3 times by moving the hand up and down.

The weight of the separated small crumb pieces is determined as a measure of crumbliness. This assay may be referred to as the "Crumbliness Evaluation Protocol".

Example 14

Protocol for Evaluation of Foldability

The toast bread is sliced using an automatic bread slicer with set slice thickness of 15 mm. The slice is folded by hand from the top of the slice towards the bottom, so that the direction of the crease is from side to side.

The foldability is visually assessed using the following scoring system:

| Score | Feature |
| --- | --- |
| 1 | Unfoldable, slice breaks upon folding |
| 2 | Foldable, whole slice breaks within 5 seconds after folding |
| 3 | Foldable, part of the slice breaks within 5 seconds after folding. Other parts break later. |
| 4 | Foldable, part of the slice breaks later than 5 seconds after folding. Other parts do not break. |
| 5 | Foldable, no part of the slice break after folding |

This assay may be referred to as the "Foldability Evaluation Protocol".

Example 15

Preparation of DP4 Syrup

Materials:

SPEZYME FRED® bacterial alpha amylase (Danisco US Inc., Genencor Division) treated granular corn starch liquefact (34% ds, 9.1DE).

Pullulanase (OPTIMAX L-1000, Danisco US Inc., Genencor Division)

Experimental:

Starch liquefact was pH adjusted to 5.2 with NaOH and then each of 100 g liquefact was incubated at 60 C for DP4 saccharification by dosing enzymes at 0.03 BMK/gds. Pullulanase when used was dosed at 0.5 ASPU/gds. Reaction was carried out up to 40 hours, stopped for periodical sampling to check peak DP4. When peak DP4 was observed, the reaction was stopped by heating in boiling water.

Results:

TABLE 1

| | | Sugar production (%) | | | | | | | | | | |
| --- | --- | --- | --- | --- | --- | --- | --- | --- | --- | --- | --- | --- |
| Enzymes | Hr | % DP1 | % DP2 | % DP3 | % DP4 | % DP5 | % DP6 | % DP7 | % DP8 | % DP9 | % DP10 | % DP11+ |
| pMS2062 | 16 | 2.31 | 5.50 | 8.67 | 38.00 | 0.81 | 0.17 | 0.67 | 0.99 | 3.23 | 0.39 | 39.30 |
| pMS2062 + PU | | 2.42 | 5.70 | 8.99 | 38.12 | 1.06 | 0.19 | 0.85 | 1.29 | 4.10 | 1.06 | 36.20 |
| pMS2062 | 19.5 | 2.49 | 5.73 | 9.03 | 39.86 | 0.63 | 0.00 | 0.51 | 0.83 | 2.62 | 0.38 | 37.90 |
| pMS2062 + PU | | 2.60 | 5.89 | 9.45 | 40.37 | 0.88 | 0.00 | 0.70 | 1.18 | 3.65 | 1.19 | 34.10 |
| pMS2062 | 22 | 2.59 | 5.69 | 9.20 | 41.16 | 0.56 | 0.00 | 0.45 | 0.75 | 2.27 | 0.37 | 37.00 |
| pMS2062 + PU | | 2.81 | 5.95 | 9.91 | 41.96 | 0.78 | 0.00 | 0.58 | 1.02 | 3.30 | 1.26 | 32.40 |
| pMS2062 | 40 | 3.41 | 6.32 | 10.47 | 43.76 | 0.24 | 0.12 | 0.16 | 0.87 | 0.30 | 0.20 | 34.10 |
| pMS2062 + PU | | 3.67 | 7.01 | 11.42 | 45.80 | 0.43 | 0.26 | 0.42 | 2.22 | 1.87 | 0.17 | 26.70 |

As shown in Table 1, the results indicated that PMS2062 produced DP4 as a major sugar product. As also indicated, pullulanase (PU) addition (PMS2062+PU) resulted in faster reduction in higher sugars (see e.g., DP11+), while DP4 level was minimally affected.

SEQUENCES

SEQ ID NO: 1.

Mature protein sequence of pMS382

```
DQAGKSPAGVRYHGGDEIILQGFHWNVVREAPYNWYNILRQQASTIAAD
GFSAIWMPVPWRDFSSWTDGDKSGGGEGYFWHDFNKNGRYGSDAQLRQA
AGALGGAGVKVLYDVVPNHMNRFYPDKEINLPAGQRFWRNDCPDPGNGP
NDCDDGDRFLGGEADLNTGHPQIYGMFRDEFTNLRSGYGAGGFRFDFVR
GYAPERVDSWMSDSADSSFCVGELWKEPSEYPPWDWRNTASWQQIIKDW
SDRAKCPVFDFALKERMQNGSVADWKHGLNGNPDPRWREVAVTFVDNHD
TGYSPGQNGGQHKWPLQDGLIRQAYAYILTSPGTPVVYWPHMYDWGYGD
FIRQLIQVRRTAGVRADSAISFHSGYSGLVATVSGSQQTLVVALNSDLA
NPGQVASGSFSEAVNASNGQVRVWRSGSGDGGGNDGG
```

SEQ ID NO: 2.

Mature protein of G4 amylase of *Pseudomonas* sp. AM1 (2006) with M added at the N-terminus (Q1EJP2 protein):

```
  1 MDLAGKSPGG VRYHGGDEII LQGFHWNVIR ESPNNWYNTL
    RDMAPTIAAD

51 GFSAIWMPVP WRDFSSWSDG ANSGGGEGYF WHDFNKNGRY
    GSDTQLKQAA

101 GALNNAQVKV LYDVVPNHMN RGYPDKQINL PAGQGFWRND
    CADPGNYPND

151 CDDGDRFMGG DADLNTANPQ VYGMFRDEFA NLRSNYGAGG
    FRFDFVRGYA

201 GERVDSWMGA AHDNAFCVGE LWKAPAEYPS WDWRNTASWQ
    QVIKDWSDRA

251 KCPVFDFALK ERMQNGSIAD WKNGLNGNPD PRWREVAVTF
    VDNHDAGYSP

301 GQNGGQHHWA LQDGLIRQAY AYILTSPGTP VVYWSHMYDW
    GYGDFIRQLI

351 QVRRTAGVRA DSAISFHSGY SGLVATVSGS QQTLVVALNS
    DLANPGQVAS

401 GSFSEAVNAS NGQVRVWRSG SGDGGGNDGG EGGLVNVNFR
    CDNGVTQMGD

451 SVYAVGNVSQ LGNWSPASAV RLTDTSSYPT WKGSIALPDG
    QNVEWKCLIR

501 NEADATLVRQ WQSGGNNQVQ AAAGASTSGS F*
```

SEQ ID NO: 3.

DNA sequence of nucleotide encoding G4 amylase of *Pseudomonas* sp. AM1 (2006) (Q1EJP2) with M added at the N-terminus (Q1EJP2 DNA):

```
atggatctggcaggcaaatcaccgggcggcgttagatatcatggcggcg
atgaaattattctgcaaggctttcattggaatgttattagagaatcacc
gaataattggtataatacactgagagatatggcaccgacaattgcagca
gatggcttttcagcaatttggatgccggttccgtggagagattttcat
catggtcagatggcgcaaattcaggcggcggcgaaggctattttggca
tgatttaataaaaatggcagatatggctcagatacacaactgaaacaa
gcagcaggcgcactgaataatgcacaagttaaagttctgtatgatgttg
ttccgaatcatatgaatagaggctatccggataaacaaattaatctgcc
ggcaggccaaggcttttggagaaatgattgcgcagatccgggcaattat
ccgaatgattgcgatgatggcgatagatttatgggcggcgatgctgatc
tgaatacagcaaatccgcaagtttatggcatgtttagagatgaatttgc
aaatctgagatcaaattatggcgcaggcggctttagatttgattttgtt
agaggctatgcaggcgaaagagttgattcatggatgggcgcagcacatg
ataatgcattttgcgttggcgaactgtggaaagcaccggcagaatatcc
gtcatgggattggagaaatacagcatcatggcaacaagttattaaagat
tggtcagatagagcaaaatgcccggttttgattttgcactgaaagaaa
gaatgcaaaatggctcaattgcagattggaaaaatggcctgaatggcaa
tccggatccgagatggagagaagttgcagttacatttgttgataatcat
gatgcaggctattcaccgggccaaaatggcggccaacatcattgggcac
tgcaagatggcctgattagacaagcatatgcatatattctgacatcacc
gggcacaccggttgtttattggtcacatatgtatgattggggctatggc
gattttattagacaactgattcaagttagaagaacagcaggcgttagag
cagattcagcaatttcatttcattcaggctattcaggcctggttgcaac
agtttcaggctcacaacaaacactggttgttgcactgaatagcgatctg
gcaaatccgggccaagttgcatcaggctcattttcagaagcagttaatg
catcaaatggccaagttagagtttggagatcaggctcaggcgatggcgg
cggcaatgatggcggcgaaggcggcctggttaatgttaattttagatgc
gataatggcgttacacaaatgggcgattcagtttatgcagttggcaatg
tttcacaactgggcaattggtcaccggcatcagcagttagactgacaga
tacatcatcatatccgacatggaaaggctcaattgcactgccggatggc
caaaatgttgaatggaaatgcctgattagaaatgaagcagatgcaacac
tggttagacaatggcaatcaggcggcaataatcaagttcaagcagcagc
aggcgcatcaacatcaggctcatttaa
```

SEQ ID NO: 4.

Mature protein of G4 amylase of *Pseudomonas* sp. 7193 with M added at the N-terminus (A5CVD5 protein):

```
  1 MDLAGKSPGG VRYHGGDEII LQGFHWNVIR ESPNNWYNTL
    RDMAPTIAAD

51 GFSAIWMPVP WRDFSSWSDG ANSGGGEGYF WHDFNKNGRY
    GSDTQLKQAA

101 GALNNAQVKV LYDAVPNHMN RGYPDKQINL PAGQGFWRND
    CADPGNYPND

151 CDDGDRFMGG DADLNTANPQ VYGMFRDEFA NLRSNYGAGG
    FRFDFVRGYA

201 GERVDSWMGD GACQRLLRGR ALEGTGRIPE LGLAQYGQLA
    AVIKDWSDRA

251 KVPGCSNFAL KGAHAERLPS PTGRTASTAT PMPRWREVAV
    TFVDNHDTGY

301 SPGQNGGQHH WALRDDLVRQ AYAYILASPG TPVVYWSHMY
    DWGHGPLIRQ

351 LIQIRRAAGV RADSAIEFHS GYSGLVATVR GTAQTLVMAL
    GSNLSSPAEV

401 SSGSFSQALN QDSGQLRIWT TGSTGGDEGD GGGDGTMVSV
    NFRCDNGITQ

451 PGDSVYAVGS LAQLGSWSPA NAVRLTDVSN YPTWKGAISL
    PAGQAVEWKC

501 IVRSEADPTQ VRQWQAGDNN RVTAGAGATT IGRL*
```

SEQ ID NO: 5.

DNA sequence of nucleotide encoding [G4 amylase of *Pseudomonas* sp. 7193 (A5CVD5) with M added at the N-terminus (A5CVD5 DNA):

```
atggatctggcaggcaaatcaccgggcggcgttagatatcatggcggcg
atgaaattattctgcaaggctttcattggaatgttattagagaatcacc
gaataattggtataatacactgagagatatggcaccgacaattgcagca
gatggcttttcagcaatttggatgccggttccgtggagagattttcat
catggtcagatggcgcaaattcaggcggcggcgaaggctattttggca
```

```
tgattttaataaaaatggcagatatggctcagatacacaactgaaacaa gcagcaggcgcactgaataatgcacaagttaaagttctgtatgatgcag ttccgaatcatatgaatagaggctatccggataaacaaattaatctgcc ggcaggccaaggcttttggagaaatgattgcgcagatccgggcaattat ccgaatgattgcgatgatggcgatagatttatgggcggcgatgctgatc tgaatacagcaaatccgcaagtttatggcatgtttagagatgaatttgc aaatctgagatcaaattatggcgcaggcggctttagatttgattttgtt agaggctatgcaggcgaaagagttgattcatggatgggcgatggcgcat gccaaagactgctgagaggcagagcactggaaggcacaggcagaattcc ggaactgggcctggcacaatatggccaactggcagcagttattaaagat tggtcagatagagcaaaagttccgggctgctcaaattttgcactgaaag gcgcacatgcagaaagactgccgtcaccgacaggcagaacagcatcaac agcaacaccgatgccgagatggagagaagttgcagttacatttgttgat aatcatgatacaggctattcaccgggccaaaatggcggccaacatcatt gggcactgagagatgatctggttagacaagcatatgcatatattctggc atcaccgggcacaccggttgtttattggtcacatatgtatgattggggt catggaccgctgattagacaactgattcaaattagaagagcagcaggcg ttagagcagattcagcaattgaatttcattcaggctattcaggcctggt tgcaacagttagaggcacagcacaaacactggttatggcactgggctca aatctgtcatcaccggcagaagtttcatcaggctcattttcacaagcac tgaatcaagattcaggccaactgagaatttggacaacaggctcaacagg cggcgatgaaggcgatggcggcggcgatggcacaatggtttcagttaat tttagatgcgataatgcattacacaaccgggcgattcagtttatgcag ttggctcactggcacaactgggctcatggtcaccggcaaatgcagttag actgacagatgtttcaaattatccgacatggaaaggcgcaatttcactg ccggcaggccaagcagttgaatggaaatgcattgttagatcagaagcag atccgacacaagttagacaatggcaagcaggcgataataatagagttac agcaggcgcaggcgcaacaacaattggcagactgtaa
```

SEQ ID NO: 6.

Mature protein of G4 amylase of *Pseudomonas mendocina* (strain ymp) with M added at the N-terminus (A4XX23 protein):

```
  1 MDAPGKTASG VRYHGGDEII LQGFHWNTVR TSSNWYATLA
    SMAPTLAADG

51 FSAIWMPVPW RDFSSWSDPG NGTSGGGEGY FWHDFNKNGR
    YGSDSLLRQA

101 ASALNAAGVK PIYDVVPNHM NRGYPDKEIN LPAGQGLWRH
    DCNDPGNYAN

151 DCDDGDRFMG GDADLNTGHP QNYAMFRDEF ARLRSQYGAG
    GFRFDFVRGY

201 AGERVASWMS DAHDNGFCLG ELWKAPGEYP SWDWRNGASW
    QQILKDWSDR

251 AKCTVFDFAL KERMQNGGIA DWRHGLNGNP DARWREVAVT
    FVDNHDTGYS

301 PGPHGGQHHW PLPDARLKQA YAYILSSPGT PVVYWPHMYD
    WGHGDFIRQL

351 IQIRRAAGVK AASAIQFHTG FSGLVATISG SQQQLLIALD
    SNLSSPGQVA

401 SGDFTQALNT DNGAIRIWRS GQGGGDGQGN LVSVNFRCDN
    GVTQWGDSVY

451 ALGNVTQLGN WSPAGAVRLT DTSAYPTWKG SIALPAGQQV
    QWKCIVRSES

501 NPTQVKTWQP GGNNSVTVAS GASTAGSF*
```

SEQ ID NO: 7.

DNA sequence of nucleotide encoding G4 amylase of *Pseudomonas mendocina* (strain ymp) (A4XX23) with M added at the N-terminus: (A4XX23 DNA):

```
atggatgcaccgggcaaaacagcatcaggcgttagatatcatggcggcg atgaaattattctgcaaggctttcattggaatacagttagaacatcatc aaattggtatgcaacactggcatcaatggcaccgacactggcagcagat ggcttttcagcaatttggatgccggttccgtggagagattttttcatcat ggtcagatccgggcaatggcacatcaggcggcggcgaaggctattttg gcatgattttaataaaaatggcagatatggctcagattcactgctgaga caagcagcatcagcactgaatgcagcaggcgttaaaccgatttatgatg ttgttccgaatcatatgaatagaggctatccggataaagaaattaatct gccggcaggccaaggcctgtggagacatgattgcaatgatccgggcaat tatgcaaatgattgcgatgatggcgatagatttatgggcggcgatgctg atctgaatacaggccatccgcaaaattatgcaatgtttagagatgaatt tgcaagactgagatcacaatatgcgcaggcggctttagatttgattttg ttagaggctatgcaggcgaaagagttgcatcatggatgtcagatgcac atgataatggcttttgcctgggcgaactgtggaaagcaccgggcgaata tccgtcatgggattggagaaatggcgcatcatggcaacaaattctgaaa gattggtcagatagagcaaaatgcacagttttttgattttgcactgaaag aaagaatgcaaaatggcggcattgcagattggagacatggcctgaatgg caatccggatgcaagatggagagaagttgcagttacatttgttgataat catgatacaggctattcaccgggcccgcatggcggccaacatcattggc cgctgccggatgcaagactgaaacaagcatatgcatatattctgtcatc accgggcacaccggttgtttattggccgcatatgtatgattggggtcat ggagattttattagacaactgattcaaattagaagagcagcaggcgtta aagcagcatcagcaattcaatttcatacaggcttttcaggcctggttgc aacaatttcaggctcacaacaacaactgctgattgcactggattcaaat ctgtcatcaccgggccaagttgcatcaggcgattttacacaagcactga atacagataatggcgcaattagaatttggagatcaggccaaggcggcgg cgatggccaaggcaatctggtttcagttaattttagatgcgataatggc gttacacaatggggcgattcagtttatgcactgggcaatgttacacaac tgggcaattggtcaccggcaggcgcagttagactgacagatacatcagc
```

-continued
```
atatccgacatggaaaggctcaattgcactgccggcaggccaacaagtt caatggaaatgcattgttagatcagaatcaaatccgacacaagttaaaa ccatggcaaccgggcggcaataattcagttacagttgcatcaggcgatc aacagcaggctcattttaa
```

SEQ ID NO: 8.

Mature protein of G4 amylase of *Hahella chejuensis* (strain KCTC 2396) with M added at the N-terminus (Q2SEA8 protein):

```
  1 MESSGKSGAG VRFHGGDEII LQGFHWNVVR TAERNWYNIL
    QSKAQQISED

51 GFTAIWMPVP WRDNSSWQAS SDTRFGGEGY FWADMDKNSR
    YGDDGQLKQA

101 ASALKNKGVK VIYDIVPNHH DRGHSNDSLN LPSGQGYYRS
    DCSSCDDGDP

151 FMDGGSDFST AHPDVYDLFK NELVNLKTNY SAGGFRFDFV
    RGYAPERISA

201 WMSASLDSGY CVGELWKGPS EYPSWDWRHS ASWQEILKDF
    TDASDCSVFD

251 FALKERMQNG SISDWRYGLN GNPSAQWREV AVTFVDNHDT
    GYSPGPLGGQ

301 HHWALPDWKR KMAYAYILSS PGTPVVYWPH MYDWGMRDFI
    RNLIQLRKSA

351 GVKAYSGVQF HDGFSGLVGT TSGSNGKLLF AIDSNFSSPN
    QVAGGAWNLA

401 VNEDNGRIRI WRQ*
```

SEQ ID NO: 9.

DNA sequence of nucleotide encoding of G4 amylase of *Hahella chejuensis* (strain KCTC 2396) with M added at the N-terminus (Q2SEA8 DNA):

```
atggaatcatcaggcaaatcaggcgcaggcgttagatttcatggcggcga tgaaattattctgcaaggctttcattggaacgttgttagaacagcagaaa gaaactggtacaacatcctgcaatcaaaagcacaacaaatttcagaagat ggctttacagcaatttggatgccggttccgtggagagataattcatcatg gcaagcatcatcagatacaagatttggcggcgaaggctattttttgggcag atatggataaaaattcaagatatggcgatgatggccaactgaaacaagca gcatcagcactgaaaaataaaggcgttaaagttatttatgatattgttcc gaatcatcatgatagaggccattcaaatgattcactgaatctgccgtcag gccaaggctattatagatcagattgctcatcatgcgatgatggcgatccg tttatggatggcggctcagattttttcaacagcacatccggatgtttacga tctgtttaaaaacgaactggttaacctgaaaacaaactactcagcaggcg gctttagatttgattttgttagaggctatgcaccggaaagaatttcagca tggatgtcagcatcactggattcaggctattgcgttggcgaactgtggaa aggcccgtcagaatatccgtcatgggattggagacattcagcatcatggc aagaaattctgaaagatttacagatgcatcagattgctcagttttttgat tttgcactgaaagaaagaatgcaaaatggctcaatttcagattggagata
```

```
tggcctgaatggcaatccgtcagcacaatggagagaagttgcagttacat ttgttgataatcatgatacaggctattcaccgggcccgctgggcggccaa catcattgggcactgccggattggaaaagaaaaatggcatatgcatatat tctgtcatcaccgggcacaccggttgtttattggccgcatatgtatgatt ggggcatgagagatttttattagaaatctgattcaactgagaaaatcagca ggcgttaaagcatattcaggcgttcaatttcatgatggcttttcaggcct ggttggcacaacatcaggctcaaatggcaaactgctgtttgcaattgatt caaattttcatcaccgaatcaagttgcaggcggcgcatggaatctggca gttaatgaagataatggcagaattagaatttggagacaataa
```

SEQ ID NO: 10.

>gi|77787|pir||S05667 glucan 1,4-alpha-maltotetraohydrolase (EC 3.2.1.60) mature protein without the signal sequence—*Pseudomonas saccharophila*

```
DQAGKSPAGVRYHGGDEIILQGFHWNVVREAPNDWYNILRQQASTIAADG

FSAIWMPVPWRDFSSWTDGGKSGGGEGYFWHDFNKNGRYGSDAQLRQAAG

ALGGAGVKVLYDVVPNHMNRGYPDKEINLPAGQGFWRNDCADPGNYPNDC

DDGDRFIGGESDLNTGHPQIYGMFRDELANLRSGYGAGGFRFDFVRGYAP

ERVDSWMSDSADSSFCVGELWKGPSEYPSWDWRNTASWQQIIKDWSDRAK

CPVFDFALKERMQNGSVADWKHGLNGNPDPRWREVAVTFVDNHDTGYSPG

QNGGQHHWALQDGLIRQAYAYILTSPGTPVVYWSHMYDWGYGDFIRQLIQ

VRRTAGVRADSAISFHSGYSGLVATVSGSQQTLVVALNSDLANPGQVASG

SFSEAVNASNGQVRVWRSGSGDGGGNDGGEGGLVNVNFRCDNGVTQMGDS

VYAVGNVSQLGNWSPASAVRLTDTSSYPTWKGSIALPDGQNVEWKCLIRN

EADATLVRQWQSGGNNQVQAAAGASTSGSF
```

SEQ ID NO: 11.

Signal peptide of glucan 1,4-alpha-maltotetrahydrolase (EC 3.2.1.60)—*Pseudomonas saccharophila*

```
MSHILRAAVLAAVLLPFPALA
```

SEQ ID NO: 12.

Mature protein sequence of pMS1776

```
  1 DQAGKSPAGV RYHGGDEIIL QGFHWNVVRE APYNWYNILR
    QKASTIAADG

51 FSAIWMPVPW RDFSSWTDGD KSGGGEGYFW HDFNKNGLYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDSWMSDS ADSSFCVGEL WKSPSEYPPW DWRNRASWQQ
    IIKDWSDRAK

251 CPVFDFALKE RMQNGSVADW KHGLNGNPDP RWREVAVTFV
    DNHDTGYSPG

301 QNGGQHKWPL PDGLIRQAYA YILTSPGTPV VYWPHMYDWG
    YGDFIRQLIQ
```

```
351 VRRTAGVRAD SAISFHSGYS GLVATVSGSQ QTLVVALNSD
    LDNPGQVASG

401 SFSEAVNASN GQVRVWRSGS GDGGGNDGG*
```

SEQ ID NO: 13.
Mature protein sequence of pMS1934

```
  1 DQAGKSPAGV RYHGGDEIIL QGFHWNVVRE APYNWYNILR
    QKASTIAADG

51 FSAIWMPVPW RDFSSWTDGD KSGGGEGYFW HDFNKNGLYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDSWMSDS ADSSFCVGEL WKSPSEYPPW DWRNRASWQQ
    IIKDWSDRAK

251 CPVFDFALKE RMQNGSVADW KHGLNGNPDP RWREVAVTFV
    DNHDTGYSPG

301 QNGGQHKWPL PDGLIRQAYA YILTSPGTPV VYWPHMYDWG
    YGDFIRQLIQ

351 VRRTAGVRAD SAISFHSGYS GLVATVSGSQ QTLVVALNSD
    LDNPGQVASG

401 SFSEAVNAEN GQVRVWRSGS GDGGGNDGG*
```

SEQ ID NO: 14
Mature protein sequence of pMS2020

```
  1 DQAGKSPAGV RYHGGDEIIL QGFHWNVVRE APYNWYNILR
    QKASTIAADG

51 FSAIWMPVPW RDFSSWTDGD KSGGGEGYFW HDFNKNGLYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDSWMSDS ADSSFCVGEL WKSPSEYPPW DWRNRASWQQ
    IIKDWSDRAK

251 CPVFDFALKE RMQNGSVADW KHGLNGNPDP RWREVAVTFV
    DNHDTGYSPG

301 QNGGQHKWPL PDGLIRQAYA YILTSPGTPV VYWPHMYDWG
    YGDFIRQLIQ

351 VRRTAGVRAD SAISFHSGYS GLVATVSGSQ QTLVVALNSD
    LDNPGQVASG

401 SFSEAVNAEN GQVRVWRSGS GDGGGNDGG*
```

SEQ ID NO: 15
Mature protein sequence of pMS2022

```
  1 DQAGKSPAGV RYHGGDEIIL QGFHWNVVRE APYNWYNILR
    QKASTIAADG

51 FSAIWMPVPW RDFSSWTDGD KSGGGEGYFW HDFNKNGLYG
    SDAQLRQAAG

101 ALGGAGVKVL YDVVPNHMNR FYPDKEINLP AGQRFWRNDC
    PDPGNGPNDC
```

```
151 DDGDRFLGGE ADLNTGHPQI YGMFRDEFTN LRSGYGAGGF
    RFDFVRGYAP

201 ERVDLWMSDS ADSSFCVGEL WKSPSEYPPW DWRNRASWQQ
    IIKDWSDRAK

251 CPVFDFALKE RMQNGSVADW KHGLNGNPDP RWREVAVTFV
    DNHDTGYSPG

301 QNGGQHKWPL PDGLIRQAYA YILTSPGTPV VYWPHMYDWG
    YGDFIRQLIQ

351 VRRTAGVRAD SAISFHSGYS GLVATVSGSQ QTLVVALNSD
    LDNPGQVASG

401 SFSEAVNAEN GQVRVWRSGS GDGGGNDGG*
```

SEQ ID NO: 16
Mature protein sequence of pMS2062

```
  1 DQAGKSPAGV RYHGGDEIIL QGFHWNVVRE APYNWYNILR
    QKASTIAADG

51 FSAIWMPVPW RDFSSWTDGD KSGGGEGYFW HDFNKNGLYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDSWMSDS ADSSFCVGEL WKKPSEYPPW DWRNRASWQE
    IIKDWSDRAK

251 CPVFDFALKE RMQNGSVADW KHGLNGNPDP RWREVAVTFV
    DNHDTGYSPG

301 QNGGQHKWPL PDGLIRQAYA YILTSPGTPV VYWPHMYDWG
    YGDFIRQLIQ

351 VRRTAGVRAD SAISFHSGYS GLVATVSGSQ QTLVVALNSD
    LDNPGQVASG

401 SFSEAVNASN GQVRVWRSGS GDGGGNDGG*
```

SEQ ID NO: 17
Mature protein sequence of pMS2171

```
  1 DQAGKSPAGV RYHGGDEIIL QGFHWNVVRE APYNWYNILR
    QKASTIAADG

51 FSAIWMPVPW RDFSSWTDGD KSGGGEGYFW HDFNKNGLYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDLWMSDS ADSSFCVGEL WKAPSEYPPW DWRNRASWQQ
    IIKDWSDRAK

251 CPVFDFALKE RMQNGSVADW KHGLNGNPDP RWREVAVTFV
    DNHDTGYSPG

301 QNGGQHKWPL PDGLIRQAYA YILTSPGTPV VYWPHMYDWG
    YGDFIRQLIQ

351 VRRTAGVRAD SAISFHSGYS GLVATVSGSQ QTLVVALNSD
    LDNPGQVASG

401 SFSEAVNAEN GQVRVWRSGS GDGGGNDGG*
```

SEQ ID NO: 18

Mature protein sequence of pMS465:

```
  1 DQAGKSPAGV RYHGGDEIIL QGFHWNVVRE APYNWYNILR
    QQASTIAADG

51 FSAIWMPVPW RDFSSWTDGD KSGGGEGYFW HDFNKNGRYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDSWMSDS ADSSFCVGEL WKSPSEYPPW DWRNTASWQQ
    IIKDWSDRAK

251 CPVFDFALKE RMQNGSVADW KHGLNGNPDP RWREVAVTFV
    DNHDTGYSPG

301 QNGGQHKWPL QDGLIRQAYA YILTSPGTPV VYWPHMYDWG
    YGDFIRQLIQ

351 VRRTAGVRAD SAISFHSGYS GLVATVSGSQ QTLVVALNSD
    LANPGQVASG

401 SFSEAVNASN GQVRVWRSGS GDGGGNDGG*
```

SEQ ID NO: 19

Mature protein sequence of pMS1042:

```
  1 DQAGKSPAGV RYHGGDEIIL QGFHWNVVRE APYNWYNILR
    QQASTIAADG

51 FSAIWMPVPW RDFSSWTDGD KSGGGEGYFW HDFNKNGRYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDSWMSDS ADSSFCVGEL WKEPSEYPPW DWRNTASWQQ
    IIKDWSDRAK

251 CPVFDFALKE RMQNGSVADW KHGLNGNPDP RWREVAVTFV
    DNHDTGYSPG

301 QNGGQHKWPL PDGLIRQAYA YILTSPGTPV VYWPHMYDWG
    YGDFIRQLIQ

351 VRRTAGVRAD SAISFHSGYS GLVATVSGSQ QTLVVALNSD
    LANPGQVASG

401 SFSEAVNASN GQVRVWRSGS GDGGGNDGG*
```

SEQ ID NO: 20

Mature protein sequence of pMS1104:

```
  1 DQAGKSPAGV RYHGGDEIIL QGFHWNVVRE APYNWYNILR
    QKASTIAADG

51 FSAIWMPVPW RDFSSWTDGD KSGGGEGYFW HDFNKNGRYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDSWMSDS ADSSFCVGEL WKEPSEYPPW DWRNTASWQQ
    IIKDWSDRAK

251 CPVFDFALKE RMQNGSVADW KHGLNGNPDP RWREVAVTFV
    DNHDTGYSPG

301 QNGGQHKWPL QDGLIRQAYA YILTSPGTPV VYWPHMYDWG
    YGDFIRQLIQ

351 VRRTAGVRAD SAISFHSGYS GLVATVSGSQ QTLVVALNSD
    LANPGQVASG

401 SFSEAVNASN GQVRVWRSGS GDGGGNDGG*
```

SEQ ID NO: 21

Mature protein sequence of pMS1153:

```
  1 DQAGKSPAGV RYHGGDEIIL QGFHWNVVRE APYNWYNILR
    QQASTIAADG

51 FSAIWMPVPW RDFSSWTDGD KSGGGEGYFW HDFNKNGLYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDSWMSDS ADSSFCVGEL WKEPSEYPPW DWRNTASWQQ
    IIKDWSDRAK

251 CPVFDFALKE RMQNGSVADW KHGLNGNPDP RWREVAVTFV
    DNHDTGYSPG

301 QNGGQHKWPL QDGLIRQAYA YILTSPGTPV VYWPHMYDWG
    YGDFIRQLIQ

351 VRRTAGVRAD SAISFHSGYS GLVATVSGSQ QTLVVALNSD
    LANPGQVASG

401 SFSEAVNASN GQVRVWRSGS GDGGGNDGG*
```

SEQ ID NO: 22

Mature protein sequence of pMS1286:

```
  1 DQAGKSPAGV RYHGGDEIIL QGFHWNVVRE APYNWYNILR
    QQASTIAADG

51 FSAIWMPVPW RDFSSWTDGD KSGGGEGYFW HDFNKNGRYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDSWMSDS ADSSFCVGEL WKEPSEYPPW DWRNRASWQQ
    IIKDWSDRAK

251 CPVFDFALKE RMQNGSVADW KHGLNGNPDP RWREVAVTFV
    DNHDTGYSPG

301 QNGGQHKWPL QDGLIRQAYA YILTSPGTPV VYWPHMYDWG
    YGDFIRQLIQ

351 VRRTAGVRAD SAISFHSGYS GLVATVSGSQ QTLVVALNSD
    LANPGQVASG

401 SFSEAVNASN GQVRVWRSGS GDGGGNDGG*
```

SEQ ID NO: 23

Mature protein sequence of pMS1284:

```
  1 DQAGKSPAGV RYHGGDEIIL QGFHWNVVRE APYNWYNILR
    QQASTIAADG

51 FSAIWMPVPW RDFSSWTDGD KSGGGEGYFW HDFNKNGRYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDSWMSDS ADSSFCVGEL WKEPSEYPPW DWRNRASWQQ
    IIKDWSDRAK

251 CPVFDFALKE RMQNGSVADW KHGLNGNPDP RWREVAVTFV
    DNHDTGYSPG

301 QNGGQHKWPL PDGLIRQAYA YILTSPGTPV VYWPHMYDWG
    YGDFIRQLIQ

351 VRRTAGVRAD SAISFHSGYS GLVATVSGSQ QTLVVALNSD
    LANPGQVASG

401 SFSEAVNASN GQVRVWRSGS GDGGGNDGG*
```

SEQ ID NO: 24

Mature protein sequence of pMS1290:

```
  1 DQAGKSPAGV RYHGGDEIIL QGFHWNVVRE APYNWYNILR
    QQASTIAADG

51 FSAIWMPVPW RDFSSWTDGD KSGGGEGYFW HDFNKNGRYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDSWMSDS ADSSFCVGEL WKEPSEYPPW DWRNKASWQQ
    IIKDWSDRAK

251 CPVFDFALKE RMQNGSVADW KHGLNGNPDP RWREVAVTFV
    DNHDTGYSPG

301 QNGGQHKWPL QDGLIRQAYA YILTSPGTPV VYWPHMYDWG
    YGDFIRQLIQ

351 VRRTAGVRAD SAISFHSGYS GLVATVSGSQ QTLVVALNSD
    LANPGQVASG

401 SFSEAVNASN GQVRVWRSGS GDGGGNDGG*
```

SEQ ID NO: 25

Mature protein sequence of pMS1484:

```
  1 DQAGKSPAGV RYHGGDEIIL QGFHWNVVRE APYNWYNILR
    QQASTIAADG

51 FSAIWMPVPW RDFSSWTDGD KSGGGEGYFW HDFNKNGRYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDLWMSDS ADSSFCVGEL WKEPSEYPPW DWRNTASWQQ
    IIKDWSDRAK

251 CPVFDFALKE RMQNGSVADW KHGLNGNPDP RWREVAVTFV
    DNHDTGYSPG

301 QNGGQHKWPL QDGLIRQAYA YILTSPGTPV VYWPHMYDWG
    YGDFIRQLIQ

351 VRRTAGVRAD SAISFHSGYS GLVATVSGSQ QTLVVALNSD
    LANPGQVASG

401 SFSEAVNASN GQVRVWRSGS GDGGGNDGG*
```

SEQ ID NO: 26

Mature protein sequence of pMS1579:

```
  1 DQAGKSPAGV RYHGGDEIIL QGFHWNVVRE APYNWYNILR
    QQASTIAADG

51 FSAIWMPVPW RDFSSWTDGD KSGGGEGYFW HDFNKNGRYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDSWMSDS ADSSFCVGEL WKEPSEYPPW DWRNTASWQQ
    IIKDWSDRAK

251 CPVFDFALKE RMQNGSVADW KHGLNGNPDP RWREVAVTFV
    DNHDTGYSPG

301 QNGGQHKWPL QDGLIRQAYA YILTSPGTPV VYWPHMYDWG
    YGDFIRQLIQ

351 VRRTAGVRAD SAISFHSGYS GLVATVSGSQ QTLVVALNSD
    LANPGQVASG

401 SFSEAVNAEN GQVRVWRSGS GDGGGNDGG*
```

SEQ ID NO: 27

Mature protein sequence of pMS1105:

```
  1 DQAGKSPAGV RYHGGDEIIL QGFHWNVVRE APYNWYNILR
    QKASTIAADG

51 FSAIWMPVPW RDFSSWTDGD KSGGGEGYFW HDFNKNGRYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDSWMSDS ADSSFCVGEL WKSPSEYPPW DWRNTASWQQ
    IIKDWSDRAK

251 CPVFDFALKE RMQNGSVADW KHGLNGNPDP RWREVAVTFV
    DNHDTGYSPG

301 QNGGQHKWPL QDGLIRQAYA YILTSPGTPV VYWPHMYDWG
    YGDFIRQLIQ

351 VRRTAGVRAD SAISFHSGYS GLVATVSGSQ QTLVVALNSD
    LANPGQVASG

401 SFSEAVNASN GQVRVWRSGS GDGGGNDGG*
```

SEQ ID NO: 28
Mature protein sequence of pMS1723:

```
  1 DQAGKSPAGV RYHGGDEIIL QGFHWNVVRE APYNWYNILR
    QKASTIAADG

51 FSAIWMPVPW RDFSSWTDGD KSGGGEGYFW HDFNKNGRYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDSWMSDS ADSSFCVGEL WKSPSEYPPW DWRNTASWQQ
    IIKDWSDRAK

251 CPVFDFALKE RMQNGSVADW KHGLNGNPDP RWREVAVTFV
    DNHDTGYSPG

301 QNGGQHKWPL QDGLIRQAYA YILTSPGTPV VYWPHMYDWG
    YGDFIRQLIQ

351 VRRTAGVRAD SAISFHSGYS GLVATVSGSQ QTLVVALNSD
    LDNPGQVASG

401 SFSEAVNASN GQVRVWRSGS GDGGGNDGG*
```

SEQ ID NO: 29
Mature protein sequence of pMS2104:

```
  1 DQAGKSPAGV RYHGGDEIIL QGFHWNVVRE APYNWYNILR
    QKASTIAADG

51 FSAIWMPVPW RDFSSWTDGD KSGGGEGYFW HDFNKNGLYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDSWMSDS ADSSFCVGEL WKAPSEYPPW DWRNRASWQQ
    IIKDWSDRAK

251 CPVFDFALKE RMQNGSVADW KHGLNGNPDP RWREVAVTFV
    DNHDTGYSPG

301 QNGGQHKWPL PDGLIRQAYA YILTSPGTPV VYWPHMYDWG
    YGDFIRQLIQ

351 VRRTAGVRAD SAISFHSGYS GLVATVSGSQ QTLVVALNSD
    LDNPGQVASG

401 SFSEAVNASN GQVRVWRSGS GDGGGNDGG*
```

SEQ ID NO: 30
Mature protein sequence of pMS2138:

```
  1 DQAGKSPAGV RYHGGDEIIL QGFHWNVVRE APYNWYNILR
    QKASTIAADG

51 FSAIWMPVPW RDFSSWTDGD KSGGGEGYFW HDFNKNGLYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDLWMSDS ADSSFCVGEL WKSPSEYPPW DWRNRASWQQ
    IIKDWSDRAK

251 CPVFDFALKE RMQNGSVADW KHGLNGNPDP RWREVAVTFV
    DNHDTGYSPG

301 QNGGQHKWPL PDGLIRQAYA YILTSPGTPV VYWPHMYDWG
    YGDFIRQLIQ

351 VRRTAGVRAD SAISFHSGYS GLVATVSGSQ QTLVVALNSD
    LDNPGQVASG

401 SFSEAVNASN GQVRVWRSGS GDGGGNDGG*
```

SEQ ID NO: 31
Mature protein sequence of pMS2124:

```
  1 DQAGKSPAGV RYHGGDEIIL QGFHWNVVRE APYNWYNILR
    QKASTIAADG

51 FSAIWMPVPW RDFSSWTDGD KSGGGEGYFW HDFNKNGLYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDLWMSDS ADSSFCVGEL WKKPSEYPPW DWRNRASWQE
    IIKDWSDRAK

251 CPVFDFALKE RMQNGSVADW KHGLNGNPDP RWREVAVTFV
    DNHDTGYSPG

301 QNGGQHKWPL PDGLIRQAYA YILTSPGTPV VYWPHMYDWG
    YGDFIRQLIQ

351 VRRTAGVRAD SAISFHSGYS GLVATVSGSQ QTLVVALNSD
    LDNPGQVASG

401 SFSEAVNAEN GQVRVWRSGS GDGGGNDGG*
```

SEQ ID NO: 32
Mature protein sequence of pMS2177:

```
  1 DQAGKSPAGV RYHGGDEIIL QGFHWNVVRE APYQWYNILR
    QKASTIAADG

51 FSAIWMPVPW RDFSSWTDGD KSGGGEGYFW HDFNKNGLYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDLWMSDS ADSSFCVGEL WKKPSEYPPW DWRNRASWQE
    IIKDWSDRAK

251 CPVFDFALKE RMQNGSVADW KHGLNGNPDP RWREVAVTFV
    DNHDTGYSPG

301 QNGGQHKWPL PDGLIRQAYA YILTSPGTPV VYWPHMYDWG
    YGDFIRQLIQ

351 VRRTAGVRAD SAISFHSGYS GLVATVSGSQ QTLVVALNSD
    LDNPGQVASG

401 SFSEAVNAEN GQVRVWRSGS GDGGGNDGG*
```

SEQ ID NO: 33
Mature protein sequence of pMS2178:

```
  1 DQAGKSPAGV RYHGGDEIIL QGFHWNVVRE APYNWYNILR
    QKASTIAADG

51 FSAIWMPVPW RDFSSWTDGD KSGGGEGYFW HDFNKNGLYG
    SDAQLRQAAQ
```

-continued

```
101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDLWMSDS ADSSFCVGEL WKKPSEYPPW DWRNRASWQE
    IIKDWSDRAK

251 CPVFDFALKE RMQNGSVADW KHGLNGNPDP RWREVAVTFV
    DNHDTGYSPG

301 QNGGQHKWPL PDGLIRQAYA YILTSPGTPV VYWPHMYDWG
    YGDFIRQLIQ

351 VRRTAGVRAD SAISFHSGYS GLVATVSGSQ QTLVVALNSD
    LDNPGQVASG

401 SFSEAVNAEN GQVRVWRSGS GDGGGNDGG*
```

SEQ ID NO: 34

Mature protein sequence of pMS2118:

```
  1 DQAGKSPAGV RYHGGDEIIL QGFHWNVVRE APYNWYNILR
    QKASTIAADG

51 FSAIWMPVPW RDFSSWTDGD KSGGGEGYFW HDFNKNGLYG
    SDAQLRQAAG

101 ALGGAGVKVL YDVVPNHMNR FYPDKEINLP AGQRFWRNDC
    PDPGNGPNDC

151 DDGDRFLGGE ADLNTGHPQI YGMFRDEFTN LRSGYGAGGF
    RFDFVRGYAP

201 ERVDLWMSDS ADSSFCVGEL WKSPSEYPPW DWRNRASWQE
    IIKDWSDRAK

251 CPVFDFALKE RMQNGSVADW KHGLNGNPDP RWREVAVTFV
    DNHDTGYSPG

301 QNGGQHKWPL PDGLIRQAYA YILTSPGTPV VYWPHMYDWG
    YGDFIRQLIQ

351 VRRTAGVRAD SAISFHSGYS GLVATVSGSQ QTLVVALNSD
    LDNPGQVASG

401 SFSEAVNAEN GQVRVWRSGS GDGGGNDGG*
```

SEQ ID NO: 35.

Linker Sequence

```
                    GSGDGGGNDGG
```

SEQ ID NO: 36:

Sequence of PS4 SBD:

```
  1 EGGLVNVNFR CDNGVTQMGD SVYAVGNVSQ LGNWSPASAV
    RLTDTSSYPT

51 WKGSIALPDG QNVEWKCLIR NEADATLVRQ WQSGGNNQVQ
    AAAGASTSGS

101 F*
```

SEQ ID NO: 37

```
                    HGGDEIILQFHWN
```

SEQ ID NO: 38

```
            DGF-X1-AIW-X2-P-X3-PWRD-X4-SSW
```

SEQ ID NO: 39

```
                         GGEGYFW
```

SEQ ID NO: 40

```
                          VPNH
```

SEQ ID NO: 41

```
                          CDDGD
```

SEQ ID NO: 42

```
                        AGGFRFDFVRG
```

SEQ ID NO: 43

```
                           FALK
```

SEQ ID NO: 44

```
                      WREVAVTFVDNHD
```

SEQ ID NO: 45

```
                           GYSPG
```

SEQ ID NO: 46

```
                            GQH
```

SEQ ID NO: 47

```
                           AYAYI
```

SEQ ID NO: 48

```
                           SPGTP
```

SEQ ID NO: 49

```
                            VYW
```

SEQ ID NO: 50

```
                          HMYDWG
```

SEQ ID NO: 51:

Novamyl:

```
SSSASVKGDVIYQIIIDRFYDGDTTNNNPAKSYGLYDPTKSKWKMYWGGD
LEGVRQKLPYLKQLGVTTIWLSPVLDNLDTLAGTDNTGYHGYWTRDFKQI
EEHFGNWTTFDTLVNDAHQNGIKVIVDFVPNHSTPFKANDSTFAEGGALY
NNGTYMGNYFDDATKGYFHHNGDISNWDDRYEAQWKNFTDPAGFSLADLS
```

-continued

```
QENGTIAQYLTDAAVQLVAHGADGLRIDAVKHFNSGFSKSLADKLYQKKD

IFLVGEWYGDDPGTANHLEKVRYANNSGVNVLDFDLNTVIRNVFGTFTQT

MYDLNNMVNQTGNEYKYKENLITFIDNHDMSRFLSVNSNKANLHQALAFI

LTSRGTPSIYYGTEQYMAGGNDPYNRGMMPAFDTTTTAFKEVSTLAGLRR

NNAAIQYGTTTQRWINNDVYIYERKFFNDVVLVAINRNTQSSYSISGLQT

ALPNGSYADYLSGLLGGNGISVSNGSVASFTLAPGAVSVWQYSTSASAPQ

IGSVAPNMGIPGNVVTIDGKGFGTTQGTVTFGGVTATVKSWTSNRIEVYV

PNMAAGLTDVKVTAGGVSSNLYSYNILSGTQTSVVFTVKSAPPTNLGDKI

YLTGNIPELGNWSTDTSGAVNNAQGPLLAPNYPDWFYVFSVPAGKTIQFK

FFIKRADGTIQWENGSNHVATTPTGATGNITVTWQN
```

SEQ ID NO: 52:

Nucleotide sequence of pMS382:

```
   1 gatcaagcag gaaaaagccc ggcaggcgtc agatatcatg
     gcggcgatga aatcatcctt 61 cagggctttc attggaacgt cgtcagagaa gcgccgtata
     actggtataa catcctgaga 121 caacaagcga gcacaattgc cgctgatggc ttttccgcaa
     tctggatgcc ggttccgtgg 181 agagatttta gcagctggac ggatggagat aaaagcggag
     gcggcgaagg atatttttgg 241 catgacttta acaaaaacgg ccgctatgga agcgatgctc
     aactgagaca agcagcagga 301 gcacttggag gagcaggagt caaagtcctg tacgatgtcg
     tcccgaacca tatgaaccgc 361 ttttatccgg acaaagaaat caatctgccg gcaggccaaa
     gattttggag aaacgattgc 421 ccggacccgg gaaatggacc gaatgattgc gatgatggcg
     atagatttct gggcggcgaa 481 gcggatctga atacaggcca tccgcaaatc tatggcatgt
     ttcgggacga atttacgaat 541 ctgagaagcg gatatggagc gggcggattt cgctttgatt
     ttgtcagagg ctatgccccg 601 gaaagagttg atagctggat gagcgattca gcggatagca
     gcttttgcgt cggcgaactt 661 tggaaagaac cgagcgaata tccgccgtgg gattggagaa
     atacagcgag ctggcagcag 721 atcatcaaag attggagcga tagagcaaaa tgcccggtct
     ttgactttgc cctgaaagaa 781 cgcatgcaaa atggaagcgt cgccgattgg aaacatggcc
     tgaacggaaa tccggacccg 841 agatggagag aagtcgccgt cacgtttgtc gataaccatg
     acacaggata tagcccggga 901 caaaatggag gacaacataa atggccgctt caagatggcc
     ttatcagaca ggcgtatgcc 961 tatatccttaca tcaccggg aacaccggtt gtttattggc
     cgcatatgta tgattgggc 1021 tatggcgatt tcatccgcca actgatccag gttagaagaa
     cagcaggagt cagagcggat 1081 agcgccatta gctttcatag cggctatagc ggacttgtcg
     ctacagttag cggcagccaa
```

-continued

```
1141 caaacactgg tcgtcgccct gaatagcgat ctggcaaatc
     cgggacaagt tgctagcggc 1201 agctttagcg aagcagtcaa tgccagcaat ggccaagtca
     gagtctggag aagcggaagc 1261 ggagatggag gaggaaatga cggaggataa
```

Note: The derived N-terminus of this nucleotide sequence is DQA . . . . However, the final construct may be extended at the 5'end with atg to encode M at the N-terminus.

The invention is further described by the following numbered paragraphs:

1. A polypeptide having amylase activity comprising an amino acid sequence having
   a. at least 65% sequence identity to the amino acid sequence of SEQ ID NO: 1, and wherein the polypeptide comprises one or more amino acid substitutions at the following positions: 88 or 205, and/or
   b. at least 78% sequence identity to the amino acid sequence of SEQ ID NO: 1, and wherein the polypeptide comprises one or more amino acid substitutions at the following positions: 16, 48, 97, 105, 235, 240, 248, 266, 311, 347, 350, 362, 364, 369, 393, 395, 396, 400, 401, 403, 412 or 409, and/or
   c. at least 78% sequence identity to the amino acid sequence of SEQ ID NO: 1, and wherein the polypeptide comprises one or more of the following amino acid substitutions: 42K/A/V/N/I/H/F, 34Q, 100Q/K/N/R, 272D, 392 K/D/E/Y/N/Q/R/T/G or 399C/H, and/or
   d. at least 95% sequence identity to the amino acid sequence of SEQ ID NO: 1, and wherein the polypeptide comprises one or more amino acid substitutions at the following positions: 44, 96, 204, 354 or 377, and/or
   e. at least 95% sequence identity to the amino acid sequence of SEQ ID NO: 1, and wherein the polypeptide comprises the following amino acid substitution: 392S
   wherein an amino acid substitution is relative to the corresponding amino acid of SEQ ID NO:1 and the positions are with reference to the position numbering of the sequence shown as SEQ ID NO: 1.

2. A polypeptide having amylase activity comprising an amino acid sequence having at least 65% sequence identity to the amino acid sequence of SEQ ID NO: 1, and wherein the polypeptide comprises one or more amino acid substitutions at the following positions: 88, or 205 and/or one or more of the following amino acid substitutions: 42K, 235H/K/R, 240E, 392 K/D/E/Y or 409E wherein an amino acid substitution is relative to the corresponding amino acid of SEQ ID NO:1 and the positions are with reference to the position numbering of the sequence shown as SEQ ID NO: 1.

3. The polypeptide according to embodiment 1, wherein the polypeptide comprises one or more amino acid substitutions at the following positions: 88, 205, 235, 240, 248, 266, 311, 377 or 409 and/or one or more of the following amino acid substitutions: 42K/A/V/N/I/H/F, 34Q, 100Q/K/N/R, 272D or 392K/D/E/Y/N/Q/R/S/T/G.

4. The polypeptide according to any one of embodiments 1 and 3, wherein the polypeptide comprises one or more amino acid substitutions at the following positions: 88, 205, 235, 240, 311 or 409 and/or one or more of the following amino acid substitutions: 42K/N/I/H/F, 272D, or 392 K/D/E/Y/N/Q/R/S/T/G.

5. The polypeptide according to any one of embodiments 1 and 3-4, wherein the polypeptide comprises amino acid substitutions at least in four, five or in all of the following positions: 88, 205, 235, 240, 311 or 409 and/or has at least one, or two the following amino acid substitutions: 42K/N/I/H/F, 272D or 392 K/D/E/Y/N/Q/R/S/T/G.
6. The polypeptide according to any one of embodiments 1-5, wherein the polypeptide further comprises one or more of the following amino acids 33Y, 34N, 70D, 121F, 134R, 141P, 146G, 157L, 161A, 178F, 179T, 223E/S/K/A, 229P, 307K, 309P or 334P.
7. The polypeptide according to any one of embodiments 1-6, wherein the polypeptide further has the following amino acids 33Y, 34N, 70D, 121F, 134R, 141P, 146G, 157L, 161A, 178F, 179T, 229P, 307K, 309P and 334P.
8. The polypeptide according to any one of embodiments 1-6, wherein the polypeptide has at least one of the amino acid substitutions in b) of embodiment 1 and further comprises one or more amino acid substitutions at the following positions: 44, 96, 204, 354 or 377.
9. The polypeptide according to any one of embodiments 1-8 having at least 66, 68, 70, 72, 74, 76, 78, 80, 82, 84, 86, 88, 90, 91, 92, 93, 94, 95, 96, 97, 98, or 99% sequence identity to the amino acid sequence of SEQ ID NO: 1.
10. The polypeptide according to any one of the embodiments 1-9, wherein the polypeptide has the amino acid 34Q.
11. The polypeptide according to any one of the embodiments 1 and 2-10, wherein the polypeptide has the amino acid 42K/F/H/I/N/A/V.
12. The polypeptide according to any one of the embodiments 1 and 2-10, wherein the polypeptide has the amino acid 42K/F/H/I/N.
13. The polypeptide according to any one of the embodiments 1-12, wherein the polypeptide has the amino acid 42K.
14. The polypeptide according to any one of the embodiments 1-13, wherein the polypeptide comprises an amino acid substitution in position 88.
15. The polypeptide according to any one of the embodiments 1-14, wherein the polypeptide has the amino acid 88L/Y/K.
16. The polypeptide according to any one of the embodiments 1-15, wherein the polypeptide has the amino acid 88L.
17. The polypeptide according to any one of the embodiments 1-16, wherein the polypeptide has the amino acid 88Y.
18. The polypeptide according to any one of the embodiments 1-17, wherein the polypeptide comprises an amino acid substitution in position 205.
19. The polypeptide according to any one of the embodiments 1-18, wherein the polypeptide has the amino acid 205L/K/M/N/Q/R/V/Y.
20. The polypeptide according to any one of the embodiments 1-19, wherein the polypeptide has the amino acid 205L/K/M/N/Q/R/V.
21. The polypeptide according to any one of the embodiments 1-20, wherein the polypeptide has the amino acid 205L.
22. The polypeptide according to any one of the embodiments 1 and 2-21, wherein the polypeptide comprises an amino acid substitution in position 235.
23. The polypeptide according to any one of the embodiments 1 and 2-22, wherein the polypeptide has the amino acid 235H/K/R/Q/S.
24. The polypeptide according to any one of the embodiments 1 and 2-23, wherein the polypeptide has the amino acid 235H/K/R/Q.
25. The polypeptide according embodiment 2 or 24, wherein the polypeptide has the amino acid 235H/K/R.
26. The polypeptide according to embodiment 2 or 25, wherein the polypeptide has the amino acid 235R.
27. The polypeptide according to embodiment 2 or 25, wherein the polypeptide has the amino acid 235H.
28. The polypeptide according to embodiment 2 or 25, wherein the polypeptide has the amino acid 235K.
29. The polypeptide according to any one of the embodiments 1 and 2-28, wherein the polypeptide comprises an amino acid substitution in position 240.
30. The polypeptide according to embodiment 29, wherein the polypeptide has the amino acid 240E/H/M/D/S.
31. The polypeptide according to embodiment 29, wherein the polypeptide has the amino acid 240E/H/M/D.
32. The polypeptide according to embodiment 2 or 29, wherein the polypeptide has the amino acid 240E.
33. The polypeptide according to any one of the embodiments 1-32, wherein the polypeptide has the amino acid 272D.
34. The polypeptide according to any one of the embodiments 1-33, wherein the polypeptide comprises an amino acid substitution in position 311.
35. The polypeptide according to embodiment 2 or 34, wherein the polypeptide has the amino acid 311P.
36. The polypeptide according to any one of the embodiments 1 and 2-35, wherein the polypeptide comprises an amino acid substitution in position 409.
37. The polypeptide according to embodiment 36, wherein the polypeptide has the amino acid 409H/Q/T/E.
38. The polypeptide according to embodiment 2 or 37, wherein the polypeptide has the amino acid 409E.
39. The polypeptide according to any one of the embodiments 1-38, wherein the polypeptide has the amino acid 100Q/K/N/R.
40. The polypeptide according to embodiment 39, wherein the polypeptide has the amino acid 100Q.
41. The polypeptide according to any one of the embodiments 1 and 2-39, wherein the polypeptide has the amino acid 392D/E/K/Y/N/Q/R/S/T/G.
42. The polypeptide according to embodiment 41, wherein the polypeptide has the amino acid 392D/E/K/Y/N/Q/R/S/T.
43. The polypeptide according to embodiment 2 or 41, wherein the polypeptide has the amino acid 392D/E/K/Y.
44. The polypeptide according to embodiment 43, wherein the polypeptide has the amino acid 392D.
45. The polypeptide according to embodiment 43, wherein the polypeptide has the amino acid 392E.
46. The polypeptide according to embodiment 43, wherein the polypeptide has the amino acid 392K.
47. The polypeptide according to embodiment 43, wherein the polypeptide has the amino acid 392Y.
48. The polypeptide according to any one of the embodiments 1-47, wherein the polypeptide has both of the following amino acids 235R and 311P.
49. The polypeptide according to any one of the embodiments 1-48, wherein the polypeptide comprises an amino acid substitution in position 16.

50. The polypeptide according to embodiment 49, wherein the polypeptide has the amino acid 16/A/E/K.
51. The polypeptide according to any one of the embodiments 1-50, wherein the polypeptide comprises an amino acid substitution in position 48.
52. The polypeptide according to embodiment 51, wherein the polypeptide has the amino acid 48/C/L.
53. The polypeptide according to any one of the embodiments 1-52, wherein the polypeptide comprises an amino acid substitution in position 97.
54. The polypeptide according to any one of the embodiments 1-53, wherein the polypeptide comprises an amino acid substitution in position 105.
55. The polypeptide according to embodiment 54, wherein the polypeptide has the amino acid 105/N/R.
56. The polypeptide according to any one of the embodiments 1-55, wherein the polypeptide comprises an amino acid substitution in position 248.
57. The polypeptide according to any one of the embodiments 1-56, wherein the polypeptide comprises an amino acid substitution in position 266.
58. The polypeptide according to any one of the embodiments 1-57, wherein the polypeptide comprises an amino acid substitution in position 347.
59. The polypeptide according to embodiment 58, wherein the polypeptide has the amino acid 347/C/D/H/K.
60. The polypeptide according to any one of the embodiments 1-59, wherein the polypeptide comprises an amino acid substitution in position 350.
61. The polypeptide according to embodiment 60, wherein the polypeptide has the amino acid 350E/H/N.
62. The polypeptide according to any one of the embodiments 1-61, wherein the polypeptide comprises an amino acid substitution in position 354.
63. The polypeptide according to embodiment 62, wherein the polypeptide has the amino acid 354D/E.
64. The polypeptide according to any one of the embodiments 1-63, wherein the polypeptide comprises an amino acid substitution in position 362.
65. The polypeptide according to embodiment 64, wherein the polypeptide has the amino acid 362E/H/P.
66. The polypeptide according to any one of the embodiments 1-65, wherein the polypeptide comprises an amino acid substitution in position 364.
67. The polypeptide according to embodiment 66, wherein the polypeptide has the amino acid 364E/K/NQ.
68. The polypeptide according to any one of the embodiments 1-67, wherein the polypeptide comprises an amino acid substitution in position 369.
69. The polypeptide according to embodiment 68, wherein the polypeptide has the amino acid 369I/N.
70. The polypeptide according to any one of the embodiments 1-69, wherein the polypeptide comprises an amino acid substitution in position 377.
71. The polypeptide according to any one of the embodiments 1-70, wherein the polypeptide comprises an amino acid substitution in position 393.
72. The polypeptide according to embodiment 71, wherein the polypeptide has the amino acid 393D/E/K.
73. The polypeptide according to any one of the embodiments 1-72, wherein the polypeptide comprises an amino acid substitution in position 395.
74. The polypeptide according to embodiment 73, wherein the polypeptide has the amino acid 395C/E/K.
75. The polypeptide according to any one of the embodiments 1-74, wherein the polypeptide comprises an amino acid substitution in position 396.
76. The polypeptide according to embodiment 75, wherein the polypeptide has the amino acid 396D/E.
77. The polypeptide according to any one of the embodiments 1-76, wherein the polypeptide comprises an amino acid substitution in position 399.
78. The polypeptide according to embodiment 77, wherein the polypeptide has the amino acid 399C/H.
79. The polypeptide according to any one of the embodiments 1-78, wherein the polypeptide comprises an amino acid substitution in position 400.
80. The polypeptide according to embodiment 79, wherein the polypeptide has the amino acid 400S/W.
81. The polypeptide according to any one of the embodiments 1-80, wherein the polypeptide comprises an amino acid substitution in position 401.
82. The polypeptide according to embodiment 81, wherein the polypeptide has the amino acid 401D/K.
83. The polypeptide according to any one of the embodiments 1-82, wherein the polypeptide comprises an amino acid substitution in position 403.
84. The polypeptide according to embodiment 83, wherein the polypeptide has the amino acid 403E/T/V.
85. The polypeptide according to any one of the embodiments 1-84, wherein the polypeptide comprises an amino acid substitution in position 412.
86. The polypeptide according to embodiment 85, wherein the polypeptide has the amino acid 412D/N.
87. The polypeptide according to any one of the embodiments 1-86, wherein the polypeptide further comprises one or more of the following amino acids 121F, 134R, 141P, 229P, or 307K.
88. The polypeptide according to any one of embodiments 1-87, wherein the polypeptide has one or more of the following amino acids 42K, 88L, 205L, 235R, 240E, 272D, 311P, 392D, and 409E.
89. The polypeptide according to any one of embodiments 1-88, wherein the polypeptide comprises the following amino acids 42K, 88L, 235R, 311P, 392D and either 223S, 223K or 223A.
90. The polypeptide according to embodiment 89 further comprising one or more selected from the group consisting of 272D, 409E, 205L or 240E.
91. The polypeptide according to any one of embodiments 1-90, wherein the polypeptide has at least four, five, six, seven or eight of the following amino acids 42K, 88L, 205L, 235R, 240E, 272D, 311P, 392D, or 409E.
92. The polypeptide according to any one of embodiments 1-91, wherein the polypeptide has the amino acid 223A/K/S.
93. The polypeptide according to any one of embodiments 1-92, wherein the polypeptide has the following amino acids 42K, 88L, 223S, 235R, 311P and 392D.
94. The polypeptide according to any one of embodiments 1-93, wherein the polypeptide has the following amino acids 42K, 88L, 223K, 235R, 272D, 311P and 392D.
95. The polypeptide according to any one of embodiments 1-94, wherein the polypeptide has the following amino acids 42K, 88L, 223S, 235R, 311P, 392D and 409E.
96. The polypeptide according to any one of embodiments 1-95, wherein the polypeptide has the following amino acids 42K, 88L, 205L, 223S, 235R, 311P, 392D and 409E.
97. The polypeptide according to any one of embodiments 1-96, wherein the polypeptide has the following amino acids 42K, 88L, 205L, 223K, 240E, 235R, 311P, 392D and 409E.

98. The polypeptide according to any one of embodiments 1-97, wherein the polypeptide has the following amino acids 42K, 88L, 205L, 223A, T235R, 311P, 392D and 409E.
99. The polypeptide according to any one of embodiments 1-98 comprising an amino acid sequence selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34.
100. The polypeptide according to any one of embodiments 1-99 comprising an amino acid sequence selected from the group consisting of SEQ ID NO: 12, SEQ ID NO: 13, SEQ ID NO: 14, SEQ ID NO: 15, SEQ ID NO: 16, and SEQ ID NO: 17.
101. The polypeptide according to any one of embodiments 1-100 having an amino acid sequence selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34, and optionally one or more additional amino acids at the N-terminus.
102. The polypeptide according to embodiment 101 having an amino acid sequence selected from the group consisting of SEQ ID NO: 12, SEQ ID NO: 13, SEQ ID NO: 14, SEQ ID NO: 15, SEQ ID NO: 16, and SEQ ID NO: 17, and optionally one or more additional amino acids at the N-terminus.
103. The polypeptide according to any one of the embodiments 101-102 wherein said one or more additional amino acids at the N-terminus is one M.
104. The polypeptide according to any one of embodiments 1-103, wherein the polypeptide comprises one or more amino acid substitutions at the following positions: 88, 205, 235 or 409 and/or one or more of the following amino acid substitutions: 42K, 34Q, 100Q, 223A/S, 240E, 311P, 392D, or 409E with reference to the position numbering of the sequence shown as SEQ ID NO: 1.
105. The polypeptide according to any one of embodiments 1-104, wherein the polypeptide comprises one or more of the following amino acid substitutions: 42K, 34Q, 88K/L/Y, 100Q, 205L, 223A/S/K, 235K/H/Q/R, 240E/D, 248H, 266T, 311P, 377D/E/P, 392K/D/Y or 409E.
106. The polypeptide according to any one of embodiments 1-105, wherein the polypeptide comprises one or more of the following amino acid substitutions: 34Q, 42K, 88L, 100Q, 205L, 223A/S/K, 235K/R, 240E, 311P, 392D or 409E.
107. The polypeptide according to embodiment 106, wherein the polypeptide comprises the following amino acid substitutions: 235R and 311P.
108. The polypeptide according to any one of the embodiments 1-107, wherein the polypeptide comprises the amino acid substitution 42K.
109. The polypeptide according to any one of the embodiments 1-108, wherein the polypeptide comprises the following amino acid substitutions: 42K and 223S.
110. The polypeptide according to any one of the embodiments 1-109, wherein the polypeptide comprises the following amino acid substitutions: 42K, 223S and 392D.
111. The polypeptide according to any one of the embodiments 1-110, wherein the polypeptide comprises the following amino acid substitutions: 42K, 88L, 223A, 235R, 311P and 392D.
112. The polypeptide according to any one of the embodiments 1-111, wherein the polypeptide comprises the following amino acid substitutions: 42K, 88L, 205L, 223S, 235R, 240E, 311P, 392D and 409E.
113. The polypeptide according to any one of the embodiments 1-112, wherein the polypeptide comprises the following amino acid substitutions: 42K, 88L, 205L, 223K, 235R, 240E, 311P, 392D and 409E.
114. The polypeptide according to any one of the embodiments 1-113, wherein the polypeptide comprises the following amino acid substitutions: 42K, 88L, 205L, 223S, 235R, 311P and 392D.
115. The polypeptide according to any one of the embodiments 1-114, wherein the polypeptide comprises the following amino acid substitutions: 34Q, 42K, 88L, 205L, 223K, 235R, 240E, 311P, 392D and 409E.
116. The polypeptide according to any one of the embodiments 1-115, wherein the polypeptide comprises the following amino acid substitutions: 42K, 88L, 100Q, 205L, 223K, 235R, 240E, 311P, 392D and 409E.
117. The polypeptide according to any one of embodiments 1-116 further comprising a starch binding domain at the C-terminus.
118. The polypeptide according to embodiment 117 wherein the starch binding domain is the residues of SEQ ID NO: 36.
119. The polypeptide according to any one of embodiments 1-118 having a linker fused at the C-terminus.
120. The polypeptide according to embodiment 119, wherein the linker is the residues of SEQ ID NO: 35.
121. The polypeptide according to any one of embodiments 1-120 having exoamylase activity.
122. The polypeptide according to any one of embodiments 1-121 having non-maltogenic exoamylase activity.
123. The polypeptide according to any one of embodiments 1-122, wherein the polypeptide exhibits improved thermo-stability when compared to the SEQ ID NO: 1 or SEQ ID NO: 10.
124. The polypeptide according to any one of embodiments 1-123, in which the half life (t½), preferably at 60 degrees C., is increased by 15% or more, preferably 50% or more, most preferably 100% or more, relative to SEQ ID NO: 1 or SEQ ID NO: 10.
125. The polypeptide according to any one of embodiments 1-124, in which a food product treated with the polypeptide has any one or more, preferably all of the following properties: (a) lower firmness; (b) higher resilience; (c) higher cohesiveness; (d) lower crumbliness; and (e) higher foldability compared to a food product which has been treated with SEQ ID NO: 1 or SEQ ID NO: 10.
126. The polypeptide according to any one of embodiments 1-125, in which the resilience, cohesiveness or foldability of the food product treated with the polypeptide is independently increased by 15% or more, preferably 50% or more, most preferably 100% or more, relative to a food product which has been treated with SEQ ID NO: 1 or SEQ ID NO: 10.

127. The polypeptide according to any one of embodiments 1-126, in which each of resilience cohesiveness and foldability of a food product treated with the polypeptide is increased compared to a food product which has been treated with SEQ ID NO: 1 or SEQ ID NO: 10.

128. The polypeptide according to any one of embodiments 1-127, in which the firmness or the crumbliness of the food product treated with the polypeptide is independently decreased by 15% or more, preferably 50% or more, most preferably 100% or more, relative to a food product which has been treated with SEQ ID NO: 1 or SEQ ID NO: 10.

129. The polypeptide according to any one of embodiments 1-128, in which each of the firmness and crumblines of a food product treated with the polypeptide is decreased compared to a food product which has been treated with SEQ ID NO: 1 or SEQ ID NO: 10.

130. Use of a polypeptide as described in any of embodiments 1-129 as a food or feed additive.

131. A process for treating a starch comprising contacting the starch with a polypeptide as described in any of embodiments 1-129 and allowing the polypeptide to generate from the starch one or more linear products.

132. Use of a polypeptide as described in any of embodiments 1-129 in preparing a food or feed product.

133. A process of preparing a food or feed product comprising admixing a polypeptide as described in any of embodiments 1-129 with a food or feed ingredient.

134. Use according to embodiment 130, or a process according to embodiment 133, in which the food product comprises a dough or a dough product, preferably a processed dough product.

135. A use or process according to any of embodiments 130 to 133, in which the food product is a bakery product.

136. A process for making a bakery product comprising: (a) providing a starch medium; (b) adding to the starch medium a polypeptide as described in any of embodiments 1-129; and (c) applying heat to the starch medium during or after step (b) to produce a bakery product.

137. A food product, feed product, dough product or a bakery product obtained by a process according to any of embodiments 130 to 136.

138. An improver composition for a dough, in which the improver composition comprises a polypeptide as described in any of embodiments 1-129, and at least one further dough ingredient or dough additive.

139. A composition comprising a flour and a polypeptide as described in any of embodiments 1-129.

140. Use of a polypeptide as described in any of embodiments 1-129, in a dough product to retard or reduce staling, preferably detrimental retrogradation, of the dough product.

141. Use of a polypeptide as described in any of embodiments 1-129, in a dough product to improve any one or more of firmness, resilience, cohesiveness, crumbliness or foldability of the dough product.

142. A combination of a polypeptide as described in any of embodiments 1-129, together with any one or more of the following:
   a. maltogenic alpha-amylase also called glucan 1,4-α-maltohydrolase (EC 3.2.1.133) from *Bacillus stearothermophilus*, or a variant, homologue, or mutants thereof which have maltogenic alpha-amylase activity;
   b. a bakery xylanase (EC 3.2.1.8) from e.g. *Bacillus* sp., *Aspergillus* sp., *Thermomyces* sp. or *Trichoderma* sp.;
   c. α-amylase (EC 3.2.1.1) from *Bacillus amyloliqufaciens* or a variant, homologue, or mutants thereof which have alpha-amylase activity; and
   d. a lipase such as glycolipase from *Fusarium heterosporum*.

143. Use of a combination according to embodiment 142 for an application according to any preceding embodiment.

144. A food or feed product produced by treatment with a combination according to embodiment 142.

145. A nucleic acid capable of encoding a polypeptide according to any of embodiments 1 to 129.

146. A nucleic acid according to embodiment 145 having a nucleic acid sequence which at least 78% identical to SEQ ID NO: 52.

147. A nucleic acid comprising a fragment of at least 60 residues of a nucleic acid according to embodiment 145 or 146 which is capable of encoding a polypeptide having non-maltogenic exoamylase activity.

148. A plasmid comprising a nucleic acid according to any of embodiments 145 to 147.

149. An expression vector comprising a nucleic acid according to any of embodiments 145 to 147, or capable of expressing a polypeptide according to any of embodiments 1 to 129.

150. A host cell comprising, preferably transformed with, a plasmid according to embodiment 148 or an expression vector according to embodiment 149.

151. A cell capable of expressing a polypeptide according to any of embodiments 1 to 129.

152. A host cell according to embodiment 150, or a cell according to embodiment 151, which is a bacterial, fungal or yeast cell.

153. A method of expressing a polypeptide, the method comprising obtaining a host cell or a cell according to embodiment 150, 151 or 152 and expressing the polypeptide from the cell or host cell, and optionally purifying the polypeptide.

154. A method of producing a polypeptide according to any of embodiment 1 to 129, the method comprising introducing an amino acid substitution into SEQ ID NO: 1 having non-maltogenic exoamylase activity, the amino acid substitution being
   a. in one or more positions selected from the group consisting of: 16, 48, 88, 97, 105, 205, 235, 240, 248, 266, 311, 347, 350, 362, 364, 369, 393, 395, 396, 400, 401, 403, 412 and 409 and/or
   b. one or more of the following amino acid substitutions: 42K/A/V/N/I/H/F, 34Q, 100Q/K/N/R, 272D, 392 K/D/E/Y/N/Q/R/T/G or 399C/H and/or
   c. in one or more positions selected from the group consisting of: 44, 96, 204, 354 and 377 and/or
   d. the following amino acid substitution: 392S.

155. The polypeptide according to any one of embodiments 1-129 comprising the sequence DGF-X1-AIW-X2-P-X3-PWRD-X4-SSW (SEQ ID NO: 38), wherein X1 is S or T, X2 is M or L, X3 is V or P and X4 is any natural occurring amino acid residue, preferably an L-amino acid, at the positions corresponding to positions 49-66 with reference to the position numbering of the sequence shown as SEQ ID NO: 1.

156. The polypeptide according to any one of embodiments 1-129 and 155 comprising the sequence GGEGYFW (SEQ ID NO: 39) at the positions corresponding to positions 79-85 with reference to the position numbering of the sequence shown as SEQ ID NO: 1.

157. The polypeptide according to any one of embodiments 1-129 and 155-156 comprising the sequence VPNH (SEQ ID NO: 40) at the positions corresponding to positions 114-117 with reference to the position numbering of the sequence shown as SEQ ID NO: 1.

158. The polypeptide according to any one of embodiments 1-129 and 155-157 comprising the sequence CDDGD (SEQ ID NO: 41) at the positions corresponding to positions 150-154 with reference to the position numbering of the sequence shown as SEQ ID NO: 1.

159. The polypeptide according to any one of embodiments 1-129 and 155-158 comprising the sequence AGGFRFDFVRG (SEQ ID NO: 42) at the positions corresponding to positions 187-197 with reference to the position numbering of the sequence shown as SEQ ID NO: 1.

160. The polypeptide according to any one of embodiments 1-129 and 155-159 comprising the sequence FALK (SEQ ID NO: 43) at the positions corresponding to positions 256-259 with reference to the position numbering of the sequence shown as SEQ ID NO: 1.

161. The polypeptide according to any one of embodiments 1-129 and 155-160 comprising the sequence WREVAVTFVDNHD (SEQ ID NO: 44) at the positions corresponding to positions 282-294 with reference to the position numbering of the sequence shown as SEQ ID NO: 1.

162. The polypeptide according to any one of embodiments 1-129 and 155-161 comprising the sequence GYSPG (SEQ ID NO: 45) at the positions corresponding to positions 296-300 with reference to the position numbering of the sequence shown as SEQ ID NO: 1.

163. The polypeptide according to any one of embodiments 1-129 and 155-162 comprising the sequence GQH (SEQ ID NO: 46) at the positions corresponding to positions 304-306 with reference to the position numbering of the sequence shown as SEQ ID NO: 1.

164. The polypeptide according to any one of embodiments 1-129 and 155-163 comprising the sequence AYAYI (SEQ ID NO: 47) at the positions corresponding to positions 318-322 with reference to the position numbering of the sequence shown as SEQ ID NO: 1.

165. The polypeptide according to any one of embodiments 1-129 and 155-164 comprising the sequence SPGTP (SEQ ID NO: 48) at the positions corresponding to positions 325-329 with reference to the position numbering of the sequence shown as SEQ ID NO: 1.

166. The polypeptide according to any one of embodiments 1-129 and 155-165 comprising the sequence VYW (SEQ ID NO: 49) at the positions corresponding to positions 331-333 with reference to the position numbering of the sequence shown as SEQ ID NO: 1.

167. The polypeptide according to any one of embodiments 1-129 and 155-166 comprising the sequence HMYDWG (SEQ ID NO: 50) at the positions corresponding to positions 335-340 with reference to the position numbering of the sequence shown as SEQ ID NO: 1.

168. The polypeptide according to any one of embodiments 1-129 and 155-167 comprising the sequence HGGDEIILQFHWN (SEQ ID NO: 37) at the positions corresponding to positions 13-26 with reference to the position numbering of the sequence shown as SEQ ID NO: 1.

169. A method of producing a polypeptide according to any of embodiments 1 to 129 and 155-167, the method comprising introducing an amino acid substitution into SEQ ID NO: 1 having non-maltogenic exoamylase activity, the amino acid substitution being in one or more of the following positions: 88, or 205 and/or being one or more of the following amino acid substitutions: 42K, 235H/K/R, 240E, 392 K/D/E/Y or 409E.

170. A method of making a saccharide syrup, comprising adding a polypeptide according to any one of embodiments 1 to 129 and 155-167 to a granular starch liquefact to form the saccharide syrup.

171. The method of embodiment 170, wherein the granular starch liquefact is produced by an alpha-amylase.

172. The method of embodiment 170, wherein the granular starch liquefact is an acid produced liquefact.

173. The method of embodiment 170, wherein the granular starch liquefact is obtained from starch from corns, cobs, wheat, barley, rye, milo, sago, cassava, tapioca, sorghum, rice, peas, bean, banana, or potatoes.

174. The method of embodiment 170, wherein the granular starch liquefact is saccharified at 55° C. to 65° C.

175. The method of embodiment 170, wherein the granular starch liquefact is saccharified at 60° C. to 65° C.

176. The method of embodiment 170, wherein the granular starch liquefact is saccharified at pH 5.0 to pH 7.0.

177. The method of embodiment 170, further comprising a step of adding an enzyme having debranching activity to the granular starch liquefact.

178. The method of embodiment 177, wherein the enzyme having debranching activity is, an isoamylase, a pullulanase, an isopullulanase, a neopullulanase or any combination thereof.

179. The method of embodiment 177, optionally comprising a further step of adding a protease, a cellulase, a hemicellulase, a lipase, a cutinase, a pectate liase or any combination thereof to the granular starch.

180. The method of embodiment 170, wherein the saccharide syrup comprises at least 35% by weight maltotetraose based on total saccharide content.

181. The method of embodiment 180, wherein the saccharide syrup comprises at least 45% by weight maltotetraose based on total saccharide content.

182. The method of embodiment 181, wherein the saccharide syrup comprises at least 50% by weight maltotetraose based on total saccharide content.

The method of embodiment 182, wherein the saccharide syrup comprises from 40% by weight to 60% by weight maltotetraose based on total saccharide content.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A recombinantly produced polypeptide having amylase activity comprising an amino acid sequence having at least 90% sequence identity to the amino acid sequence of SEQ ID NO: 1, and wherein the polypeptide comprises one or more amino acid substitutions at the following positions: 235, 240, 311, 350, 364, or 409 with reference to the position numbering of the sequence shown in SEQ ID NO: 1.

2. The polypeptide according to claim 1, wherein the polypeptide further comprises:
one or more of the following amino acids 33Y, 34N, 70D, 121F, 134R, 141P, 146G, 157L, 161A, 178F, 179T, 223E/S/K/A, 229P, 307K, 309P and 334P;
one or more amino acid substitutions at positions 88 or 205;
one or more of the following amino acid substitutions: 42K/A/V/N/I/H/F, 34Q, 100Q/K/N/R, 272D, 392 K/D/E/Y/N/Q/R/T/G or 399C/H;
one or more amino acid substitutions at positions 44, 96, 204, 354 or 377; or
a substitution at position 392S.

3. The polypeptide according to claim 2, wherein the polypeptide comprises one or more amino acid substitutions at the following positions: 235, 88, 205, 240, 248, 266, 311, 377 or 409 and one or more of the following amino acid substitutions: 42K/A/V/N/I/H/F, 34Q, 100Q/K/N/R, 272D or 392K/D/E/Y/N/Q/R/S/T/G.

4. The polypeptide according to claim 2, wherein the polypeptide comprises one or more amino acid substitutions at the following positions: 235, 88, 205, 240, 311 or 409 and one or more of the following amino acid substitutions: 42K/N/I/H/F, 272D, or 392 K/D/E/Y/N/Q/R/S/T/G.

5. The polypeptide according to claim 2, wherein the polypeptide comprises amino acid substitutions at least in four, five or in all of the following positions: 88, 205, 235, 240, 311 or 409 and has at least one or two of the following amino acid substitutions: 42K/N/I/H/F, 272D or 392 K/D/E/Y/N/Q/R/S/T/G.

6. The polypeptide according to claim 1 having 91, 92, 93, 94, 95, 96, 97, 98, or 99% sequence identity to the amino acid sequence of SEQ ID NO: 1.

7. The polypeptide according to claim 1, wherein the polypeptide further comprises an amino acid substitution in position 88.

8. The polypeptide according to claim 7, wherein the polypeptide has the amino acid 88L.

9. The polypeptide according to claim 1, wherein the polypeptide comprises an amino acid substitution in position 235.

10. The polypeptide according to claim 9, wherein the polypeptide has the amino acid 235R.

11. The polypeptide according to claim 1, wherein the polypeptide further comprises one or more of the following amino acids 121F, 134R, 141P, 229P, or 307K.

12. The polypeptide according to claim 1, comprising an amino acid sequence selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 19, SEQ ID NO: 22, SEQ ID NO: 23, SEQ ID NO: 24, SEQ ID NO: 26, SEQ ID NO: 29, SEQ ID NO: 30, SEQ ID NO: 31, SEQ ID NO: 32, SEQ ID NO: 33 and SEQ ID NO: 34.

13. The polypeptide according to claim 1 having a linker fused at the C-terminus.

14. The polypeptide according to claim 1 having exoamylase activity.

15. The polypeptide according to claim 1 having non-maltogenic exoamylase activity.

16. A food or feed additive comprising the polypeptide of claim 1.

17. The polypeptide according to claim 2, comprising an amino acid sequence selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 29, SEQ ID NO: 30, SEQ ID NO: 31, SEQ ID NO: 32, SEQ ID NO: 33 and SEQ ID NO: 34.

18. A food, feed product, dough product or bakery product, comprising a polypeptide of claim 1.

19. A method of making a saccharide syrup, comprising adding a polypeptide according to claim 1 to a granular starch liquefact to form the saccharide syrup.

* * * * *